(12) United States Patent
Calderoni

(10) Patent No.: US 10,973,518 B2
(45) Date of Patent: Apr. 13, 2021

(54) END-STOP DETECTION

(71) Applicant: Covidien LP, Mansfield, MA (US)

(72) Inventor: Anthony Calderoni, Bristol, CT (US)

(73) Assignee: COVIDIEN LP, Mansfield, MA (US)

( * ) Notice: Subject to any disclaimer, the term of this patent is extended or adjusted under 35 U.S.C. 154(b) by 242 days.

(21) Appl. No.: 15/973,773

(22) Filed: May 8, 2018

(65) Prior Publication Data

US 2018/0256165 A1 Sep. 13, 2018

Related U.S. Application Data

(62) Division of application No. 14/523,300, filed on Oct. 24, 2014, now Pat. No. 9,974,541.

(Continued)

(51) Int. Cl.
*A61B 17/072* (2006.01)
*A61B 17/00* (2006.01)
(Continued)

(52) U.S. Cl.
CPC ...... *A61B 17/07207* (2013.01); *A61B 17/068* (2013.01); *A61B 90/03* (2016.02);
(Continued)

(58) Field of Classification Search
CPC . A61B 17/07207; A61B 17/068; A61B 90/03; A61B 2017/00685;
(Continued)

(56) References Cited

U.S. PATENT DOCUMENTS 2,060,997 A 11/1936 Lockett
2,315,582 A 4/1943 Blodgett
(Continued)

FOREIGN PATENT DOCUMENTS

EP 2044890 A1 4/2009
EP 2090240 A1 8/2009
(Continued)

OTHER PUBLICATIONS

Extended European Search Report corresponding to counterpart Int'l Appln. No. EP 17157100.3 dated Jun. 21, 2017.
(Continued)

*Primary Examiner* — Robert F Long
*Assistant Examiner* — Eduardo R Ferrero

(57) ABSTRACT

The present disclosure is directed to systems and methods for operating an electromechanical surgical system. The electromechanical surgical system includes a hand-held surgical instrument including an instrument housing defining a connecting portion for selectively connecting with a shaft assembly. The system also includes an end effector configured to perform at least one function. The shaft assembly is arranged for selectively interconnecting the end effector and the hand-held surgical instrument. The shaft assembly includes a drive member, a flag member configured to translate axially along the drive member, and a sensor disposed about the drive member. The sensor provides a signal indicating that the end effector has reached an end stop when the flag member contacts that sensor.

14 Claims, 39 Drawing Sheets

Related U.S. Application Data

(60) Provisional application No. 61/940,004, filed on Feb. 14, 2014.

(51) Int. Cl.
  *A61B 17/068* (2006.01)
  *A61B 90/00* (2016.01)
  *A61B 17/29* (2006.01)

(52) U.S. Cl.
  CPC .............. *A61B 2017/00017* (2013.01); *A61B 2017/0046* (2013.01); *A61B 2017/00132* (2013.01); *A61B 2017/00314* (2013.01); *A61B 2017/00327* (2013.01); *A61B 2017/00402* (2013.01); *A61B 2017/00407* (2013.01); *A61B 2017/00477* (2013.01); *A61B 2017/00685* (2013.01); *A61B 2017/00734* (2013.01); *A61B 2017/07221* (2013.01); *A61B 2017/07257* (2013.01); *A61B 2017/07271* (2013.01); *A61B 2017/2903* (2013.01); *A61B 2090/034* (2016.02); *A61B 2090/0811* (2016.02)

(58) Field of Classification Search
  CPC .. A61B 2017/00327; A61B 2017/2903; A61B 2017/00477; A61B 2017/0046; A61B 2017/00132; A61B 2017/00314; A61B 2017/00402; A61B 2017/00407; A61B 2017/07221; A61B 2017/07257; A61B 2017/07271; A61B 2017/00017; A61B 2017/00734; A61B 2090/034; A61B 2090/0811
  See application file for complete search history.

(56) References Cited

U.S. PATENT DOCUMENTS

| | | | |
|---|---|---|---|
| 2,648,040 A | 8/1953 | Schneider | |
| 2,679,559 A | 5/1954 | Morris | |
| 2,869,386 A | 1/1959 | Hoover | |
| 3,002,598 A | 10/1961 | Hoover | |
| 3,048,760 A | 8/1962 | Hoover | |
| 3,529,104 A | 9/1970 | Angle | |
| 3,761,746 A | 9/1973 | Adler | |
| 3,766,415 A | 10/1973 | Dame | |
| 4,023,054 A | 5/1977 | Taylor | |
| 4,117,341 A | 9/1978 | Persson | |
| 5,090,190 A | 2/1992 | Slavik | |
| 5,383,880 A * | 1/1995 | Hooven | A61B 17/072 227/175.1 |
| 5,487,378 A | 1/1996 | Robertson et al. | |
| 5,523,827 A | 6/1996 | Snelling | |
| 5,542,594 A | 8/1996 | McKean et al. | |
| 5,605,659 A | 2/1997 | Moynihan | |
| 5,814,275 A | 9/1998 | Lewis | |
| 5,908,427 A | 6/1999 | McKean et al. | |
| 5,964,774 A | 10/1999 | McKean et al. | |
| 6,045,560 A | 4/2000 | McKean et al. | |
| 6,238,481 B1 | 5/2001 | Yamashita | |
| 6,283,719 B1 | 9/2001 | Frantz | |
| 6,620,237 B2 | 9/2003 | Hoisington | |
| 6,866,204 B2 | 3/2005 | Becker et al. | |
| 7,103,460 B1 | 9/2006 | Breed | |
| 7,401,525 B2 | 7/2008 | Cobianu | |
| 7,804,599 B2 | 9/2010 | Calderoni | |
| 7,823,592 B2 | 11/2010 | Bettuchi et al. | |
| 7,845,537 B2 | 12/2010 | Shelton, IV et al. | |
| 7,963,433 B2 | 6/2011 | Whitman et al. | |
| 8,006,886 B2 | 8/2011 | Sonnenschein et al. | |
| 8,118,206 B2 | 2/2012 | Zand et al. | |
| 8,365,972 B2 | 2/2013 | Aranyi et al. | |
| 9,113,880 B2 | 8/2015 | Zemlok et al. | |
| 9,439,649 B2 | 9/2016 | Shelton, IV | |
| 9,974,541 B2 | 5/2018 | Calderoni | |
| 2001/0045442 A1* | 11/2001 | Whitman | A61B 17/07207 227/180.1 |
| 2006/0085034 A1 | 4/2006 | Bettuchi | |
| 2007/0175949 A1 | 8/2007 | Shelton et al. | |
| 2007/0175950 A1* | 8/2007 | Shelton, IV | A61B 17/07207 227/176.1 |
| 2007/0175951 A1* | 8/2007 | Shelton, IV | A61B 17/07207 227/176.1 |
| 2007/0175956 A1 | 8/2007 | Swayze et al. | |
| 2007/0175960 A1* | 8/2007 | Shelton, IV | A61B 17/07207 227/178.1 |
| 2007/0175961 A1* | 8/2007 | Shelton, IV | A61B 17/07207 227/178.1 |
| 2007/0175964 A1 | 8/2007 | Shelton et al. | |
| 2007/0246507 A1 | 10/2007 | Sonnenschein et al. | |
| 2008/0255413 A1 | 10/2008 | Zemlok et al. | |
| 2008/0300580 A1 | 12/2008 | Shelton, IV et al. | |
| 2009/0206136 A1* | 8/2009 | Moore | A61B 17/07207 227/176.1 |
| 2009/0272785 A1 | 11/2009 | Sonnenschein et al. | |
| 2010/0089974 A1 | 4/2010 | Shelton, IV | |
| 2011/0089220 A1 | 4/2011 | Ingmanson et al. | |
| 2011/0121049 A1 | 5/2011 | Malinouskas et al. | |
| 2011/0174099 A1* | 7/2011 | Ross | A61B 17/072 74/89.32 |
| 2011/0204119 A1* | 8/2011 | McCuen | A61B 17/068 227/175.1 |
| 2011/0288573 A1* | 11/2011 | Yates | A61B 34/71 606/170 |
| 2011/0290855 A1* | 12/2011 | Moore | A61B 17/105 227/180.1 |
| 2011/0290856 A1 | 12/2011 | Shelton, IV et al. | |
| 2012/0080503 A1* | 4/2012 | Woodard, Jr. | A61B 17/068 227/181.1 |
| 2012/0116388 A1* | 5/2012 | Houser | H01M 10/46 606/41 |
| 2012/0265230 A1 | 10/2012 | Yates et al. | |

FOREIGN PATENT DOCUMENTS

| | | |
|---|---|---|
| JP | H0751273 A | 2/1995 |
| JP | 2007203053 A | 8/2007 |
| JP | 2014000397 A | 1/2014 |
| WO | 2010090941 A1 | 8/2010 |
| WO | 2012166503 A1 | 12/2012 |

OTHER PUBLICATIONS

European Search Report dated Jun. 16, 2015, issued in European Appln. No. 14199885.

Chinese First Office Action corresponding to counterpart Patent Appln. CN 201410855789.9 dated May 25, 2018.

Japanese office action issued in corresponding Japanese application No. 2014-261718 dated Sep. 4, 2018 with English translation, 10 pages.

* cited by examiner

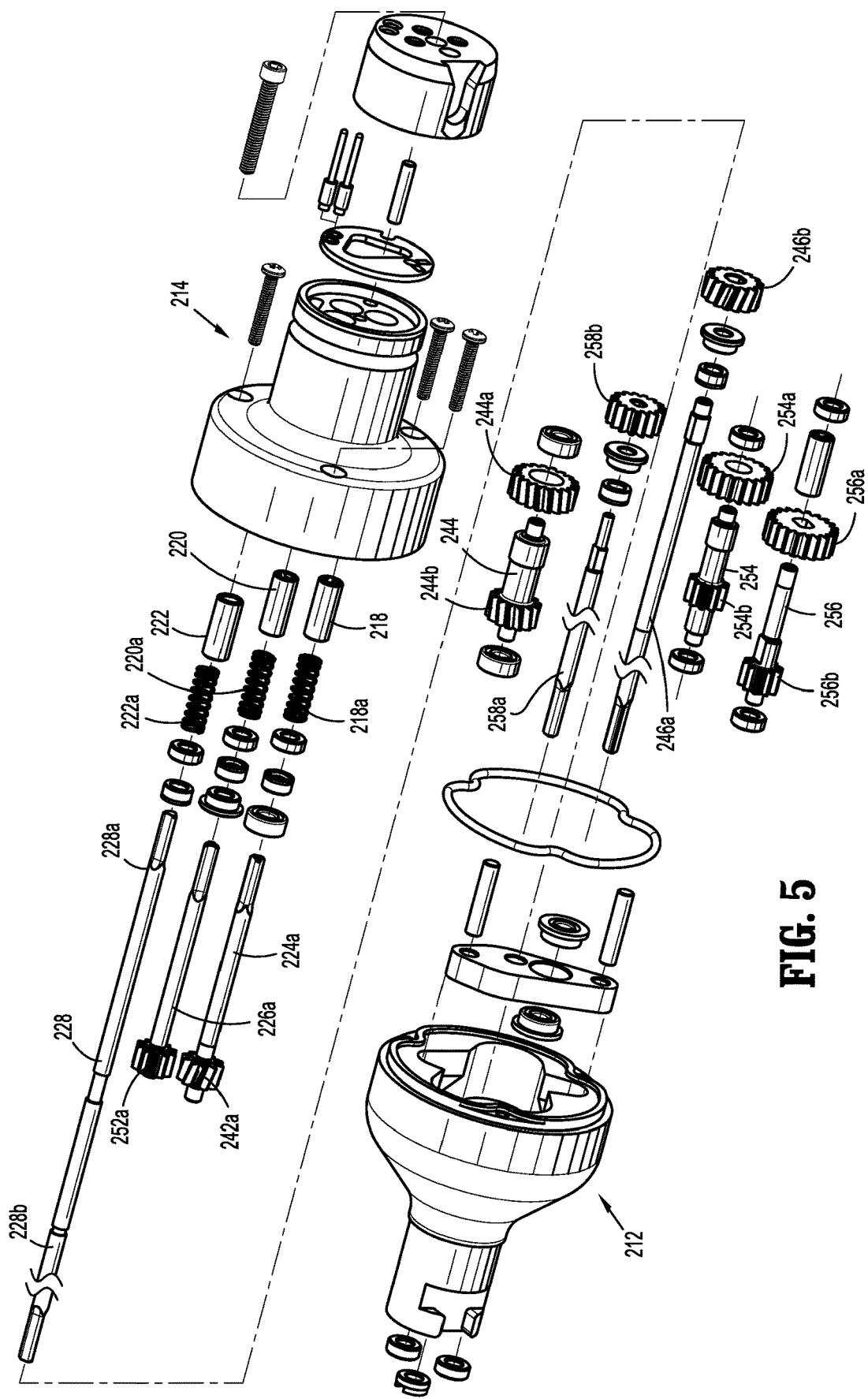

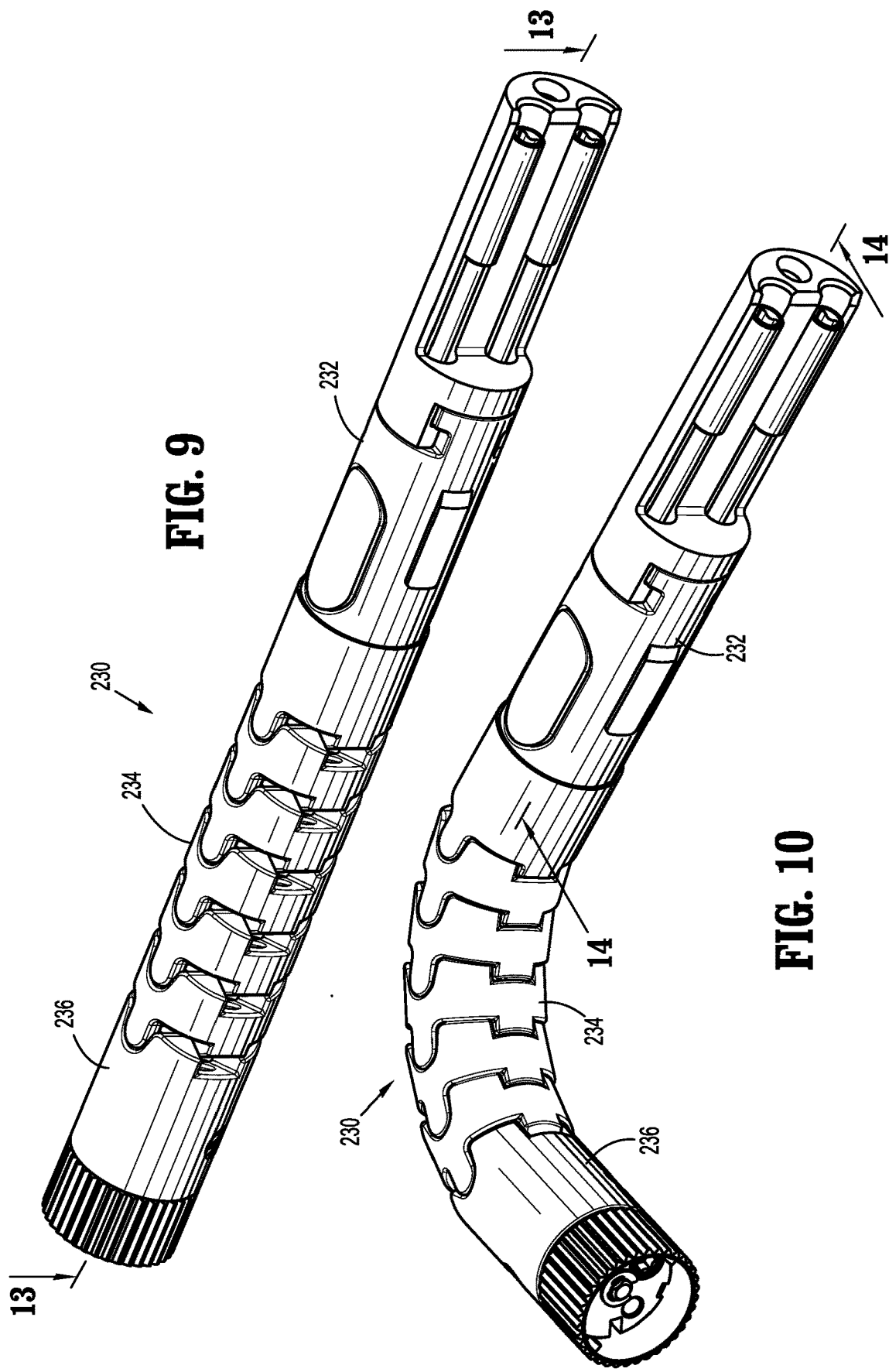

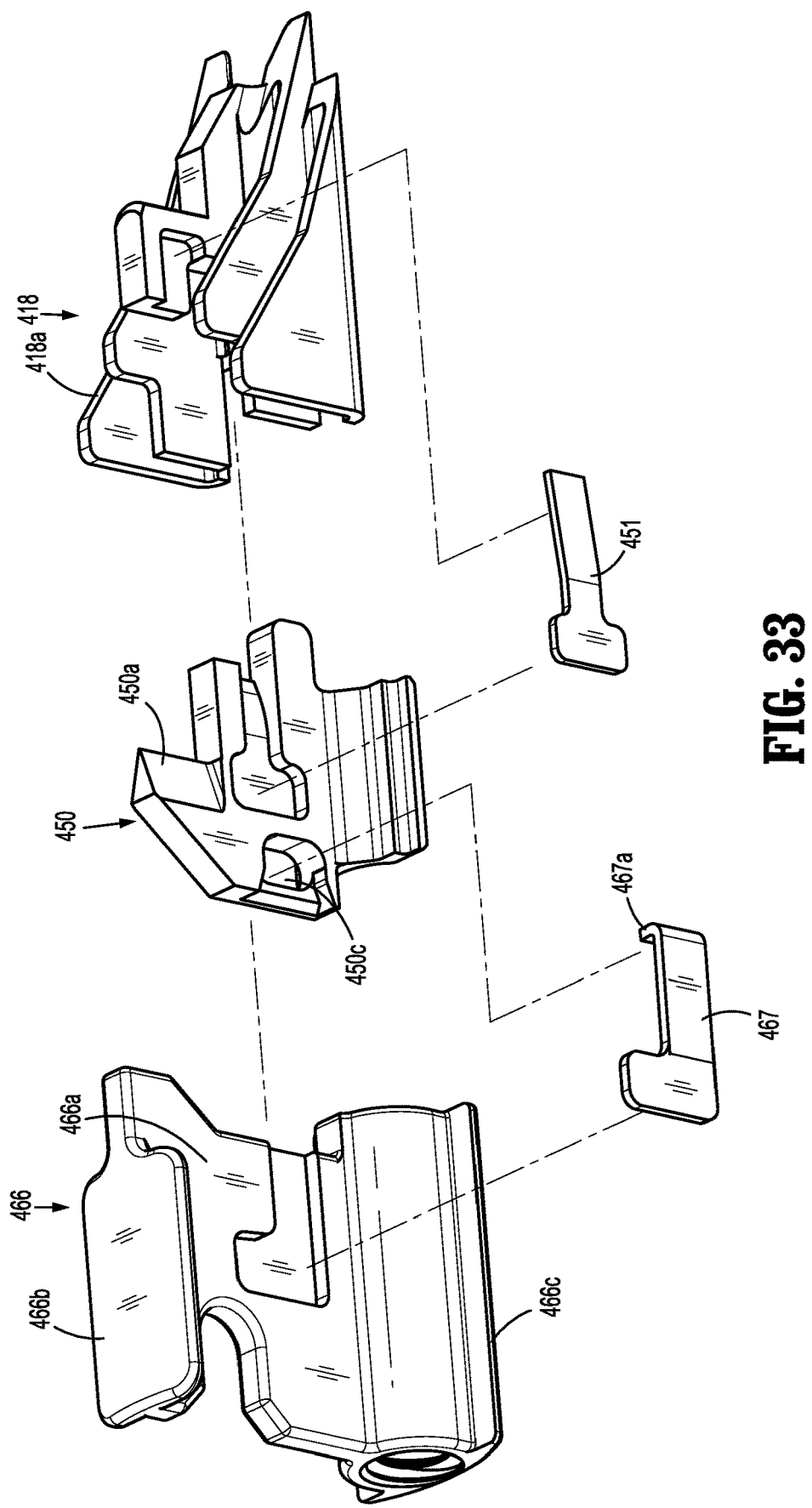

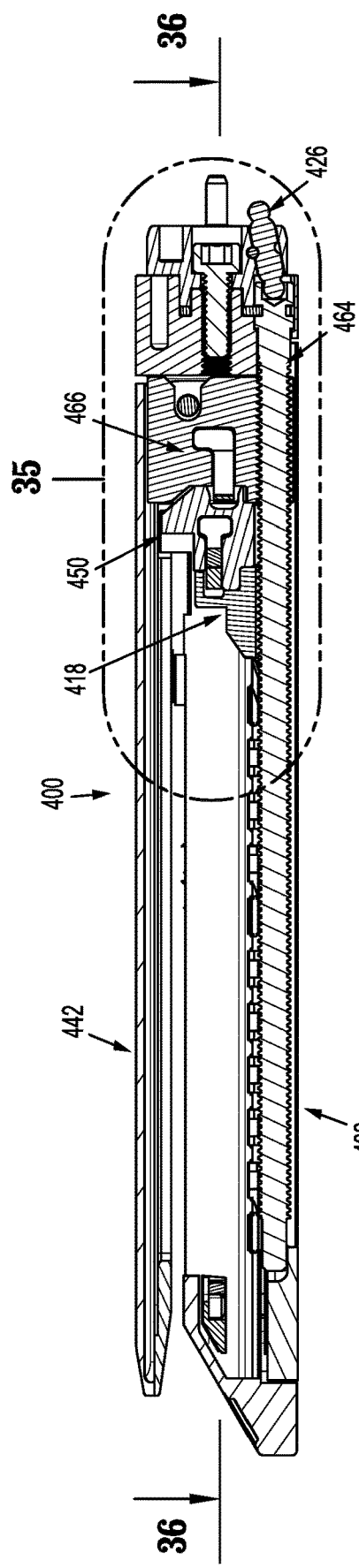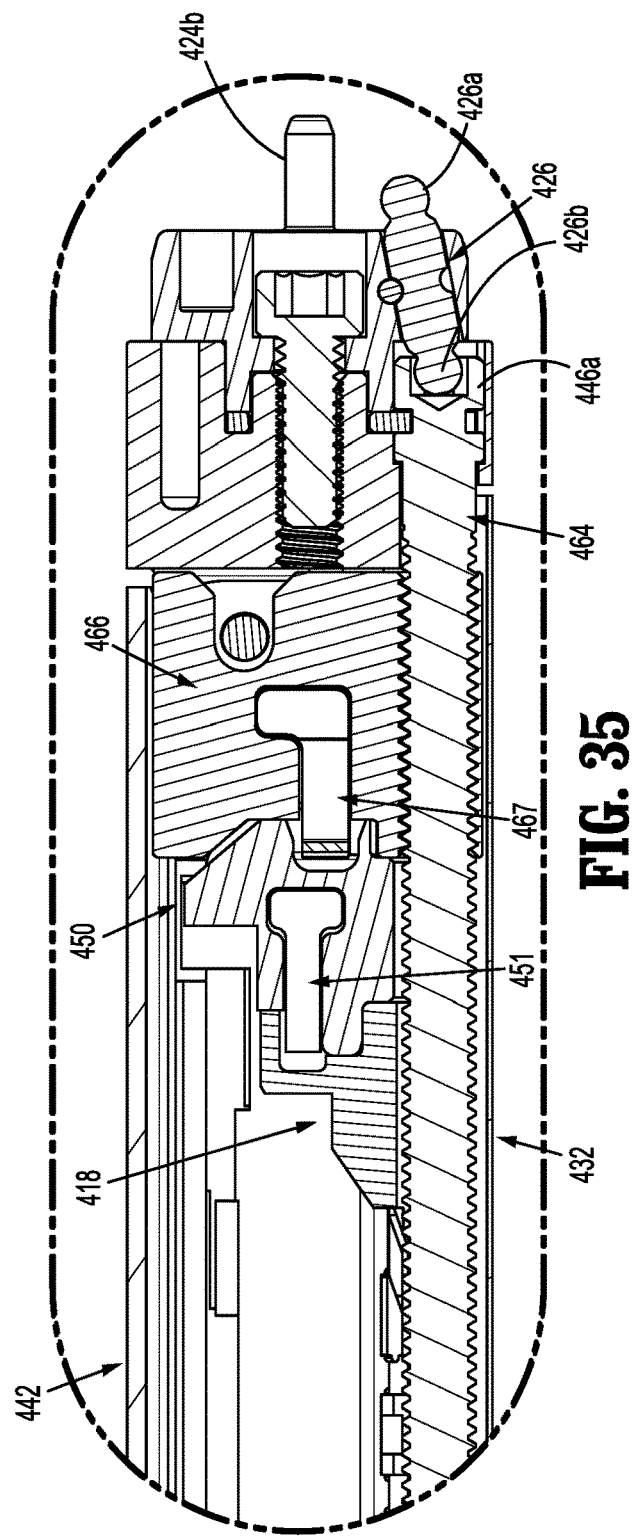

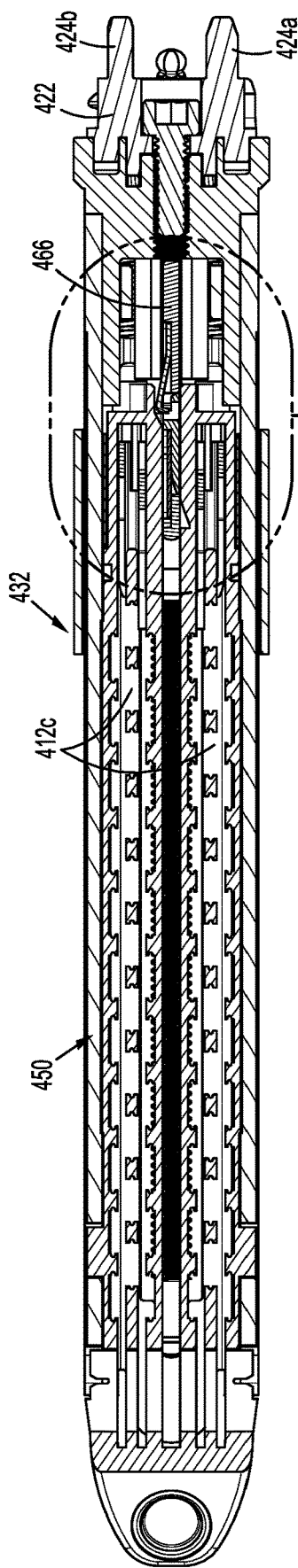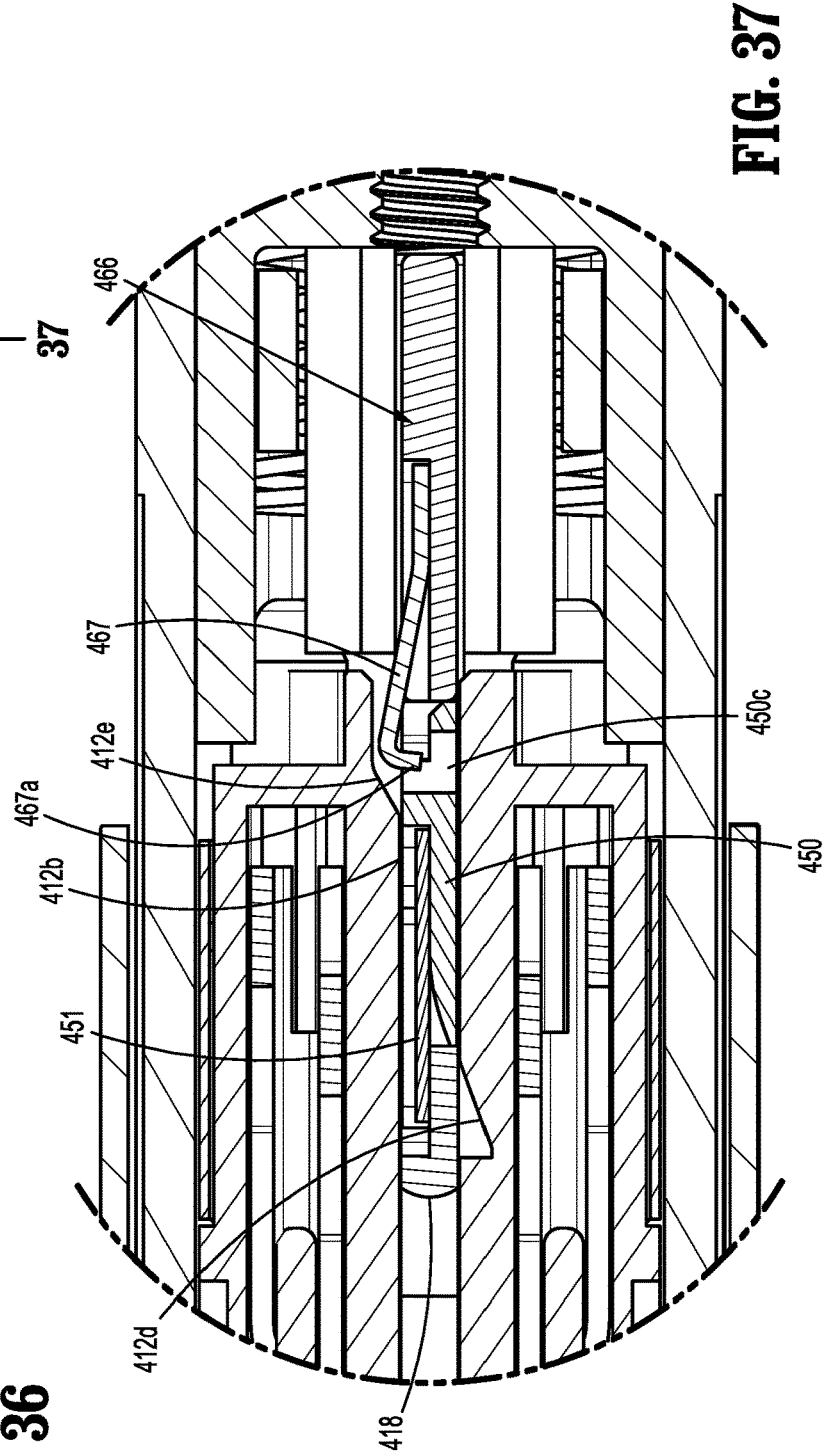

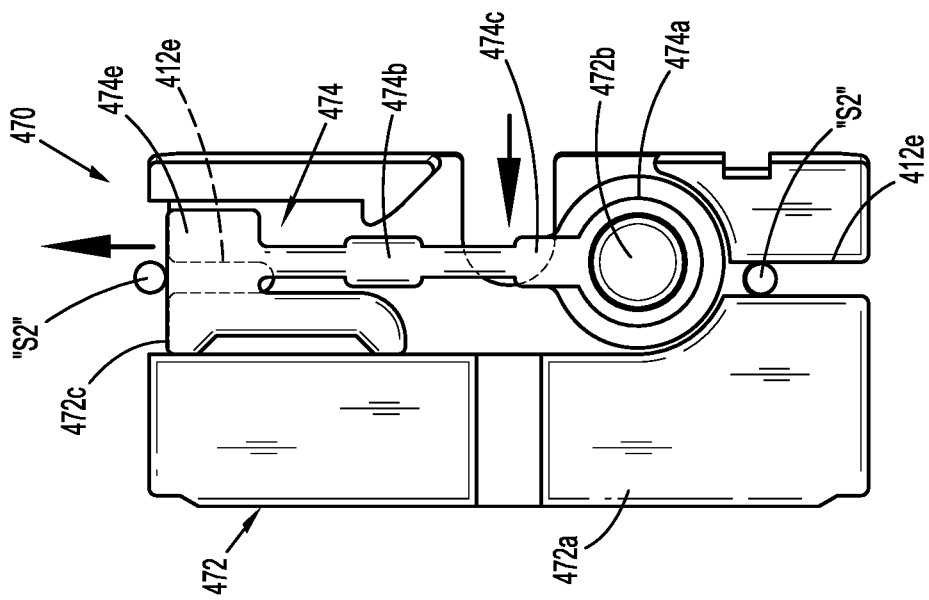
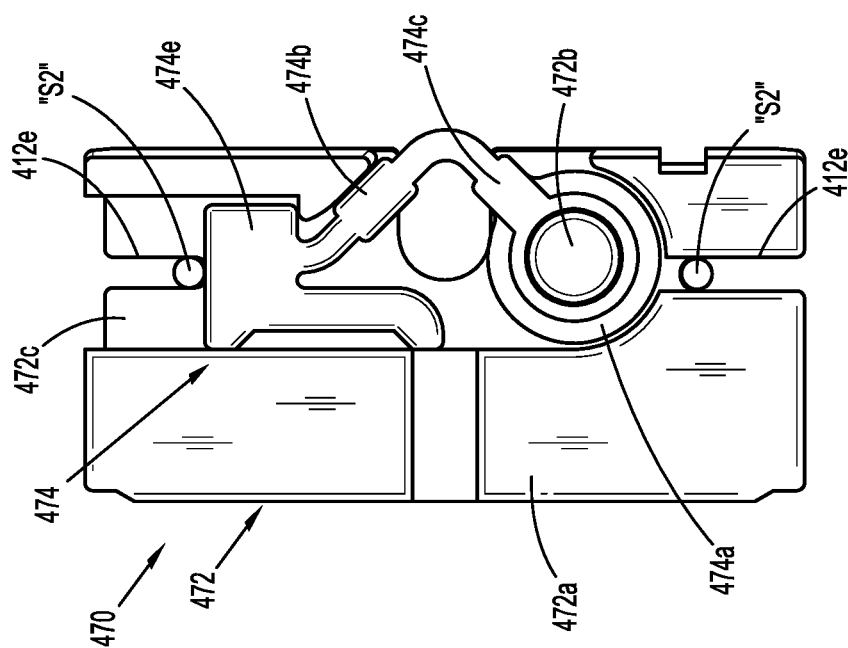

END-STOP DETECTION

CROSS-REFERENCE TO RELATED APPLICATIONS

This application is a divisional application of U.S. patent application Ser. No. 14/523,300, filed on Oct. 24, 2014, which claims the benefit of and priority to U.S. Provisional Patent Application No. 61/940,004, filed Feb. 14, 2014, the entire disclosure of each of which is incorporated by reference herein.

BACKGROUND

1. Technical Field

The present disclosure relates to surgical apparatus, devices and/or systems for performing endoscopic surgical procedures and methods of use thereof. More specifically, the present disclosure relates to electromechanical, hand-held surgical apparatus, devices and/or systems configured for use with removable disposable loading units and/or single use loading units for clamping, cutting and/or stapling tissue.

2. Background of Related Art

A number of surgical device manufacturers have developed product lines with proprietary drive systems for operating and/or manipulating electromechanical surgical devices. Some electromechanical surgical devices include a handle assembly, which is reusable, and replaceable loading units and/or single use loading units or the like that are selectively connected to the handle assembly prior to use and then disconnected from the handle assembly following use, in order to be disposed of or in some instances sterilized for re-use.

The replaceable loading units and/or single use loading units may include staples of various sizes and the staples may be arranged in one or more configurations. After firing the stapler with a replaceable loading unit, the user may remove the empty loading unit, select and attach to the stapler another loading unit having staples of the same or different size and the same or different staple arrangement, and fire the stapler again. This process may be performed repeatedly during a surgical procedure.

The loading units have an end stop which is an indication that all staples have been fired. Rapid detection of the end stop is important to prevent damage to the surgical device. During a surgical procedure, the stapler often detects an end stop of the end-effector assembly by measuring the current from the motor. However, motor current measurements may not be entirely reliable.

Accordingly, a need exists for electromechanical surgical apparatus, devices and/or systems that are capable of rapidly and accurately detecting an end stop of an end effector assembly.

SUMMARY

In an embodiment of the present disclosure, an electromechanical surgical system is provided. The system includes a hand-held surgical instrument including an instrument housing defining a connecting portion for selectively connecting with a shaft assembly. The system also includes an end effector configured to perform at least one function. The shaft assembly is arranged for selectively interconnecting the end effector and the hand-held surgical instrument. The shaft assembly includes a drive member, a flag member configured to translate axially along the first drive member, and a sensor disposed about the first drive member. The sensor provides a signal indicating that the end effector has reached an end stop when the flag member contacts the sensor.

In some aspects, the flag member includes a post and the shaft assembly includes a channel configured to receive the post of the flag member. The channel is configured to prevent rotational movement of the flag member.

In another aspect, the shaft assembly includes a channel configured to receive the sensor, where the channel is configured to prevent axial movement of the sensor.

In yet another aspect, the system also includes a controller, wherein the sensor provides the signal to the controller indicating that the end stop of the end effector has been reached. The system also includes a motor, wherein the controller stops the motor when the controller receives the signal from the sensor.

In aspects of the system, the sensor may include a highly poled piezo crystal or a stack of highly poled piezo crystals.

In another embodiment of the present disclosure, an end stop detection method for a powered surgical instrument having a hand-held surgical instrument, an end effector and a shaft assembly including a drive member, a flag member, and a sensor is provided. The method includes controlling a motor within the hand-held surgical instrument to cause the drive member to rotate in a first direction thereby causing the flag member to translate distally along the drive member. The instrument determines if the flag member contacts the sensor and stops the motor if the flag member contacts the sensor.

In some aspects, after the motor is stopped, the end effector is removed. The instrument then determines if a new end effector is needed based on a user input or a predetermined surgical plan. If a new end effector is needed, a type of end effector to be attached to the shaft assembly as the new end effector is identified. Then the motor is controlled to cause the drive member to rotate in a second direction opposite the first direction thereby causing the flag member to translate proximally along the drive member. The drive member is rotated for a predetermined amount of time based on the type of end effector to be attached to the shaft assembly. Then the new end effector is attached to the shaft assembly.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein:

FIG. 5 is a perspective view, with parts separated of a transmission housing of the shaft assembly;

FIG. 9 is a perspective view of a neck assembly of the shaft assembly, shown in a straight orientation;

FIG. 10 is a perspective view of the neck assembly of FIG. 9, shown in an articulated condition;

FIG. 33 is a perspective view, with parts separated, of the drive beam, the knife sled and the actuation sled of the end effector of FIGS. 27-29;

FIG. 34 is a cross-sectional view of the end effector of FIG. 27, as taken through 34-34 of FIG. 27, illustrating the drive beam, the knife sled and the actuation sled in a proximal-most position;

FIG. 35 is an enlarged view of the indicated area of detail of FIG. 34;

FIG. 36 is a cross-sectional view of the end effector of FIG. 27, as taken through 36-36 of FIG. 34;

FIG. 37 is an enlarged view of the indicated area of detail of FIG. 36;

FIG. 46 is a plan view of the release assembly of FIGS. 44 and 45, shown in an unactuated condition;

FIG. 47 is a plan view of the release assembly of FIGS. 44 and 45, shown in an actuated condition;

DETAILED DESCRIPTION OF EMBODIMENTS

Figure 1:
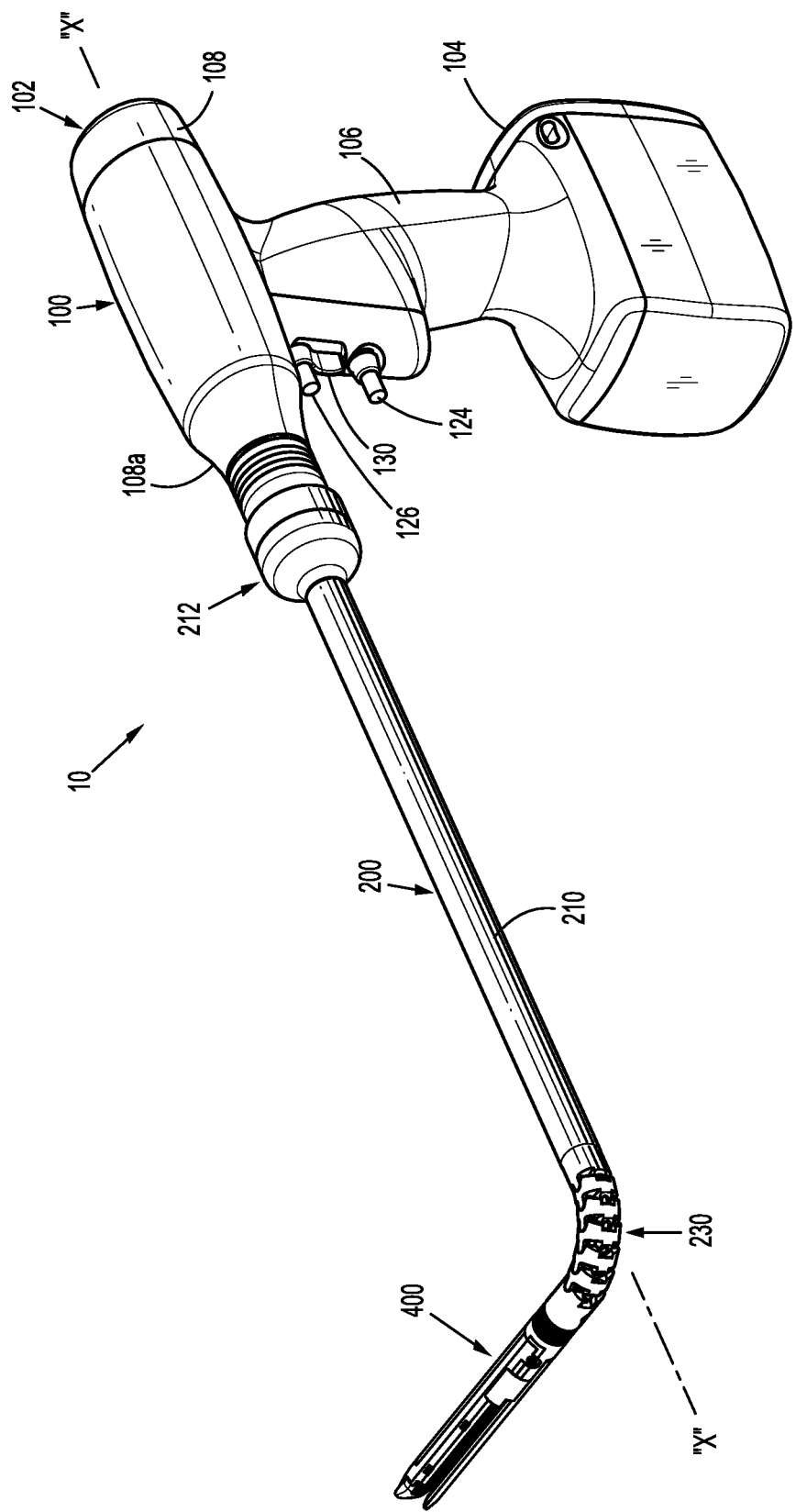
FIG. 1 is a perspective view of an electromechanical surgical system according to an embodiment of the present disclosure.

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A or B" means "(A), (B), or (A and B)". For the purposes of this description, a phrase in the form "at least one of A, B, or C" means "(A), (B), (C), (A and B), (A and C), (B and C), or (A, B and C)".

The term "clinician" refers to any medical professional (i.e., doctor, surgeon, nurse, or the like) performing a medical procedure involving the use of embodiments described herein. As shown in the drawings and described throughout the following description, as is traditional when referring to relative positioning on a surgical instrument, the term "proximal" or "trailing" refers to the end of the apparatus which is closer to the clinician and the term "distal" or "leading" refers to the end of the apparatus which is further away from the clinician.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" is any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other meta-languages. For the purposes of this definition, no distinction is made between languages which are interpreted, compiled, or use both compiled and interpreted approaches. For the purposes of this definition, no distinction is made between compiled and source versions of a program. Thus, reference to a program, where the programming language could exist in more than one state (such as source, compiled, object, or linked) is a reference to any and all such states. The definition also encompasses the actual instructions and the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

In embodiments described herein, a powered surgical device includes a piezo device used to detect the end stop of an end effector. A flag member is mounted on a drive shaft and translated axially upon actuation of the end effector. When the flag member contacts the piezo device, the piezo device provide a high electrical signal to a controller which turns off the motor controlling the drive shaft thereby stopping actuation of the end effector.

Figure 2:
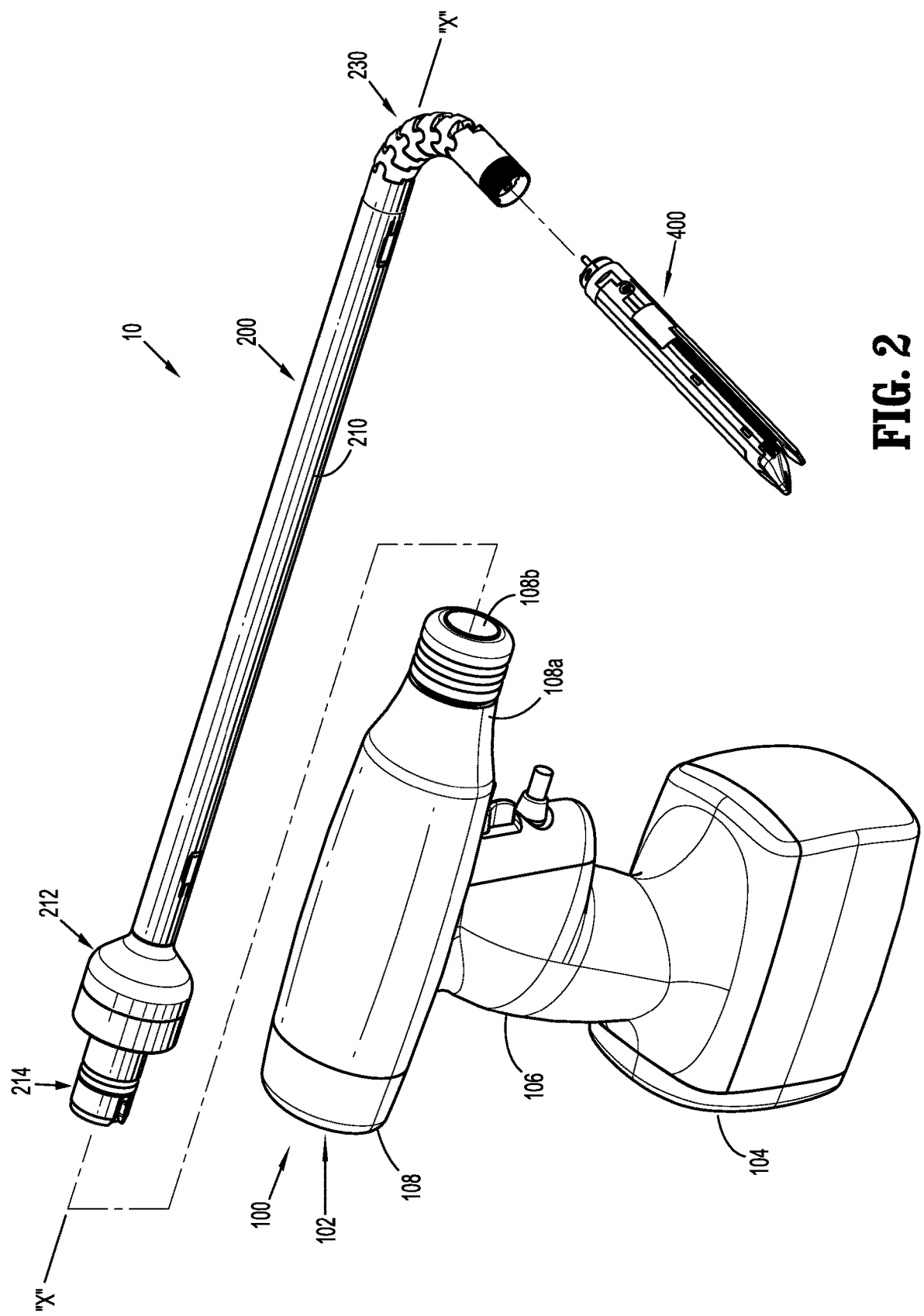
FIG. 2 is a perspective view, with parts separated, of the electromechanical surgical system of FIG. 1.
Figure 3:
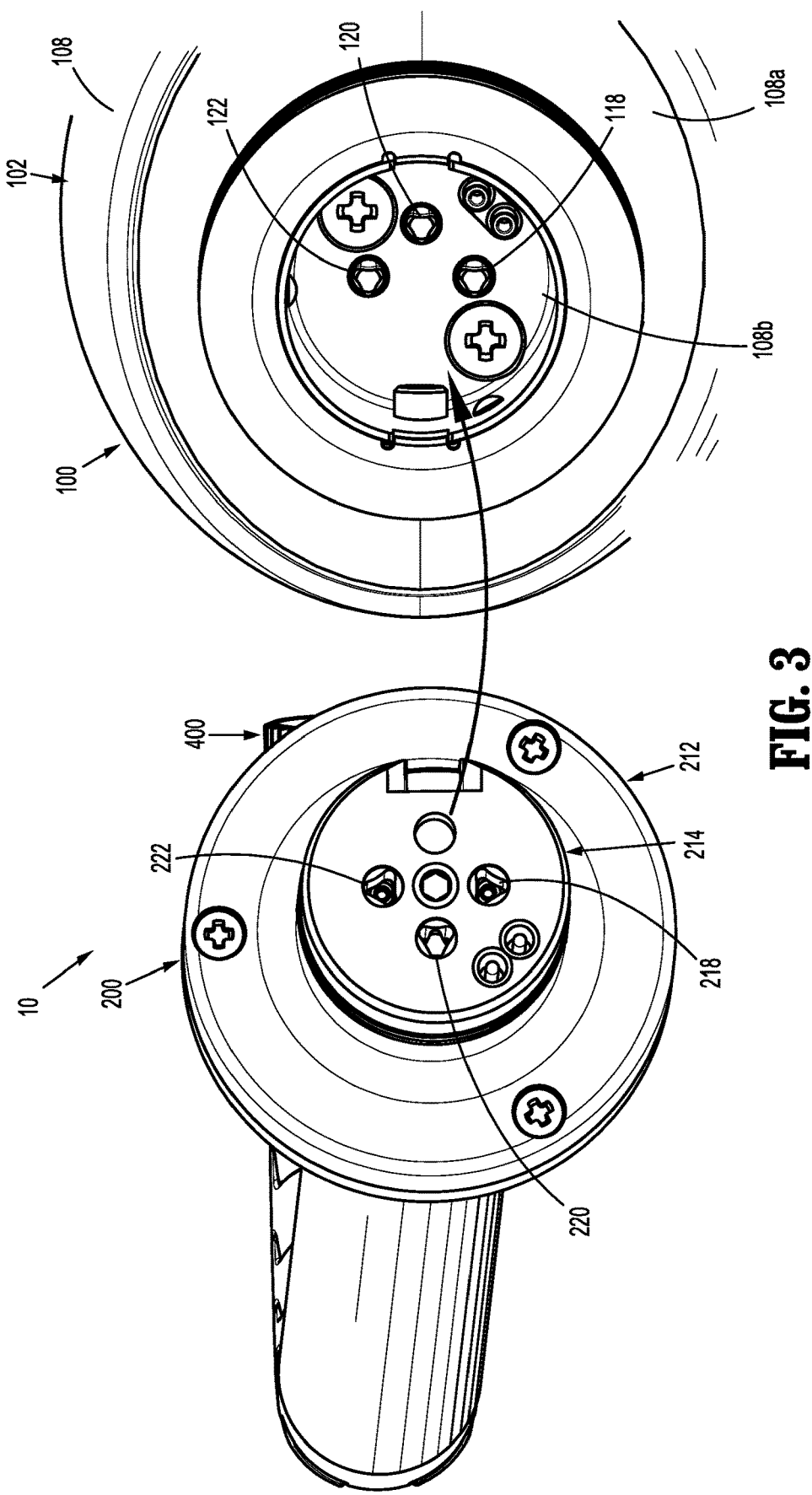
FIG. 3 is a rear, perspective view of a shaft assembly and a powered surgical instrument, of the electromechanical surgical system of FIGS. 1 and 2, illustrating a connection therebetween.

Referring initially to FIGS. 1-3, an electromechanical, hand-held, powered surgical system, in accordance with an embodiment of the present disclosure is shown and generally designated 10. Electromechanical surgical system 10 includes a surgical apparatus or device in the form of an electromechanical, hand-held, powered surgical instrument 100 that is configured for selective attachment thereto of a plurality of different end effectors 400, via a shaft assembly 200, that are each configured for actuation and manipulation by the electromechanical, hand-held, powered surgical instrument 100. In particular, surgical instrument 100 is configured for selective connection with shaft assembly 200, and, in turn, shaft assembly 200 is configured for selective connection with any one of a plurality of different end effectors 400.

Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009 (U.S. Patent Application Publication No. 2011/0121049), the entire content of each of which are hereby incorporated herein by reference, for a detailed description of the construction and operation of exemplary electromechanical, hand-held, powered surgical instrument 100

Generally, as illustrated in FIGS. 1-3, surgical instrument 100 includes an instrument housing 102 having a lower housing portion 104, an intermediate housing portion 106 extending from and/or supported on lower housing portion 104, and an upper housing portion 108 extending from and/or supported on intermediate housing portion 106. The surgical instrument 100 has a controller for controlling certain functions of the surgical system, collecting data, and performing other functions. Instrument housing 102 defines a cavity therein in which a circuit board (not shown) and a drive mechanism (not shown) are situated.

The circuit board is configured to control the various operations of surgical instrument 100, as will be set forth in additional detail below. In accordance with the present disclosure, instrument housing 102 provides a housing in which a rechargeable battery (not shown), is removably situated. The battery is configured to supply power to any of the electrical components of surgical instrument 100.

Upper housing portion 108 of instrument housing 102 defines a nose or connecting portion 108a configured to accept a corresponding shaft coupling assembly 214 of transmission housing 212 of shaft assembly 200. As seen in FIG. 3, connecting portion 108a of upper housing portion 108 of surgical instrument 100 has a cylindrical recess 108b that receives shaft coupling assembly 214 of transmission housing 212 of shaft assembly 200 when shaft assembly 200 is mated to surgical instrument 100. The connecting portion 108a of the surgical instrument 100 has at least one rotatable drive member. In particular, connecting portion 108a houses three rotatable drive members or connectors 118, 120, 122, each independently actuatable and rotatable by the drive mechanism (not shown) housed within instrument housing 102.

Upper housing portion 108 of instrument housing 102 provides a housing in which the drive mechanism (not shown) is situated. The drive mechanism is configured to drive shafts and/or gear components in order to perform the various operations of surgical instrument 100. In particular, the drive mechanism is configured to drive shafts and/or gear components in order to selectively move end effector 400 relative to shaft assembly 200; to rotate anvil assembly 200 and/or end effector 400, about a longitudinal axis "X" (see FIGS. 1 and 2), relative to instrument housing 102; to move an upper jaw or anvil assembly 442 of end effector 400 relative to a lower jaw or cartridge assembly 432 of end effector 400; to articulate and/or rotate the shaft assembly; and/or to fire a stapling and cutting cartridge within cartridge assembly 432 of end effector 400.

The shaft assembly 200 has a force transmitting assembly for interconnecting the at least one drive member of the surgical instrument to at least one rotation receiving member of the end effector. The force transmitting assembly has a first end that is connectable to the at least one rotatable drive member and a second end that is connectable to the at least one rotation receiving member of the end effector. When shaft assembly 200 is mated to surgical instrument 100, each of rotatable drive members or connectors 118, 120, 122 of surgical instrument 100 couples with a corresponding rotatable connector sleeve 218, 220, 222 of shaft assembly 200 (see FIGS. 3 and 5). In this regard, the interface between corresponding first drive member or connector 118 and first connector sleeve 218, the interface between corresponding second drive member or connector 120 and second connector sleeve 220, and the interface between corresponding third drive member or connector 122 and third connector sleeve 222 are keyed such that rotation of each of drive members or connectors 118, 120, 122 of surgical instrument 100 causes a corresponding rotation of the corresponding connector sleeve 218, 220, 222 of shaft assembly 200.

The mating of drive members or connectors 118, 120, 122 of surgical instrument 100 with connector sleeves 218, 220, 222 of shaft assembly 200 allows rotational forces to be independently transmitted via each of the three respective connector interfaces. The drive members or connectors 118, 120, 122 of surgical instrument 100 are configured to be independently rotated by the drive mechanism. In this regard, the controller has a function selection module (not shown) of the drive mechanism selects which drive member or connector 118, 120, 122 of surgical instrument 100 is to be driven by an input drive component (not shown) of the drive mechanism.

Since each of drive members or connectors 118, 120, 122 of surgical instrument 100 has a keyed and/or substantially non-rotatable interface with respective connector sleeves 218, 220, 222 of shaft assembly 200, when shaft assembly 200 is coupled to surgical instrument 100, rotational force(s) are selectively transferred from the drive mechanism of surgical instrument 100 to shaft assembly 200, and on to end effector 400, as will be discussed in greater detail below.

The selective rotation of drive member(s) or connector(s) 118, 120 and/or 122 of surgical instrument 100 allows surgical instrument 100 to selectively actuate different functions of end effector 400. As will be discussed in greater detail below, selective and independent rotation of first drive member or connector 118 of surgical instrument 100 corresponds to the selective and independent opening and closing of end effector 400, and driving of a stapling/cutting component of end effector 400. Also, the selective and independent rotation of second drive member or connector 120 of surgical instrument 100 corresponds to the selective and independent articulation of end effector 400 transverse to longitudinal axis "X" (see FIG. 1). Additionally, the selective and independent rotation of third drive member or connector 122 of surgical instrument 100 corresponds to the selective and independent rotation of end effector 400 about longitudinal axis "X" (see FIG. 1) relative to instrument housing 102 of surgical instrument 100.

In accordance with the present disclosure, the drive mechanism may include a selector gearbox assembly (not shown); a function selection module (not shown), located proximal to the selector gearbox assembly, that functions to selectively move gear elements within the selector gearbox assembly into engagement with a second motor (not shown). The drive mechanism may be configured to selectively drive one of drive members or connectors 118, 120, 122 of surgical instrument 100, at a given time.

As illustrated in FIGS. 1 and 2, instrument housing 102 supports a pair of finger-actuated control buttons 124, 126 and/or rocker device(s) 130 (only one rocker device being shown). Each one of the control buttons 124, 126 and rocker device(s) 130 includes a respective magnet (not shown) that is moved by the actuation of an operator. In addition, the circuit board (not shown) housed in instrument housing 102 includes, for each one of the control buttons 124, 126 and rocker device(s) 130, respective Hall-effect switches (not shown) that are actuated by the movement of the magnets in the control buttons 124, 126 and rocker device(s) 130. In particular, located immediately proximal to the control button 124 is a respective Hall-effect switch (not shown) that is actuated upon the movement of a magnet within the control button 124 upon the operator actuating control button 124. The actuation of Hall-effect switch (not shown), corresponding to control button 124, causes the circuit board to provide appropriate signals to the function selection module and the input drive component of the drive mechanism to close end effector 400 and/or to fire a stapling/cutting cartridge within end effector 400.

Also, located immediately proximal to control button 126 is a respective Hall-effect switch (not shown) that is actuated upon the movement of a magnet (not shown) within control button 126 upon the operator actuating control button 126. The actuation of the Hall-effect switch, corresponding to control button 126, causes the circuit board to provide appropriate signals to the function selection module and the input drive component of the drive mechanism to open/close end effector 400.

In addition, located immediately proximal to rocker device 130 is a respective Hall-effect switch (not shown) that is actuated upon the movement of a magnet (not shown) within rocker device 130 upon the operator actuating rocker device 130. The actuation of the Hall-effect switch, corresponding to rocker device 130, causes the circuit board to provide appropriate signals to the function selection module and the input drive component of the drive mechanism to rotate end effector 400 relative to shaft assembly 200 or rotate end effector 400 and shaft assembly 200 relative to instrument housing 102 of surgical instrument 100. Specifically, movement of rocker device 130 in a first direction causes end effector 400 and/or shaft assembly 200 to rotate relative to instrument housing 102 in a first direction, while movement of rocker device 130 in an opposite, e.g., second, direction causes end effector 400 and/or shaft assembly 200 to rotate relative to instrument housing 102 in an opposite, e.g., second, direction.

Turning now to FIGS. 1-26, shaft assembly 200 will be shown in detail and described. Shaft assembly 200 is configured to communicate the rotational forces of first, second and third rotatable drive members or connectors 118, 120, and 122 of surgical instrument 100 to end effector 400. As mentioned above, shaft assembly 200 is configured for selective connection to surgical instrument 100.

Figure 4A:
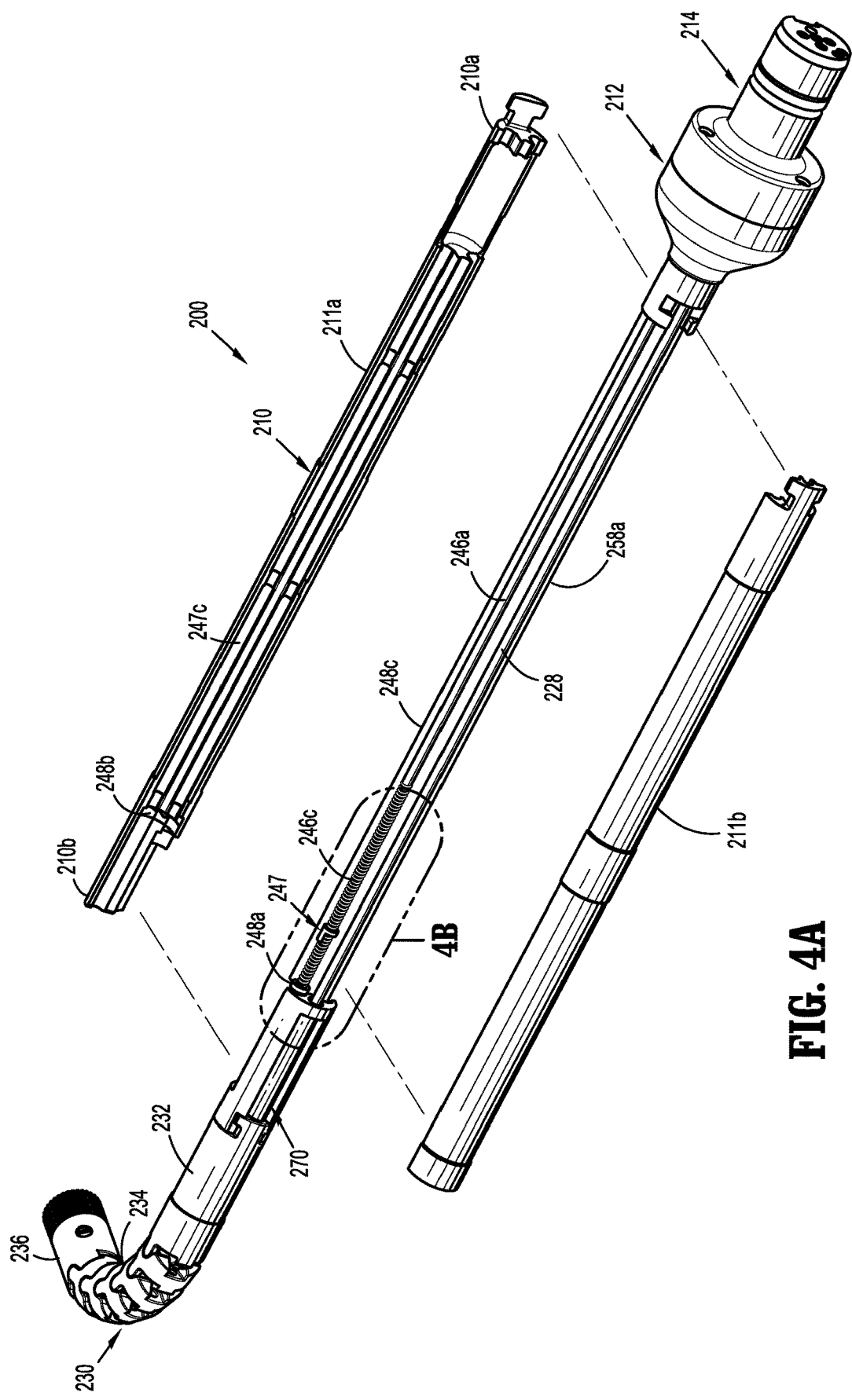
FIG. 4A is a perspective view, with parts separated, of the shaft assembly of FIGS. 1-3.

As seen in FIGS. 1, 2 and 4A, shaft assembly 200 includes an elongate, substantially rigid, outer tubular body 210 having a proximal end 210a and a distal end 210b; a transmission housing 212 connected to proximal end 210a of tubular body 210 and being configured for selective connection to surgical instrument 100; and an articulating neck assembly 230 connected to distal end 210b of elongate body portion 210.

Transmission housing 212 is configured to house a pair of gear train systems therein for varying a speed/force of rotation (e.g., increase or decrease) of first, second and/or third rotatable drive members or connectors 118, 120, and/or 122 of surgical instrument 100 before transmission of such rotational speed/force to end effector 400.

Transmission housing 212 of shaft assembly 200 is configured and adapted to connect to connecting portion 108a of upper housing portion 108 of surgical instrument 100. As seen in FIGS. 3-5, transmission housing 212 of shaft assembly 200 includes a shaft coupling assembly 214 supported at a proximal end thereof.

As seen in FIGS. 5 and 20-25, transmission housing 212 and shaft coupling assembly 214 rotatably support a first proximal or input drive shaft 224a, a second proximal or input drive shaft 226a, and a third drive shaft 228.

Shaft coupling assembly 214 is configured to rotatably support first, second and third connector sleeves 218, 220 and 222, respectively. Each of connector sleeves 218, 220, 222 is configured to mate with respective first, second and third drive members or connectors 118, 120, 122 of surgical instrument 100, as described above. Each of connector sleeves 218, 220, 222 is further configured to mate with a proximal end of respective first input drive shaft 224a, second input drive shaft 226a, and third drive shaft 228.

Shaft drive coupling assembly 214 includes a first, a second and a third biasing member 218a, 220a and 222a disposed distally of respective first, second and third connector sleeves 218, 220, 222. Each of biasing members 218a, 220a and 222a is disposed about respective first proximal drive shaft 224a, second proximal drive shaft 226a, and third drive shaft 228. Biasing members 218a, 220a and 222a act on respective connector sleeves 218, 220 and 222 to help maintain connector sleeves 218, 220 and 222 engaged with the distal end of respective drive rotatable drive members or connectors 118, 120, 122 of surgical instrument 100 when shaft assembly 200 is connected to surgical instrument 100.

In particular, first, second and third biasing members 218a, 220a and 222a function to bias respective connector sleeves 218, 220 and 222 in a proximal direction. In this manner, during connection of shaft assembly 200 to surgical instrument 100, if first, second and or third connector sleeves 218, 220 and/or 222 is/are misaligned with the drive members or connectors 118, 120, 122 of surgical instrument 100, first, second and/or third biasing member(s) 218a, 220a and/or 222a are compressed. Thus, when the drive mechanism of surgical instrument 100 is engaged, drive members or connectors 118, 120, 122 of surgical instrument 100 will rotate and first, second and/or third biasing member(s) 218a, 220a and/or 222a will cause respective first, second and/or third connector sleeve(s) 218, 220 and/or 222 to slide back proximally, effectively coupling drive members or connectors 118, 120, 122 of surgical instrument 100 to respective first input drive shaft 224a, second input drive shaft 226a, and third drive shaft 228.

In use, during a calibration of surgical instrument 100, each of drive connectors 118, 120, 122 of surgical instrument 100 is rotated and the bias on connector sleeve(s) 218, 220 and 222 properly seats connector sleeve(s) 218, 220 and 222 over the respective drive connectors 118, 120, 122 of surgical instrument 100 when the proper alignment is reached.

Shaft assembly 200 includes a first and a second gear train system 240, 250, respectively, disposed within transmission housing 212 and tubular body 210, and adjacent coupling assembly 214. As mentioned above, each gear train system 240, 250 is configured and adapted to vary a speed/force of rotation (e.g., increase or decrease) of first and second rotatable drive connectors 118 and 120 of surgical instrument 100 before transmission of such rotational speed/force to end effector 400.

Figure 6:
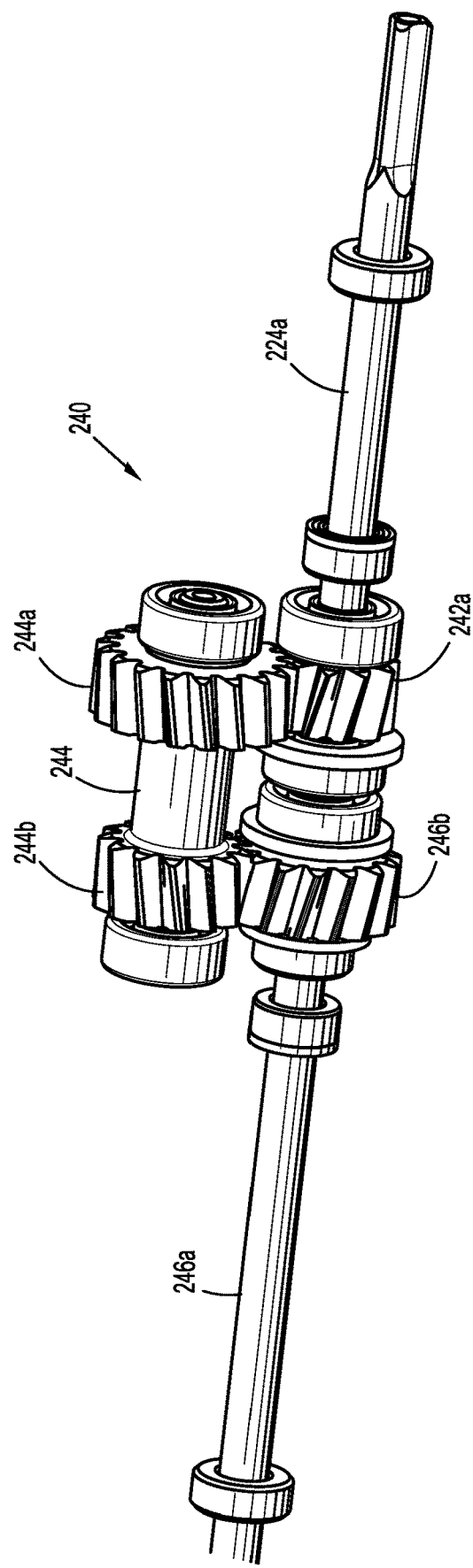
FIG. 6 is a perspective view of a first gear train system that is supported in the transmission housing.

As seen in FIGS. 5 and 6, first gear train system 240 includes first input drive shaft 224a, and a first input drive shaft spur gear 242a keyed to first input drive shaft 224a. First gear train system 240 also includes a first transmission shaft 244 rotatably supported in transmission housing 212, a first input transmission spur gear 244a keyed to first transmission shaft 244 and engaged with first input drive shaft spur gear 242a, and a first output transmission spur gear 244b keyed to first transmission shaft 244. First gear train system 240 further includes a first output drive shaft 246a rotatably supported in transmission housing 212 and tubular body 110, and a first output drive shaft spur gear 246b keyed to first output drive shaft 246a and engaged with first output transmission spur gear 244b.

In accordance with the present disclosure, first input drive shaft spur gear 242a includes 10 teeth; first input transmission spur gear 244a includes 18 teeth; first output transmission spur gear 244b includes 13 teeth; and first output drive shaft spur gear 246b includes 15 teeth. As so configured, an input rotation of first input drive shaft 224a is converted to an output rotation of first output drive shaft 246a by a ratio of 1:2.08.

As mentioned above, a proximal end of first input drive shaft 224a is configured to support first connector sleeve 218.

In operation, as first input drive shaft spur gear 242a is rotated, due to a rotation of first connector sleeve 258 and first input drive shaft 224a, as a result of the rotation of the first respective drive connector 118 of surgical instrument 100, first input drive shaft spur gear 242a engages first input transmission spur gear 244a causing first input transmission spur gear 244a to rotate. As first input transmission spur gear 244a rotates, first transmission shaft 244 is rotated and thus causes first output drive shaft spur gear 246b, that is keyed to first transmission shaft 244, to rotate. As first output drive shaft spur gear 246b rotates, since first output drive shaft spur gear 246b is engaged therewith, first output drive shaft spur gear 246b is also rotated. As first output drive shaft spur gear 246b rotates, since first output drive shaft spur gear 246b is keyed to first output drive shaft 246a, first output drive shaft 246a is rotated.

As will be discussed in greater detail below, shaft assembly 200, including first gear system 240, functions to transmit operative forces from surgical instrument 100 to end effector 400 in order to operate, actuate and/or fire end effector 400.

Figure 7:
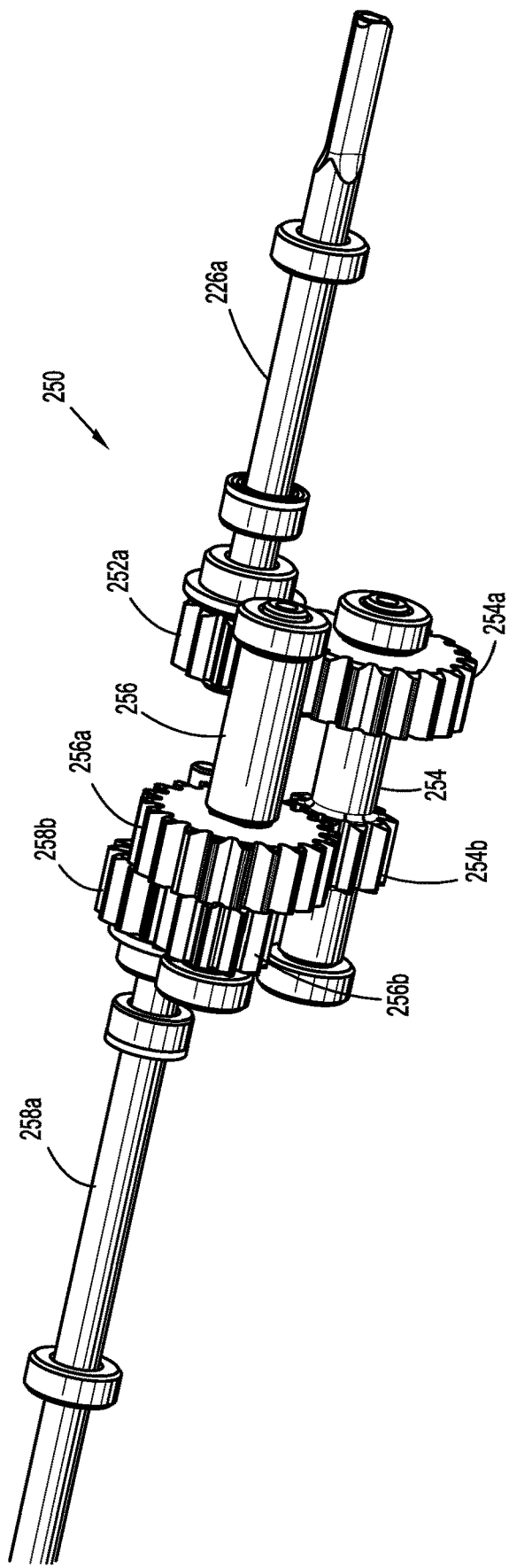
FIG. 7 is a perspective view of a second gear train system that is supported in the transmission housing.
Figure 8:
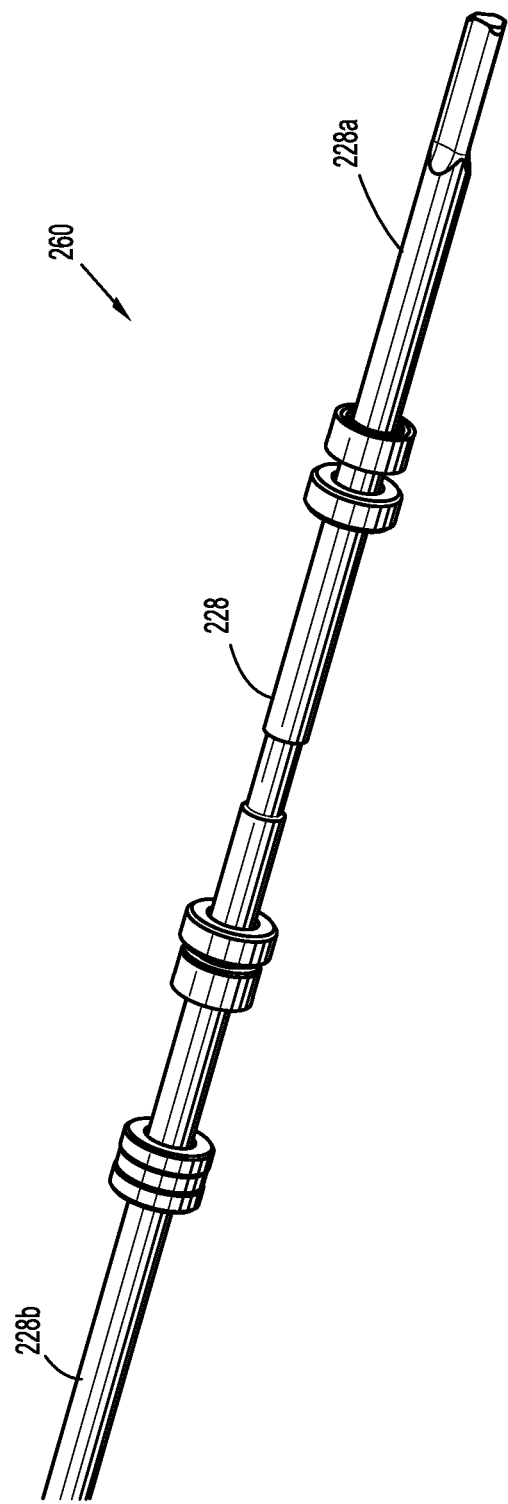
FIG. 8 is a perspective view of a third drive shaft that is supported in the transmission housing.
Figure 11:
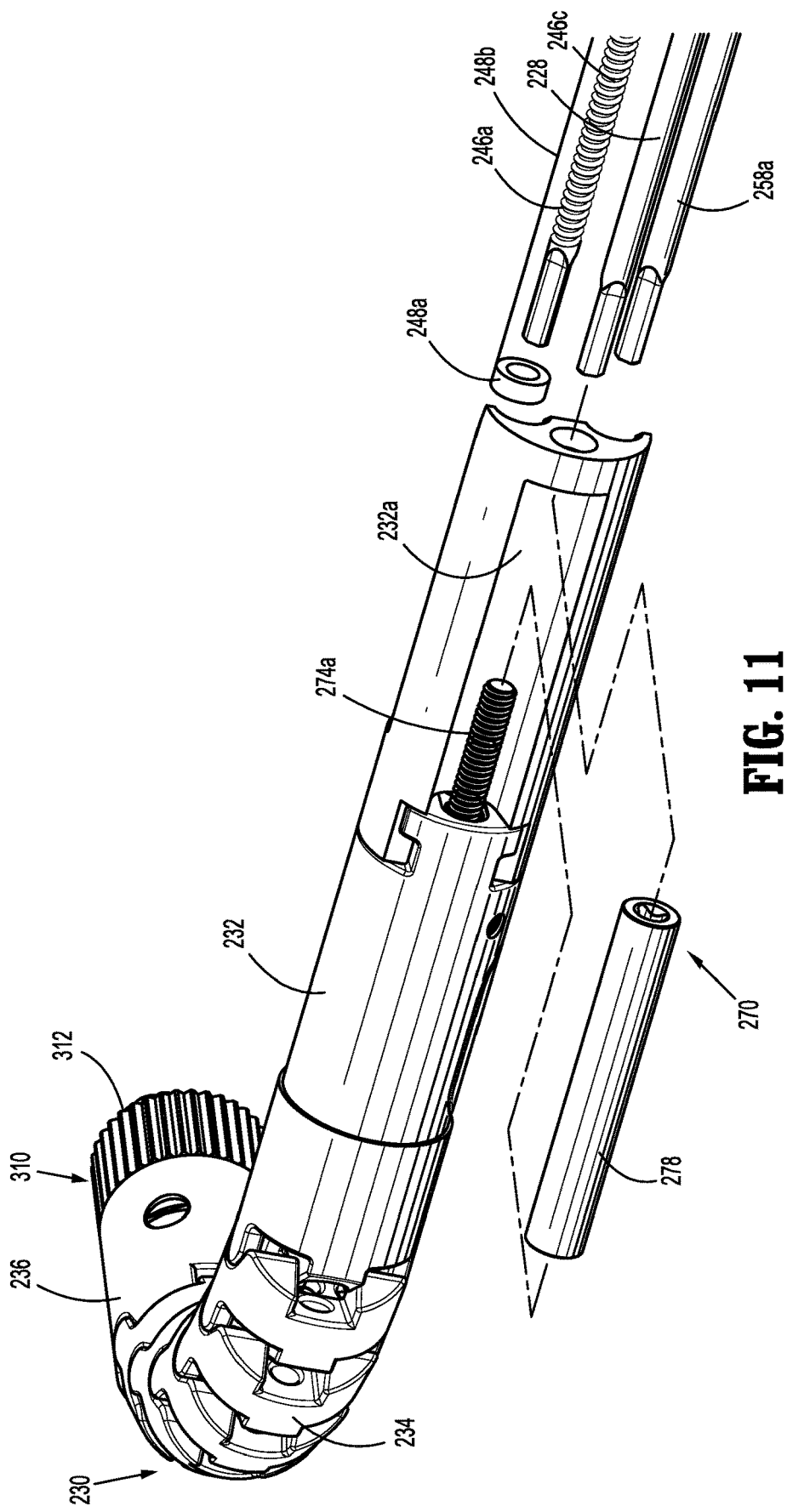
FIG. 11 is a perspective view of the neck assembly of FIGS. 9 and 10, with a threaded nut separated therefrom.

As seen in FIGS. 5 and 7, second gear train system 250 includes second input drive shaft 226a, and a second input drive shaft spur gear 252a keyed to second input drive shaft 226a. Second gear train system 250 also includes a first transmission shaft 254 rotatably supported in transmission housing 212, a first input transmission spur gear 254a keyed to first transmission shaft 254 and engaged with second input drive shaft spur gear 252a, and a first output transmission spur gear 254b keyed to first transmission shaft 254.

Second gear train system 250 further includes a second transmission shaft 256 rotatably supported in transmission housing 212, a second input transmission spur gear 256a keyed to second transmission shaft 256 and engaged with first output transmission spur gear 254b that is keyed to first transmission shaft 254, and a second output transmission spur gear 256b keyed to second transmission shaft 256.

Second gear train system 250 additionally includes a second output drive shaft 258a rotatably supported in transmission housing 212 and tubular body 210, and a second output drive shaft spur gear 258b keyed to second output drive shaft 258a and engaged with second output transmission spur gear 256b.

In accordance with the present disclosure, second input drive shaft spur gear 252a includes 10 teeth; first input transmission spur gear 254a includes 20 teeth; first output transmission spur gear 254b includes 10 teeth; second input transmission spur gear 256a includes 20 teeth; second output transmission spur gear 256b includes 10 teeth; and second output drive shaft spur gear 258b includes 15 teeth. As so configured, an input rotation of second input drive shaft 226a is converted to an output rotation of second output drive shaft 258a by a ratio of 1:6.

As mentioned above, a proximal end of second input drive shaft 226a is configured to support second connector sleeve 220.

In operation, as second input drive shaft spur gear 252a is rotated, due to a rotation of second connector sleeve 260 and second input drive shaft 226a, as a result of the rotation of the second respective drive connector 120 of surgical instrument 100, second input drive shaft spur gear 252a engages first input transmission spur gear 254a causing first input transmission spur gear 254a to rotate. As first input transmission spur gear 254a rotates, first transmission shaft 254 is rotated and thus causes first output transmission spur gear 254b, that is keyed to first transmission shaft 254, to rotate. As first output transmission spur gear 254b rotates, since second input transmission spur gear 256a is engaged therewith, second input transmission spur gear 256a is also rotated. As second input transmission spur gear 256a rotates, second transmission shaft 256 is rotated and thus causes second output transmission spur gear 256b, that is keyed to second transmission shaft 256, to rotate. As second output transmission spur gear 256b rotates, since second output drive shaft spur gear 258b is engaged therewith, second output drive shaft spur gear 258b is rotated. As second output drive shaft spur gear 258b rotates, since second output drive shaft spur gear 258b is keyed to second output drive shaft 258a, second output drive shaft 258a is rotated.

As will be discussed in greater detail below, shaft assembly 200, including second gear train system 250, functions to transmit operative forces from surgical instrument 100 to end effector 400 in order rotate shaft assembly 200 and/or end effector 400 relative to surgical instrument 100.

As mentioned above and as seen in FIGS. 5 and 8, transmission housing 212 and shaft coupling assembly 214 rotatably support a third drive shaft 228. Third drive shaft 228 includes a proximal end 228a configured to support third connector sleeve 222, and a distal end 228b extending to and operatively connected to an articulation assembly 270 as will be discussed in greater detail below.

As seen in FIG. 4A, elongate, outer tubular body 210 of shaft assembly 200 includes a first half section 211a and a second half section 211b defining at least three longitudinally extending channels through outer tubular body 210 when half sections 211a, 211b are mated with one another. The channels are configured and dimensioned to rotatably receive and support first output drive shaft 246a, second output drive shaft 258a, and third drive shaft 228 as first output drive shaft 246a, second output drive shaft 258a, and third drive shaft 228 extend from transmission housing 212 to articulating neck assembly 230. Each of first output drive shaft 246a, second output drive shaft 258a, and third drive shaft 228 are elongate and sufficiently rigid to transmit rotational forces from transmission housing 220 to articulating neck assembly 230.

Figure 4B:
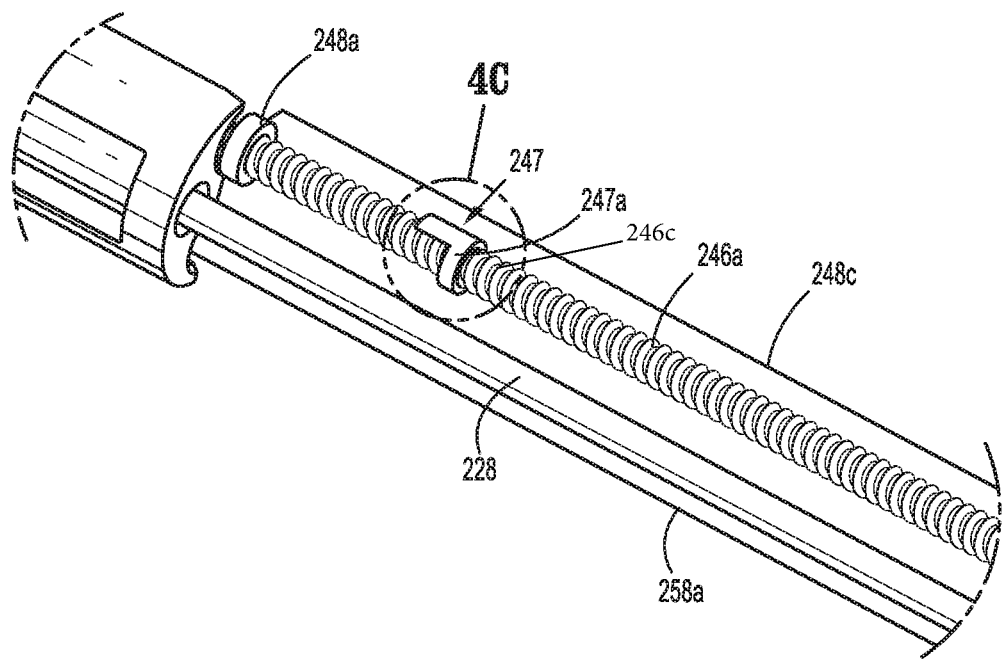
FIG. 4B is an enlarged view of the indicated area of detail of FIG. 4A.
Figure 4C:
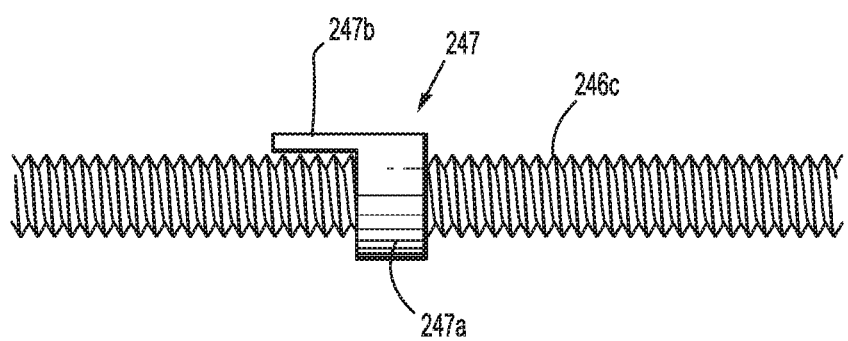
FIG. 4C is an enlarged view of the indicated area of detail of FIG. 4B.

Turning to FIGS. 4A-4C, a distal portion 246c of first drive shaft 246a is threaded. Disposed about the threaded distal portion is a flag member 247 which includes an internally threaded nut 247a and a post 247b. When half sections 211a and 211b of shaft assembly 200 are mated with each other, a channel 247c is formed or defined therein that is configured to receive post 247b. Channel 247c prevents rotation of the flag member 247. Thus, when first drive shaft 246a is rotated, flag member 247 is prevented from rotating, and in turn, is axially translated along the first drive shaft 246a. Flag member 247 is configured to indicate an end stop of end effector 400 as will be described below.

A sensor 248a is mounted on the first drive shaft 264a and disposed distally from flag member 247. When half sections 211a and 211b of shaft assembly 200 are mated with each other, a channel 248b is formed that accommodates sensor 248a and prevents axial movement of sensor 248a. Sensor 248a is a highly poled piezo crystal in the shape of a disk or ring. In alternative embodiments, sensor 248a may be a stack of highly poled piezo crystals. Highly poled piezo crystals are known to provide higher signals than ordinary piezo crystal.

During operation of the powered surgical instrument 100, as the forces remain steady during firing or other actions, the sensor 248a provides little or low electrical signals. As first drive shaft 246a is rotated, flag member 247 is advanced distally. When flag member 247 contacts sensor 248, the forces generated by such contact rise rapidly, causing a high electrical signal to be generated by sensor 248 and transmitted to a controller 502 (see FIG. 50) via conduit 248c.

Turning now to FIGS. 4A and 9-16, articulating neck assembly 230 is shown and described. Articulating neck assembly 230 includes a proximal neck housing 232, a plurality of links 234 connected to and extending in series from proximal neck housing 232; and a distal neck housing 236 connected to and extending from a distal-most link of the plurality of links 234.

Each link 234 includes cooperating knuckles and devises formed on each of a proximal surface 234a and a distal surface 234b thereof. Proximal neck housing 232 includes knuckles and/or devises that operatively engage with the knuckles and/or devises of a proximal-most link. Distal neck housing 236 includes knuckles and/or clevises that operatively engage with the knuckles and/or devises of a distal-most link. The knuckles and devises of adjacent neck housings 232, 236 and links 234 operatively engage with one another to define a direction and a degree of articulation of neck assembly 230.

Neck assembly 230 is configured to enable end effector 400 to move between a substantially linear configuration and a substantially angled, off-axis or articulated configuration. In accordance with the present disclosure, it is contemplated that neck assembly 230 is capable of articulating in a single plane and is capable of articulating approximately 90°, and even greater than 90°.

Figure 12:
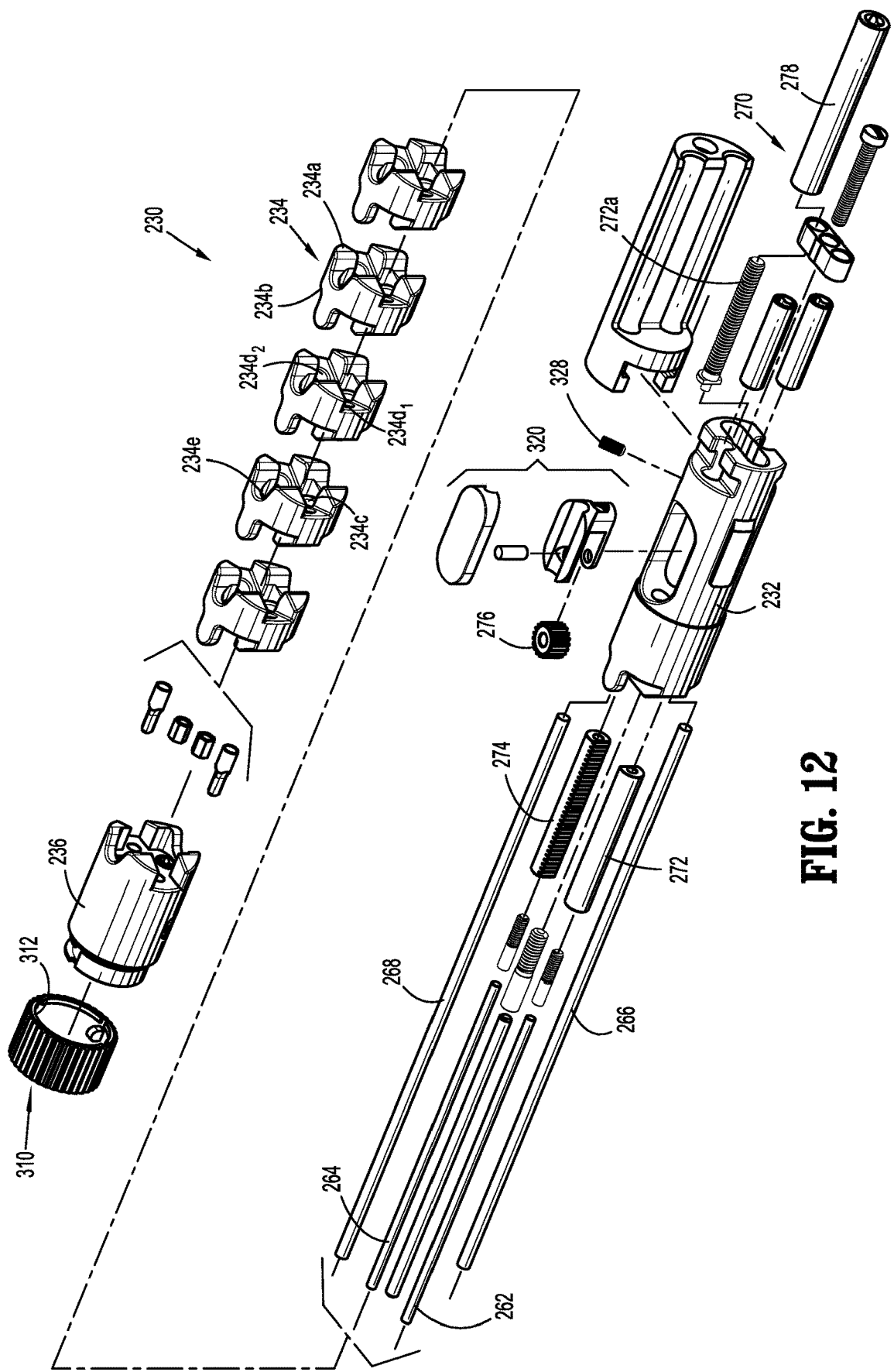
FIG. 12 is a perspective view, with parts separated, of the neck assembly of FIGS. 9-11.

Each link 234 defines a first lumen 234c (see FIG. 12) therein for passage of a first drive cable 266 therethrough; a first pair of opposed lumens $234d_1$, $234d_2$, for passage of a pair of articulation cables 262, 264 therethrough; and a second lumen 234e for passage of a second drive cable 268 therethrough. As seen in FIG. 12, first and second lumens 234c, 234e are diametrically opposed to one another and offset 90° relative to lumens $234d_1$, $234d_2$. Each of first drive cable 266 and second drive cable 268 includes a proximal end keyed to a distal end of respective first output drive shaft 246a and second output drive shaft 258a. Each of first and second drive cables 266, 268 is fabricated from a material that is both flexible and torsionally stiff (capable of transmitting rotational forces or torque), such as, for example, stainless steel and the like.

As seen in FIGS. 13-16, proximal neck housing 232 of neck assembly 230 supports an articulation assembly 270 configured and adapted to impart articulation to neck assembly 230 and/or end effector 400. Articulation assembly 270 includes a pair of opposed gear racks 272, 274 engaged with and on opposed sides of a pinion gear 276. Racks 272, 274 are axially slidably supported in proximal neck housing 232 and pinion gear 276 is rotatably supported in proximal neck housing 232.

Figure 13:
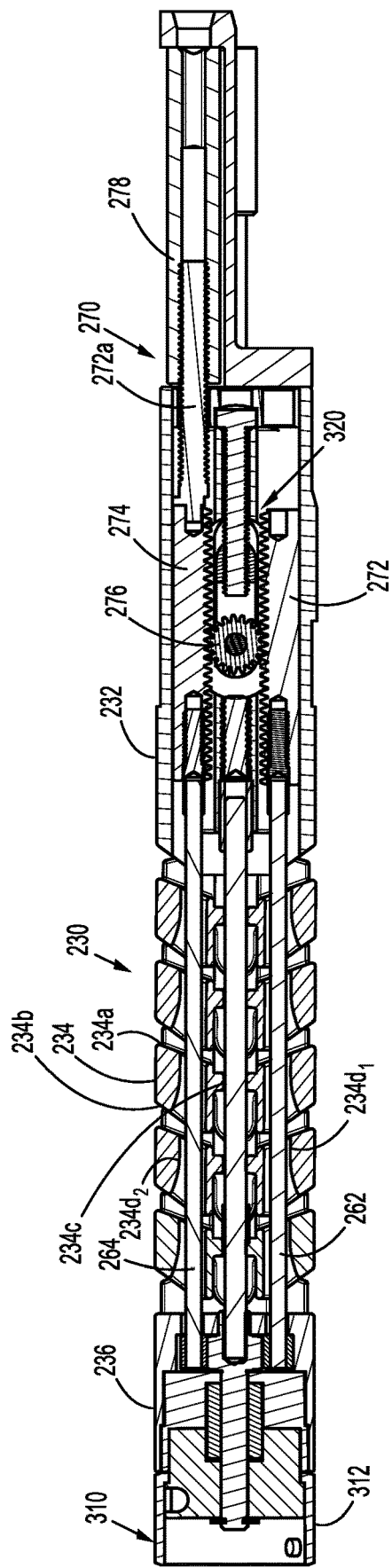
FIG. 13 is a cross-sectional view of the neck assembly of FIGS. 9-12, as taken through 13-13 of FIG. 9.
Figure 14:
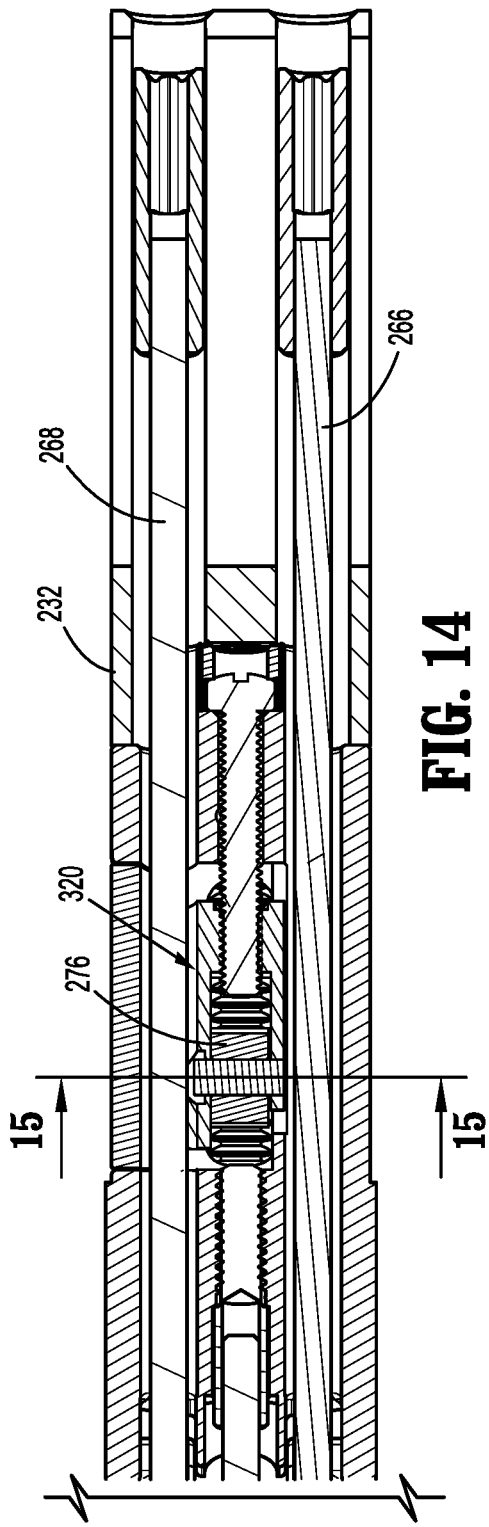
FIG. 14 is a cross-sectional view of the neck assembly of FIGS. 9-12, as taken through 14-14 of FIG. 10.
Figure 15:
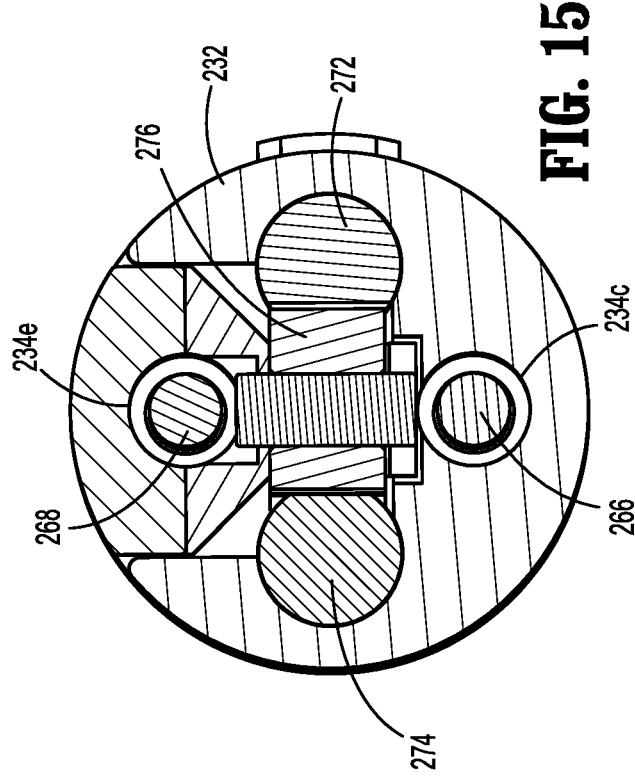
FIG. 15 is a cross-sectional view of the neck assembly of FIGS. 9-12, as taken through 15-15 of FIG. 14.
Figure 17:
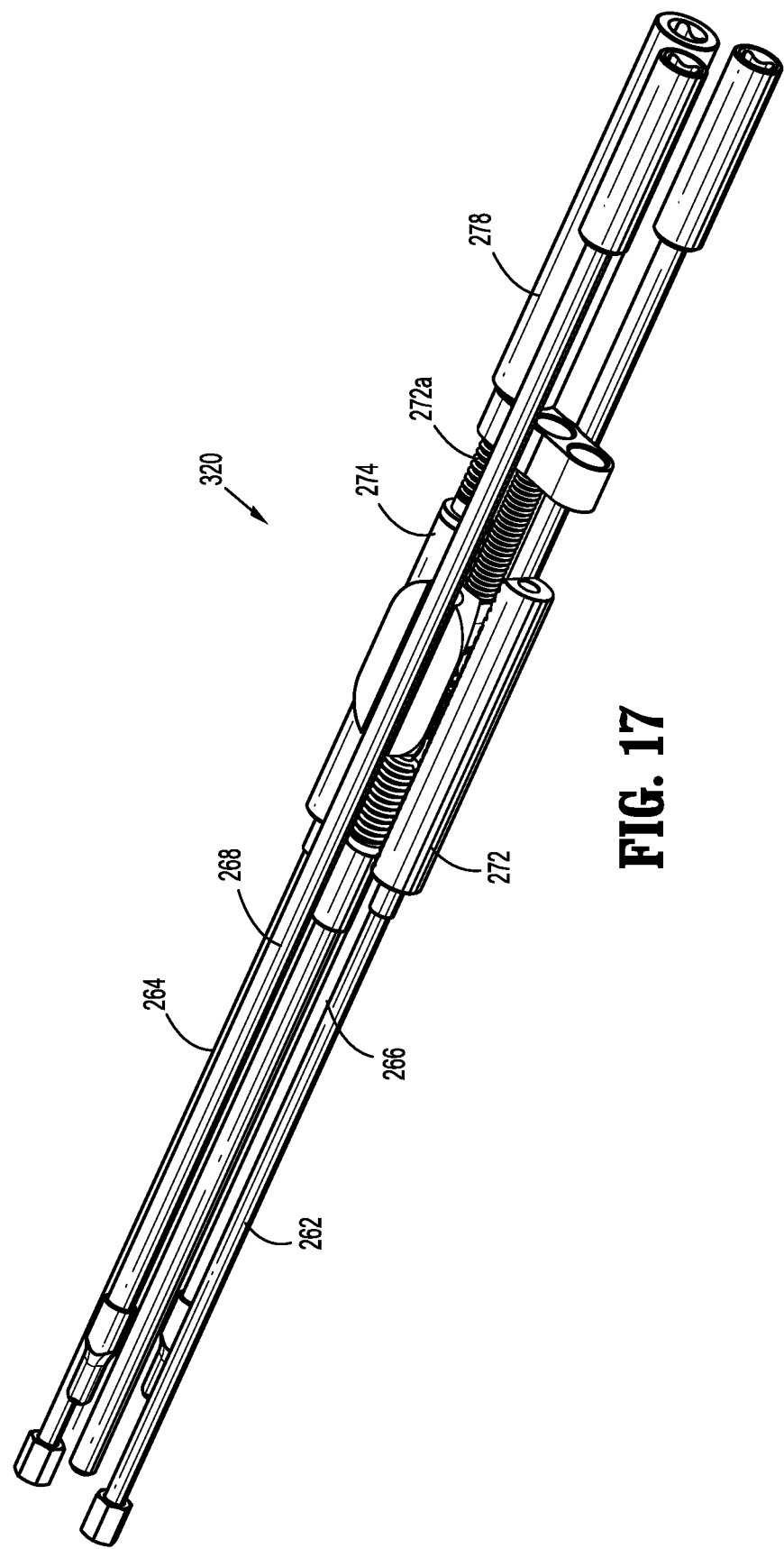
FIG. 17 is a perspective view of an articulation assembly.
Figure 18:
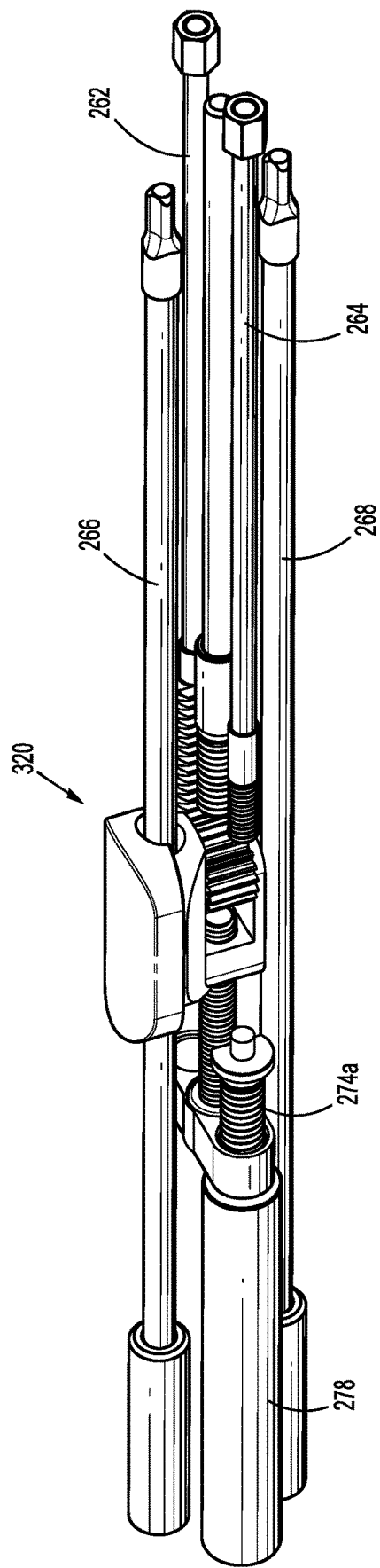
FIG. 18 is a further perspective view of the articulation assembly of FIG. 17.
Figure 19:
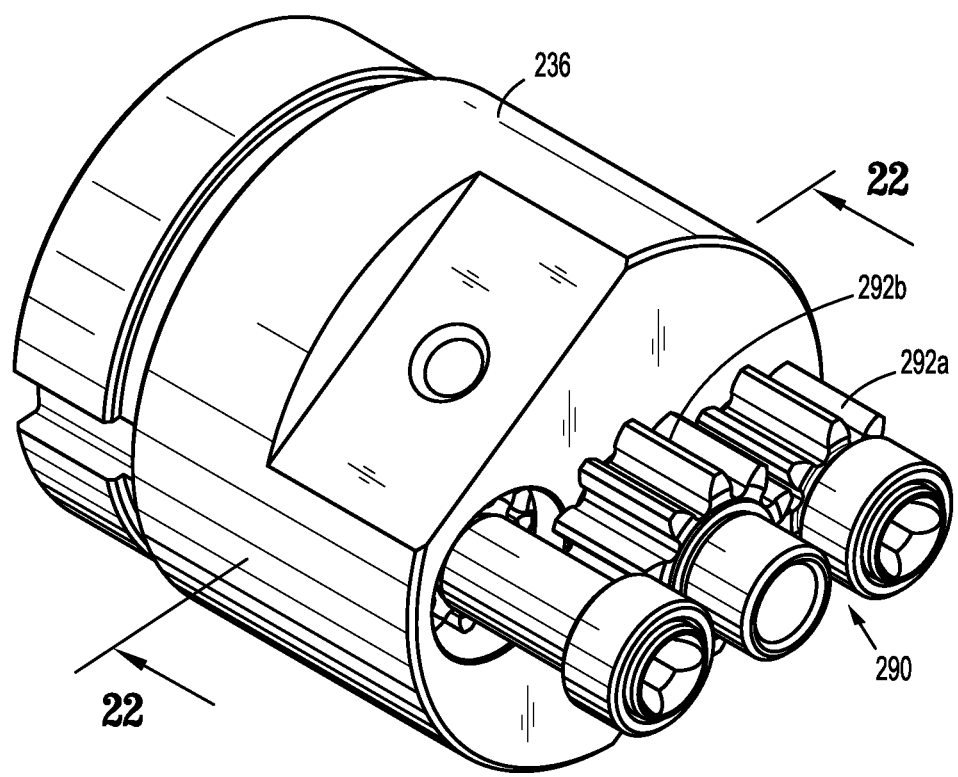
FIG. 19 is a perspective view of a second gear train that is supported in a distal neck housing of the neck assembly.
Figure 20:
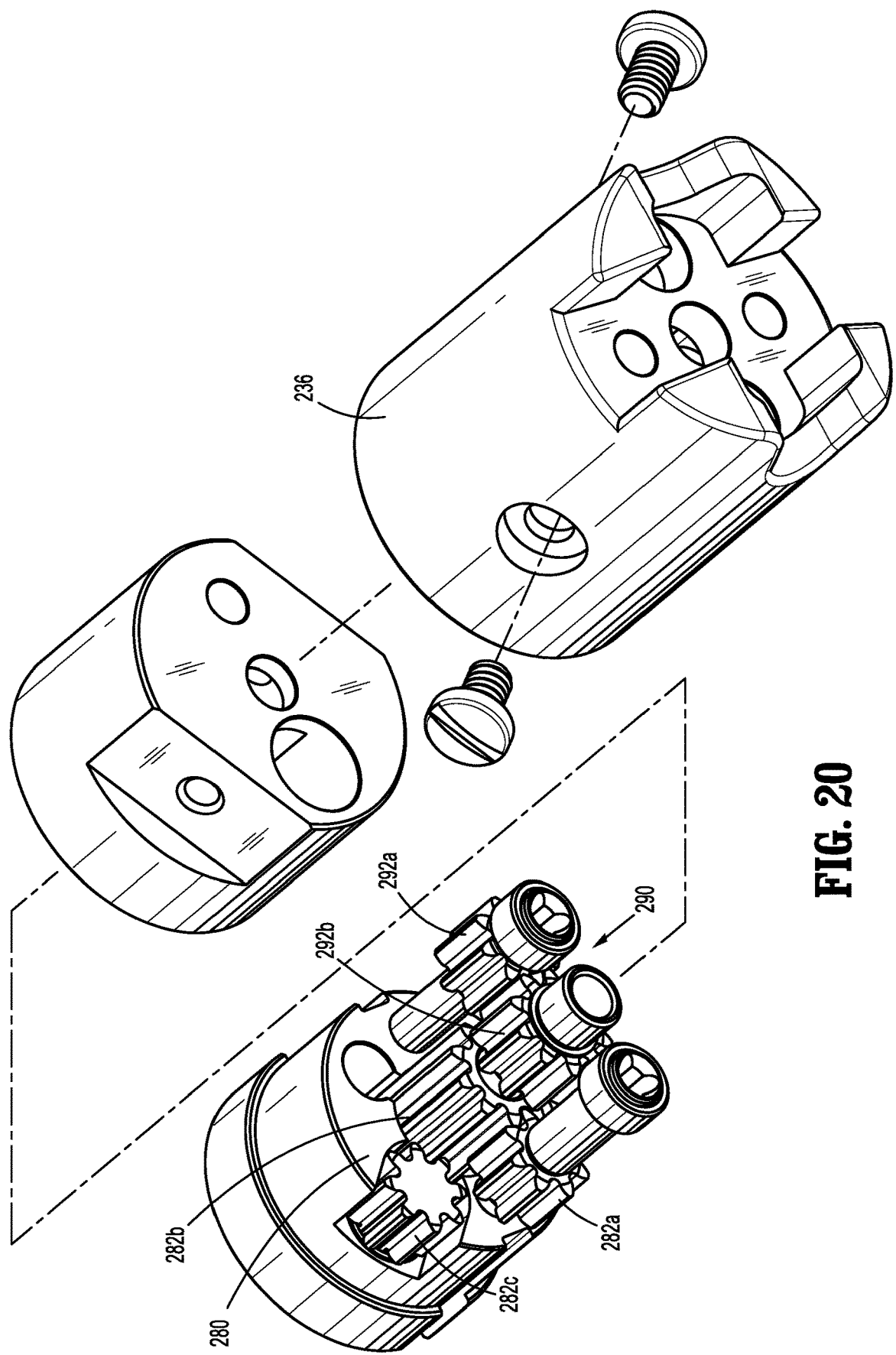
FIG. 20 is a perspective view, with parts partially separated, of a first gear train and the second gear train that are supported in a distal neck housing of the neck assembly.
Figure 21:
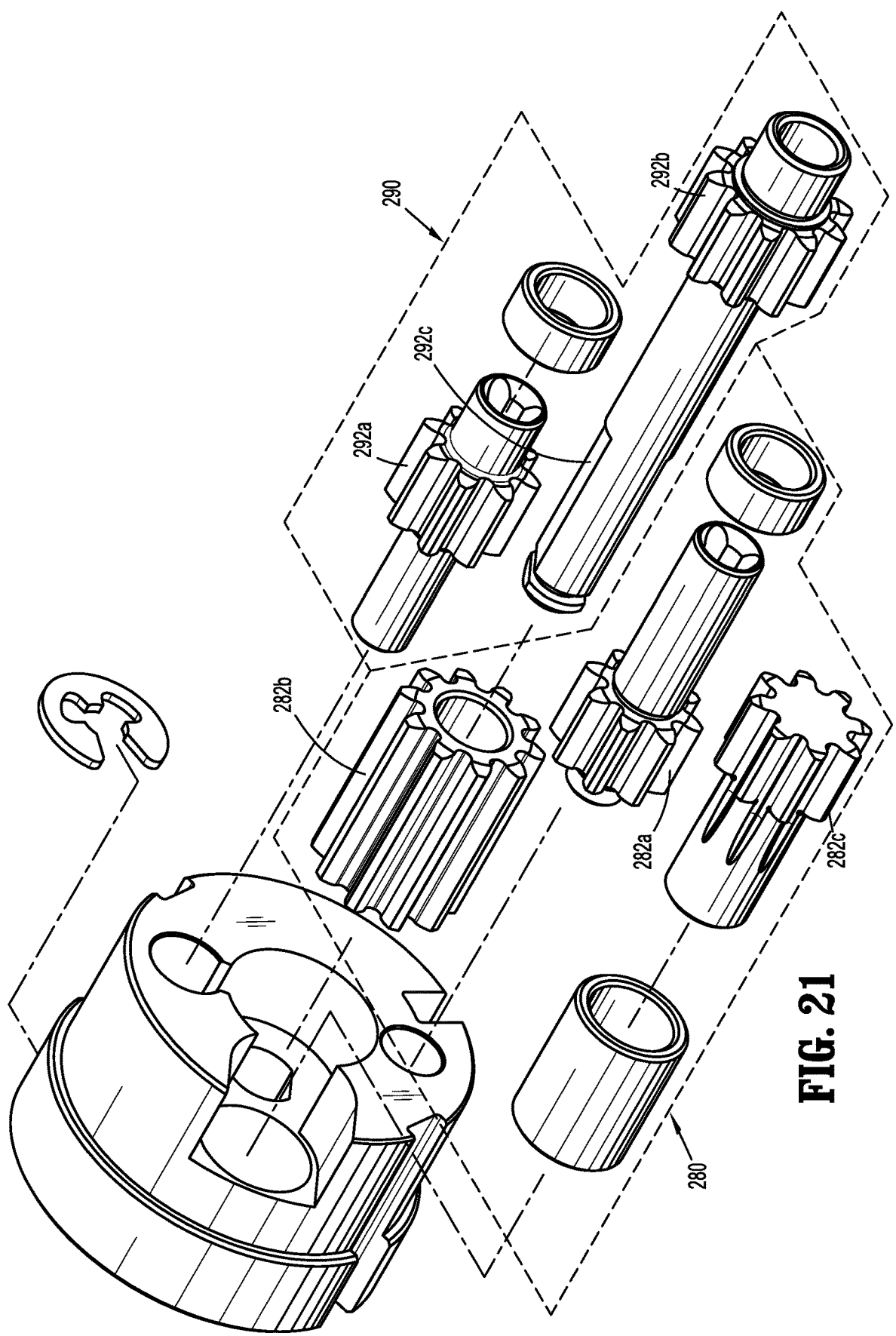
FIG. 21 is a perspective view, with parts partially separated, of the first gear train and the second gear train that are supported in a distal neck housing of the neck assembly.
Figure 24:
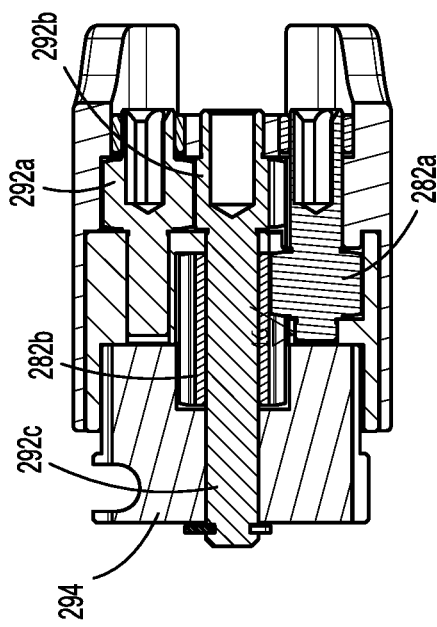
FIG. 24 is a cross-sectional view of the distal neck housing, as taken through 24-24 of FIG. 22.
Figure 25:
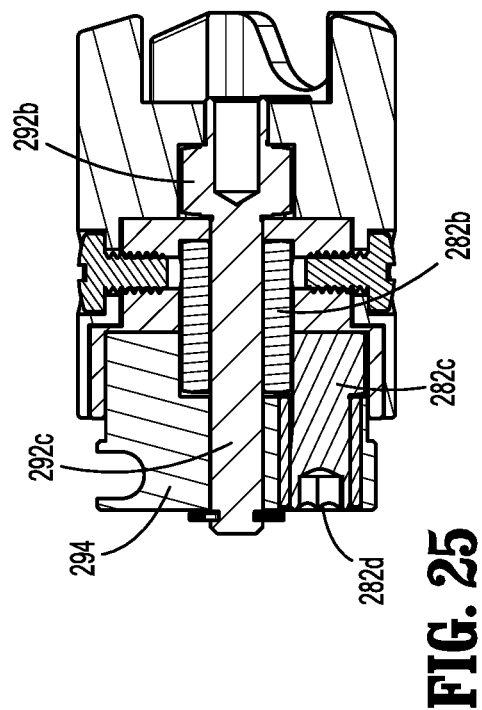
FIG. 25 is a cross-sectional view of the distal neck housing, as taken through 25-25 of FIG. 22.
Figure 23:
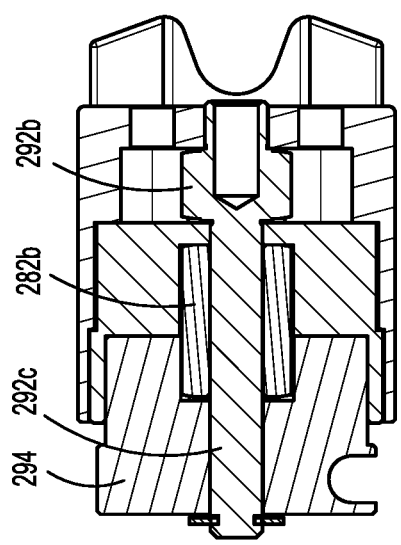
FIG. 23 is a cross-sectional view of the distal neck housing, as taken through 23-23 of FIG. 22.
Figure 22:
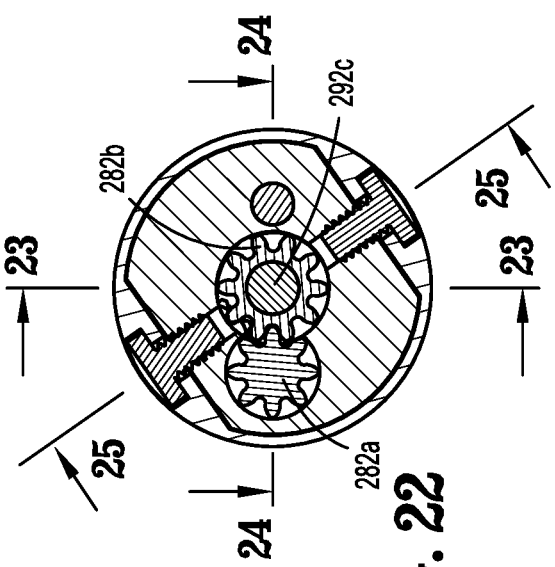
FIG. 22 is a cross-sectional view of the distal neck housing, as taken through 22-22 of FIG. 19.

As seen in FIGS. 12, 13 and 17, rack 274 is attached to a threaded shaft 272a extending proximally therefrom and that is in threaded engagement with a distal end of an internally threaded nut 278. Threaded nut 278 is rotatably supported and axially fixed within a pocket 232a formed in proximal neck housing 232. A proximal end of threaded nut 278 is keyed to a distal end of third drive shaft 228. While threaded shaft 272a is shown extending from rack 274, it is understood, and within the scope of the present disclosure, that the threaded shaft may extend from rack 272 without departing from the principles of the present disclosure.

Articulation cables 262, 264 include proximal ends that are secured to and extend from a respective distal end of racks 272, 274. Each articulation cable 262, 264 includes a distal end that extends through respective opposed lumens $234d_1$, $234d_2$ of links 234 and that is secured to or anchored in distal neck housing 234.

Figure 16:
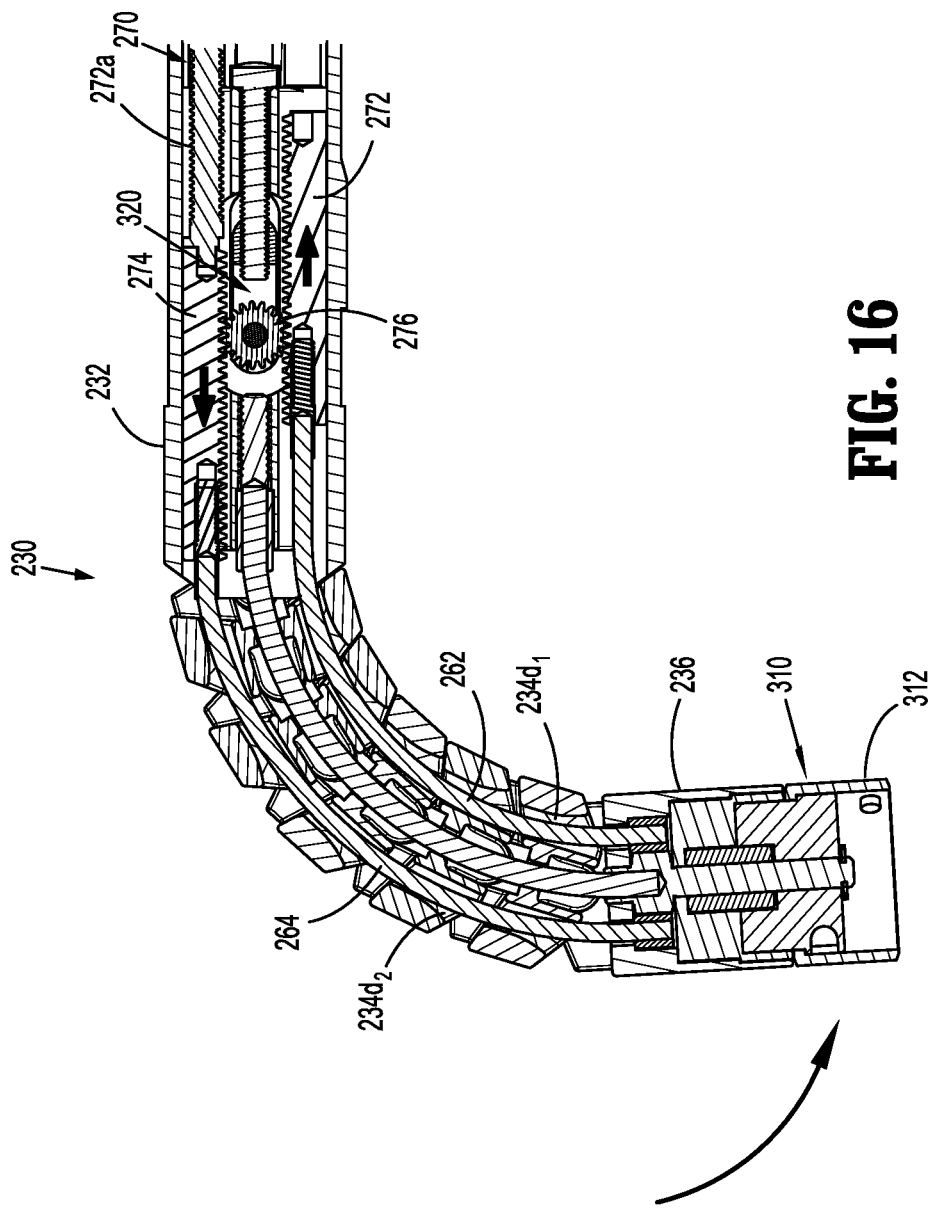
FIG. 16 is an illustration of the neck assembly of FIG. 13, shown in an articulated condition.

In operation, to articulate neck assembly 230 in a first direction, third drive shaft 228 is rotated in a first direction, as described above, to rotate threaded nut 278 and axially displace threaded shaft 272a distally to axially displace rack 274 distally (see FIG. 16). As rack 274 is displaced axially, in a distal direction, rack 274 causes pinion gear 276 to be rotated and to thus act on rack 272, to axially displace rack 272 in a proximal direction. As rack 272 is axially displaced in a proximal direction, rack 272 causes articulation cable 262 to be drawn in a proximal direction and thereby articulate neck assembly 230, as illustrated in FIG. 16. Neck assembly 230 is permitted to articulate since axially displacement of rack 274, in a distal direction, results in axial, distal displacement of articulation cable 264.

Distal neck housing 236 supports a first gear train 280 and a second gear train 290. First gear train 280 functions to transmit a rotation of first drive cable 266 to end effector 400. Second gear train 290 functions to transmit a rotation of second drive cable 268 to end effector 400.

As seen in FIGS. 20-25, first gear train 280 of distal neck housing 236 includes a first spur gear 282a rotatably supported in distal neck housing 236 and keyed to a distal end of first drive cable 266 of shaft assembly 200. First gear train 280 of distal neck housing 236 further includes a second spur gear 282b rotatably supported in distal neck housing 236 and engaged with first spur gear 282a. First gear train 280 of distal neck housing 236 also includes a third spur gear 282c rotatably supported in distal neck housing 236 and engaged with second spur gear 282b.

Figure 26:
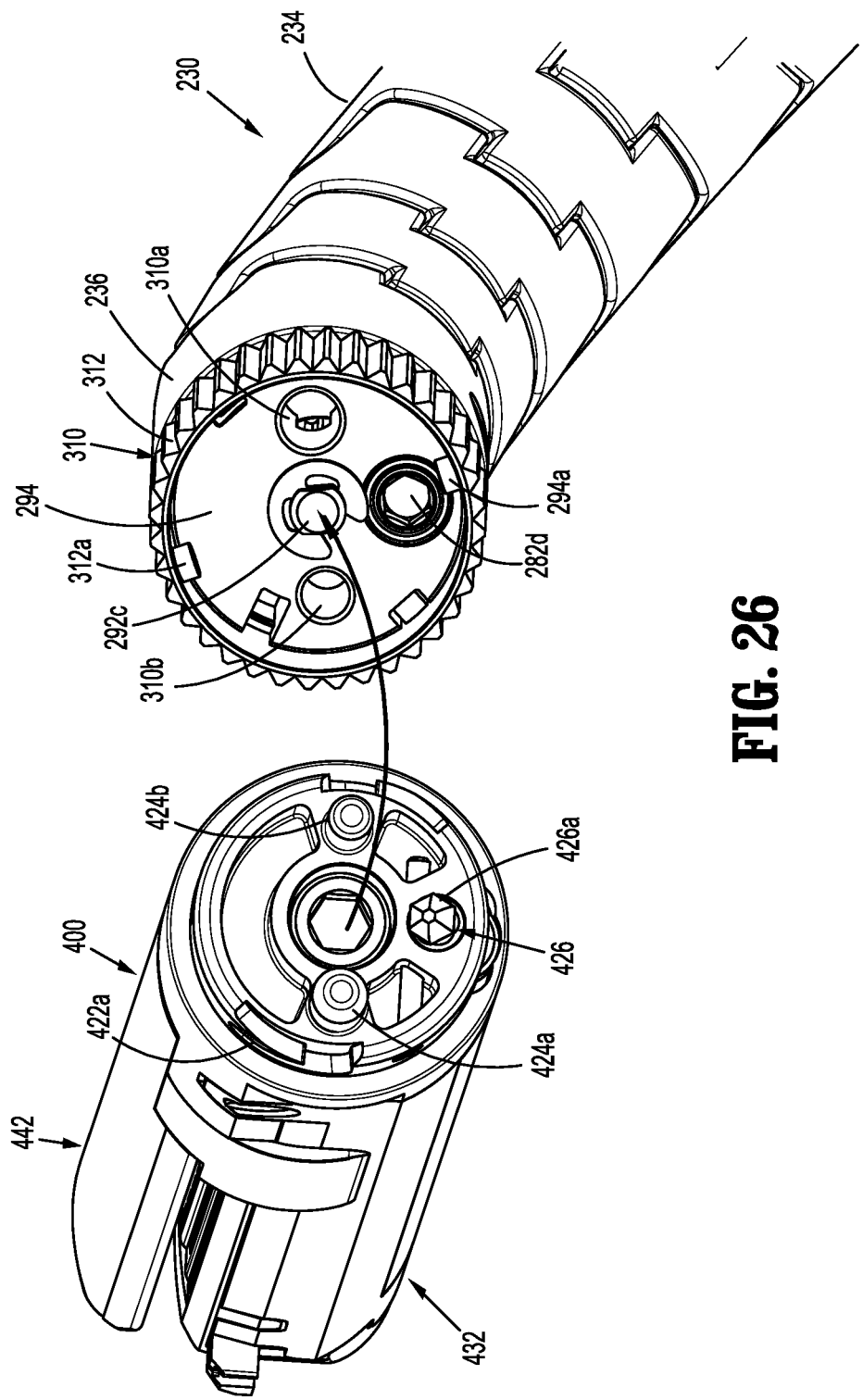
FIG. 26 is a rear, perspective view of the shaft assembly and an end effector, of the electromechanical surgical system of FIGS. 1 and 2, illustrating a connection therebetween.

Third spur gear 282c includes a bore 282d formed along a central axis thereof that is configured for mating receipt of a drive axle 426 of end effector 400 (see FIG. 26).

In accordance with the present disclosure, first spur gear 282a includes 8 teeth; second spur gear 282b includes 10 teeth; and third spur gear 282c includes 8 teeth. As so configured, an input rotation of first drive cable 266 is converted to an output rotation of third spur gear 282c of distal neck housing 236 by a ratio of 1:1. Additionally, first gear train 280 is provided to rotatably and mechanically connect first drive cable 266 to drive axle 426 of end effector 400.

In operation, as first drive cable 266 is rotated, due to a rotation of first output drive shaft 246a (as described above), said rotation is transmitted to first spur gear 282a of first gear train 280. As first spur gear 282a is rotated, third spur gear 282c is rotated due to the inter-engagement of first spur gear 282a and third spur gear 282c by second spur gear 282b. As third spur gear 282c is rotated, when end effector 400 is connected to shaft assembly 200, and specifically, third spur gear 282c is connected to drive axle 426 of end effector 400, a rotation of third spur gear 282c results in rotation of drive axle 426 of end effector 400 and actuation of end effector 400.

As seen in FIGS. 20-25, second gear train 290 of distal neck housing 236 includes a first spur gear 292a rotatably supported in distal neck housing 236 and keyed to a distal end of second drive cable 268 of shaft assembly 200. Second gear train 290 of distal neck housing 236 further includes a second spur gear 292b rotatably supported in distal neck housing 236 and engaged with first spur gear 292a. Second gear train 290 of distal neck housing 236 also includes a non-circular shaft 292c extending from second spur gear 292b (see FIG. 21). Non-circular shaft 292c is keyed to a rotation hub 294 such that rotation of non-circular shaft 292c results in rotation of rotation hub 294.

Rotation hub 294 is provided between a shaft of third spur gear 282c, of first gear train 280, that defines the bore 282d thereof and rotation hub 294 transmitting relative rotation of third spur gear 282c of first gear train 280 to rotation hub 294 of second gear train 290.

In accordance with the present disclosure, first spur gear 292a includes 8 teeth (which functions as the input); and second spur gear 292b includes 10 teeth. As so configured, an input rotation of second drive cable 268 is converted to an output rotation of rotation hub 294. The gear ratio for this is 1:0.8. Additionally, second gear train 290 is provided to rotatably and mechanically connect second drive cable 268 to rotation hub 294 of distal neck housing 236 of neck assembly 230.

In operation, as second drive cable 268 of shaft assembly 200 is rotated, due to a rotation of second output drive shaft 258a (as described above), said rotation is transmitted to first spur gear 292a of first gear train 290. As first spur gear 292a is rotated, non-circular shaft 292c is rotated due to its connection with second spur gear 292b. As non-circular shaft 292c is rotated, when end effector 400 is connected to shaft assembly 200, and specifically, rotation hub 294 is connected to alignment stems 424a, 424b of end effector 400, a rotation of rotation hub 294 results in rotation of end effector 400.

Shaft assembly 200 further includes an end effector coupling assembly 310 supported at a distal end of distal neck housing 236 of articulating neck assembly 230. End effector coupling assembly 310 includes a collar 312 rotatably supported on and extending distally from distal neck housing 236 and being biased to a first radial portion. Collar 312 is rotatable from a first radial position to a second radial position, wherein end effector 400 is matable to end effector coupling assembly 310, and returns, by way of the bias, to the first radial position, to lock end effector 400 to shaft assembly 200.

It is contemplated that collar 312 includes at least one nub 312a extending radially inward from inner surface thereof for receipt in a respective complementary structure 422a formed in an outer surface of end effector 400 to connect end effector 400 to shaft assembly 200 in the manner of a bayonet-type connection. Other forms of connection are contemplated, such as, detents, threaded connections, etc.

As seen in FIGS. 12-14, 17 and 18, shaft assembly 200 includes a cable tensioning assembly 320. Cable tensioning assembly 320 includes a clevis 322 slidably supported in proximal neck housing 232, for axial displacement therewithin. Clevis 322 rotatably supports pinion gear 276 of articulation assembly 270. Cable tensioning assembly 320 includes an adjustment screw 324, rotatably supported in proximal neck housing 232 and retained against axial displacement. Adjustment screw 324 is threadably connected to clevis 322 such that rotation of adjustment screw 324 results in axial displacement of clevis 322.

In operation, during an assembly of shaft assembly 200, an operator rotates adjustment screw 324 in a direction so as to axially displace clevis 322 in a proximal direction. As clevis 322 is axially displaced, in a proximal direction, clevis 322 pulls on pinion gear 276 of articulation assembly 270. As pinion gear 276 is axially displaced, in a proximal direction, pinion gear 276 acts on racks 272, 274 to draw racks 272, 274 in a proximal direction. As racks 272, 274 are drawn in a proximal direction, with articulation cables 262, 264 respectively connected thereto, and with distal ends of articulation cables 262, 264 fixed or anchored in place, articulation cables 262, 264 are caused to be tensioned. It is contemplated that a set screw 328 (see FIG. 12) may be provided to fix the position of adjustment screw 324 and help to maintain articulation cables 262, 264 tensioned.

It is contemplated that over time and/or following a number of uses, that an end user of shaft assembly 200 may be able to access adjustment screw 324 and re-tension articulation cables 262, 264 as needed or necessary.

Turning now to FIGS. 26-49, end effector 400 is shown and described. End effector 400 is configured and adapted to apply a plurality of linear rows of fasteners 433. In certain embodiments, the fasteners are of various sizes, and, in certain embodiments, the fasteners have various lengths or rows, e.g., about 30, 45 and 60 mm in length.

Figure 27:
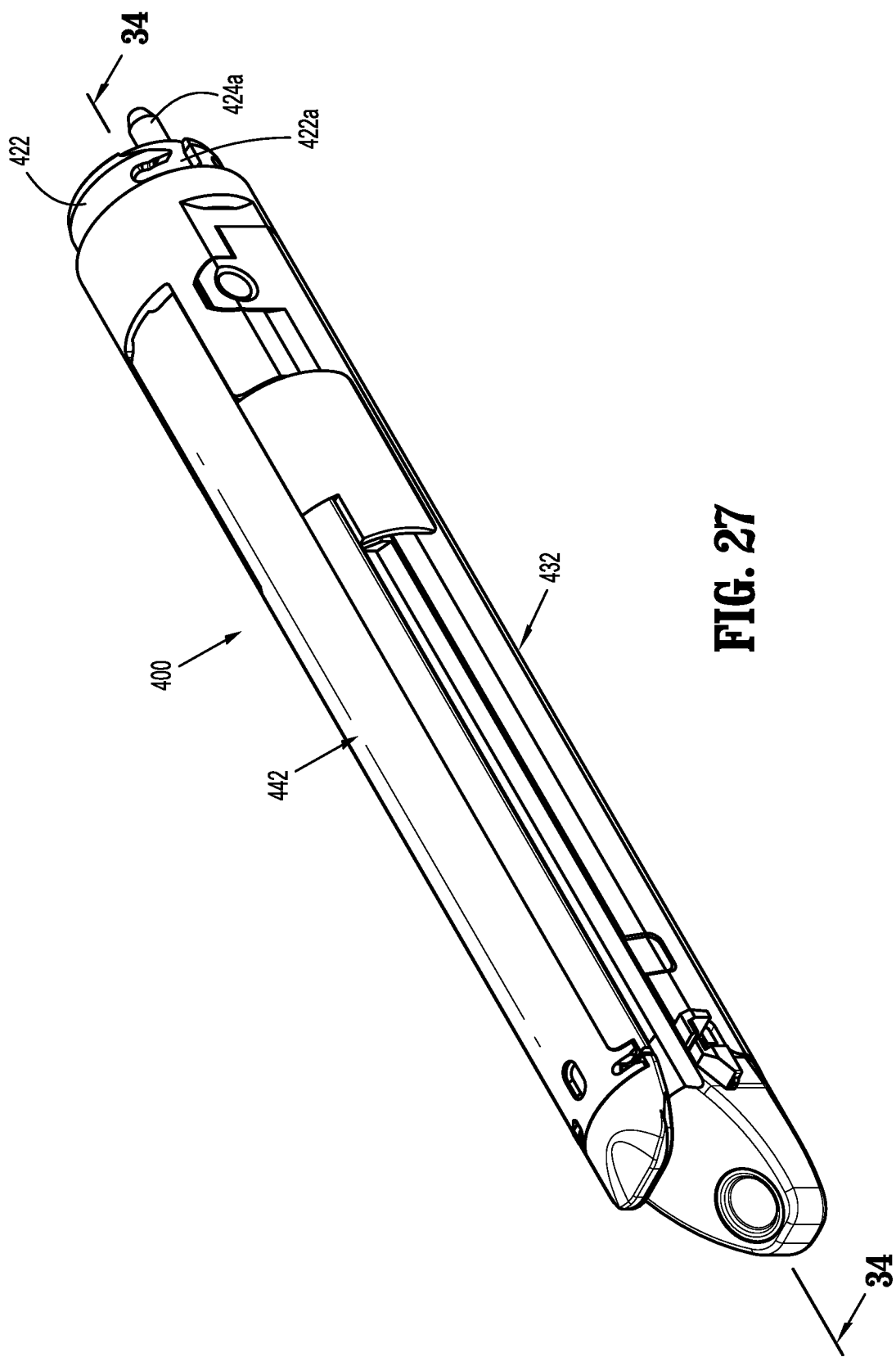
FIG. 27 is a perspective view of the end effector, shown in a closed condition.
Figure 28:
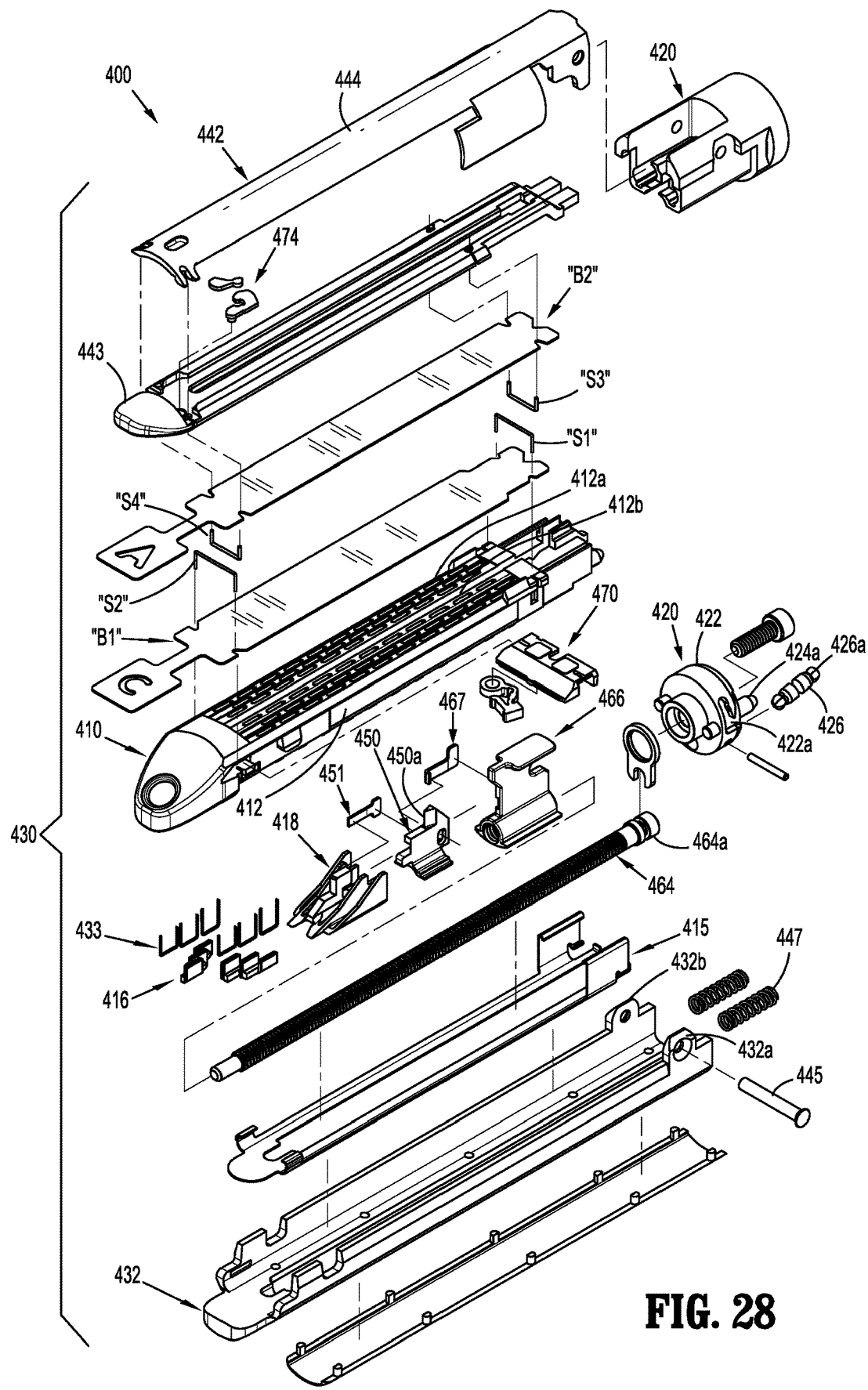
FIG. 28 is a perspective view, with parts separated, of the end effector of FIG. 27.
Figure 29:
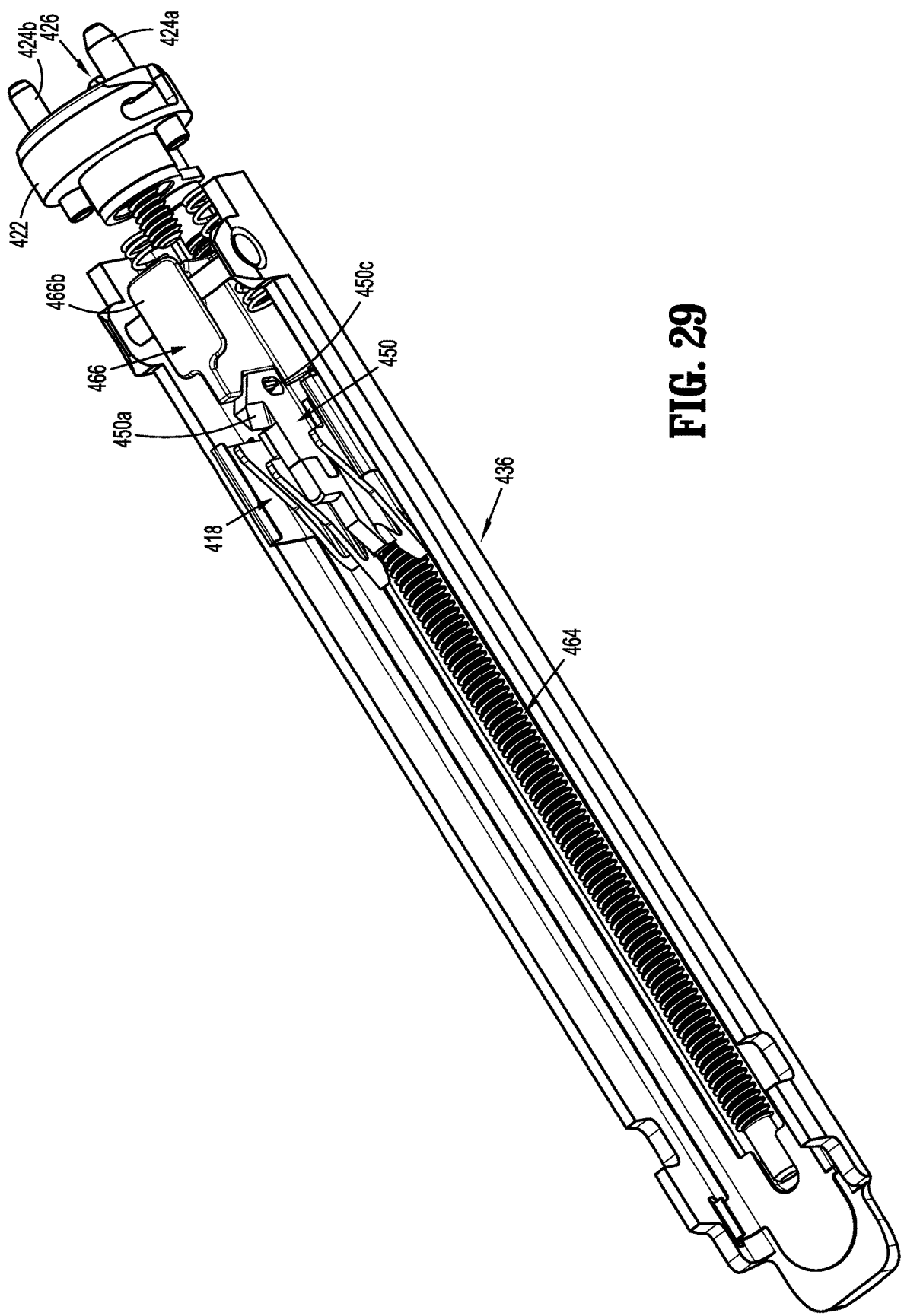
FIG. 29 is a perspective view of a lower jaw of the end effector of FIGS. 27 and 28.
Figure 30:
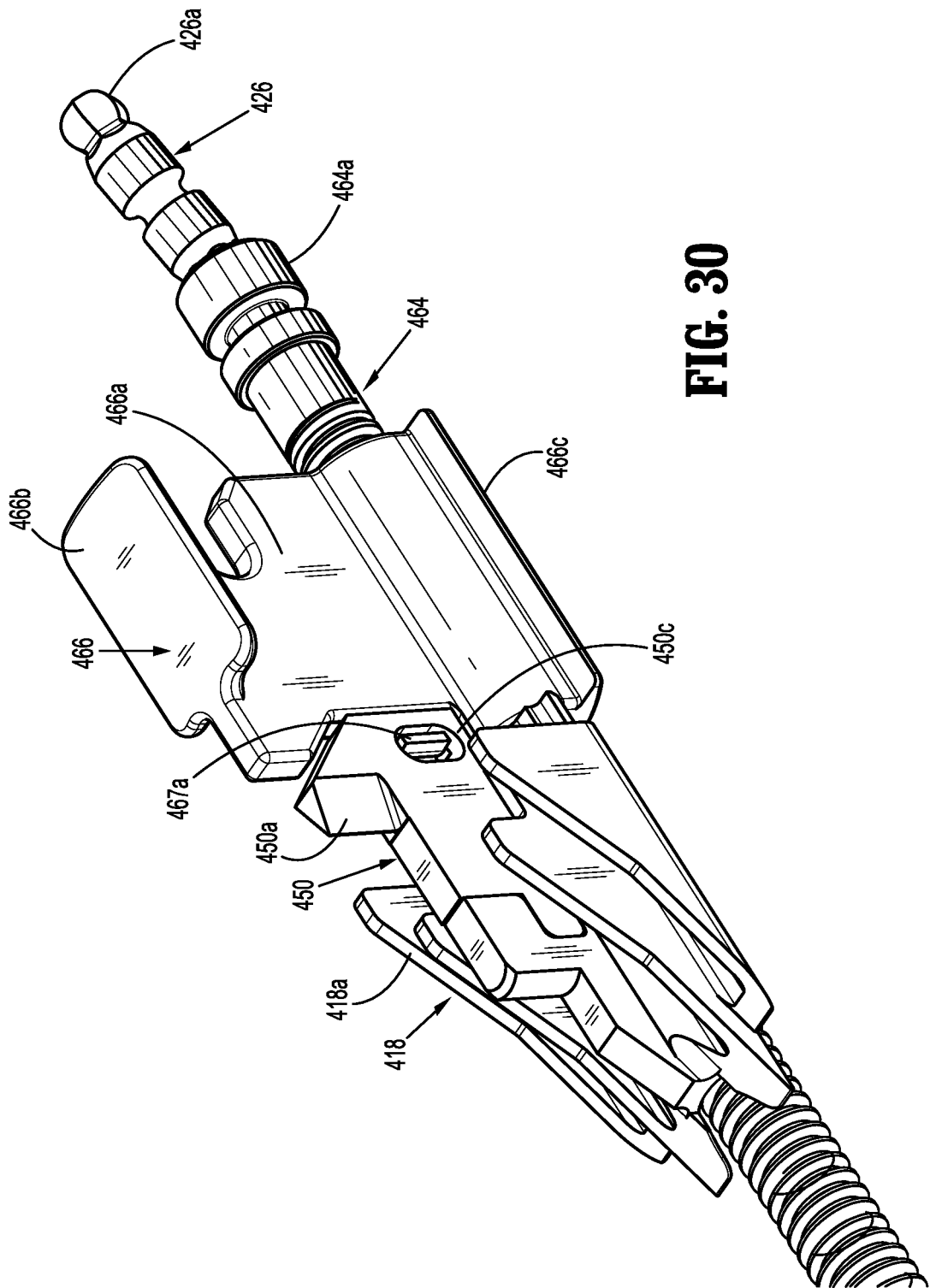
FIG. 30 is a perspective view of a drive beam, a knife sled and an actuation sled of the end effector of FIGS. 27-29.
Figure 31:
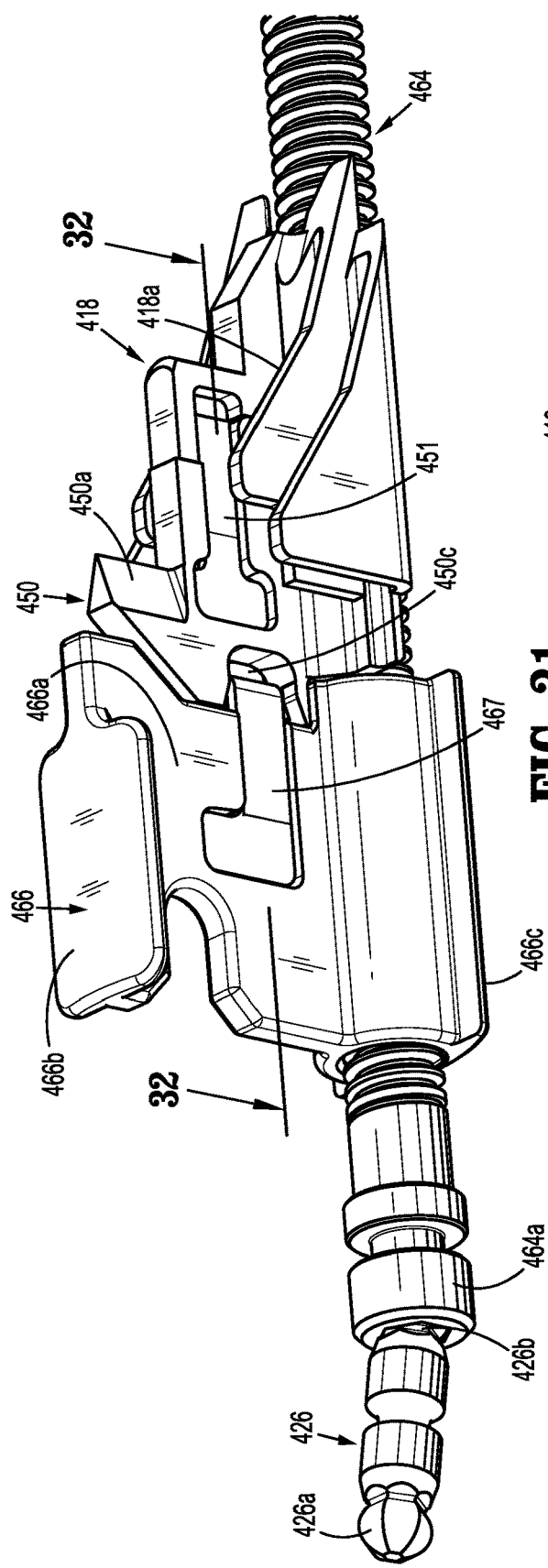
FIG. 31 is a further perspective view of the drive beam, the knife sled and the actuation sled of the end effector of FIGS. 27-29.
Figure 32:
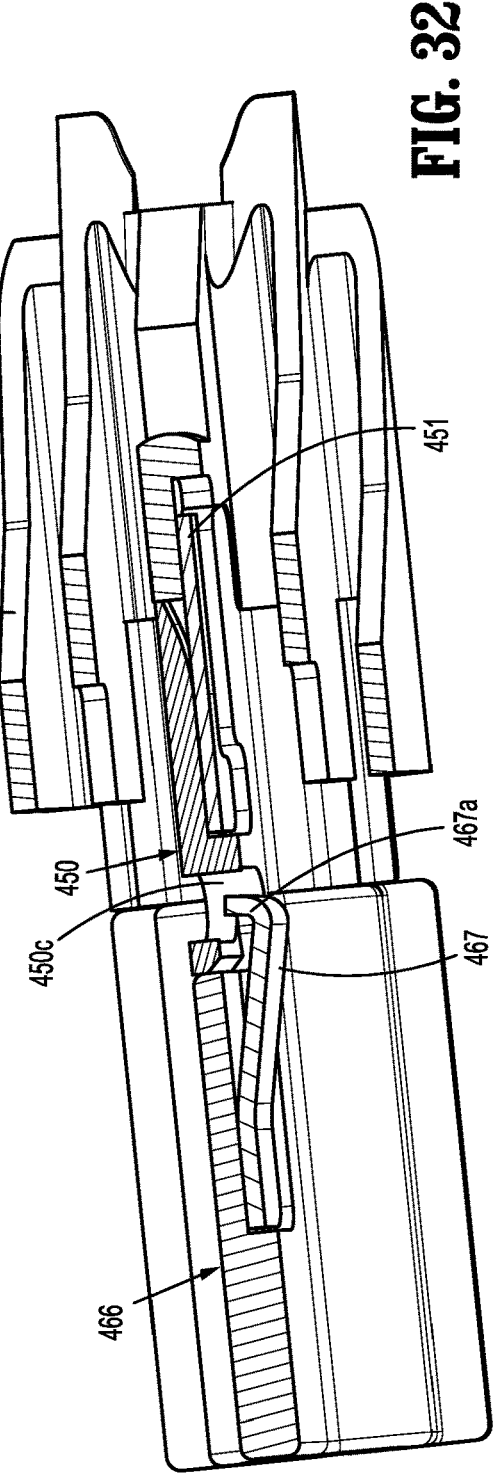
FIG. 32 is a cross-sectional view as taken through 32-32 of FIG. 31.

As seen in FIGS. 26-28, end effector 400 includes a mounting portion 420 (FIG. 28) configured for selective connection to end effector coupling assembly 310 of shaft assembly 200. End effector 400 further includes a jaw assembly 430 connected to and extending distally from mounting portion 420. Jaw assembly 430, as will be discussed in greater detail below, includes a lower jaw 432 pivotally connected to mounting portion 420 and being configured to selectively support a cartridge assembly 410 therein, and an upper jaw 442 secured to mounting portion 420 and being movable, relative to lower jaw 432, between approximated and spaced apart positions.

As seen in FIGS. 26-28, mounting portion 420 includes a coupling member 422 secured to a proximal end thereof. Coupling member 422 defines a substantially J-shaped channel 422a (see FIGS. 26-28) formed in a radial outer surface thereof that is configured and dimensioned for selective connection with complementary structure formed on or extending radially inward from collar 312 of end effector coupling assembly 310, as described above. Coupling member 422 further includes a pair of spaced apart alignment stems 424a, 424b projecting proximally therefrom, for receipt in respective alignment bores 310a, 310b formed in a distal surface of end effector coupling assembly 310.

The alignment stems 424a, 424b along with the alignment bores 310a, 310b are used to align and couple end effector 400 to end effector coupling assembly 310 of shaft assembly 200. The nub 312a of collar 312 and the J-shaped channel 422a of coupling member 422 may define a conventional bayonet-type coupling which facilitates quick and easy engagement and removal of end effector 400 from shaft assembly 200 before, during or after a surgical procedure.

Mounting portion 420 further includes, as seen in FIGS. 26, 28-31, 34 and 35 a drive axle 426 rotatably supported therein. Drive axle 426 includes a multi-faceted, proximal head 426a projecting proximally from coupling member 422 and being configured for mating engagement with third spur gear 282c of first gear train 280 of distal neck housing 236 and first gear train system 240 of shaft assembly 200, when end effector 400 is coupled to shaft assembly 200. Drive axle 426 further includes multi-faceted, a distal head 426b projecting distally from coupling member 422 and being configured for mating engagement with a threaded drive shaft 464 supported in lower jaw 432 of jaw assembly 430. Drive axle 426 functions to transmit rotational drive forces from third spur gear 282c of first gear train 280 of distal neck housing 236 and of first gear train system 240 of shaft assembly 200, which defines an axis of rotation, to drive screw 464 of lower jaw 432 of jaw assembly 430, which defines an axis of rotation that is different than the axis of rotation of third spur gear 282c.

As seen in FIGS. 28-31, 34-36 and 39-43, lower jaw 432 of jaw assembly 430 includes a drive screw 464 rotatably supported therein and extending substantially an entire length thereof. Drive screw 464 includes a female coupling member 464a supported on a proximal end thereof and being configured for receipt of multi-faceted, distal head 426b of drive axle 426. Drive screw 464 is axially and laterally fixed within lower jaw 432 of jaw assembly 430 by a thrust plate 465, or the like, which is secured to jaw assembly 430 and at least partially extends into an annular channel 464a formed in drive screw 464. In operation, rotation of drive axle 426 results in concomitant rotation of drive screw 464.

As seen in FIGS. 28-43, end effector 400 includes a drive beam 466 slidably supported in lower jaw 432 of jaw assembly 430. Drive beam 466 includes a substantially I-shaped cross-sectional profile and is configured to approximate lower jaw 432 and upper jaw 442, and to axially displace an actuation sled 468 through lower jaw 432. As seen in FIG. 33, drive beam 466 includes a vertically oriented support strut 466a; a lateral projecting member 466b formed atop support strut 466a and being configured to engage and translate with respect to an exterior camming surface of upper jaw 442 to progressively close jaw assembly 430; and a retention foot 466c having an internally threaded bore for threadable connection to threaded drive shaft 464. Since drive beam 466 is prevented from rotation by the engagement of strut 466a and/or cam member 466b with upper jaw 442, as drive screw 464 is rotated, retention foot 466c, and in turn, drive beam 466 is axially translated relative to lower jaw 432.

Drive beam 466 includes a lock clip 467 extending distally from strut 466a. Lock clip 467 defines a hook 467a configured to engage a window 450c formed in a knife sled 450, as will be discussed in greater detail below. Hook 467a of lock clip 467 is biased to extend away from knife sled 450. Prior to firing the cartridge assembly 410, the drive beam 466 is at a proximal-most position in lower jaw 432 and actuation sled 418 and knife sled 450 are at a proximal-most position in cartridge body 412, as seen in FIGS. 36 and 37. Lock clip 467, prior to firing, is disengaged from window 450c of knife sled 450 and extends into a relief 412e defined in a wall of knife slot 412b.

Lower jaw 432 is in the form of a channel and is configured and adapted to selectively receive a disposable staple cartridge assembly 410 therein. Staple cartridge assembly 410 includes a cartridge body 412 defining a plurality of rows of staple retaining slots 412a and a longitudinally extending knife slot 412b disposed between pairs of rows of staple retaining slots 412a. Staple cartridge assembly 410 also includes a plurality of staples 433 disposed, one each, in the plurality of retaining slots 412a. Staple cartridge assembly 410 further includes a plurality of staple pushers 416 supported therein, wherein the staple pushers 416 are aligned one each within retaining slots 412a such that a single staple pusher 416 is positioned under a respective staple 433 which is retained within slot 412a. Staple pushers 416 may be formed such that they are attached to each other in a pusher member having groups of two or three pushers, wherein the pusher member may have offset oriented pushers. One or more actuating surfaces is provided on a lower surface of the pusher member (not shown).

Staple cartridge assembly 410 includes an actuation sled 418 slidably supported against a lower surface of cartridge body 412 and being engageable by drive beam 466. Actuation sled 418 includes upstanding cam wedges 418a configured to exert a driving force on staple pushers 416, by contacting the actuating surfaces, which drives staples 414 from staple cartridge assembly 410, as described in greater detail below.

Cartridge body 412 defines a plurality of spaced apart longitudinal channels 412c (see FIG. 36) extending therethrough to accommodate the upstanding cam wedges 418a of actuation sled 418. Channels 412c communicate with the plurality of retaining slots 412a within which the plurality of staples 433 and pushers 416 are respectively supported.

As seen in FIGS. 28-43, staple cartridge assembly 410 further includes a knife sled 450 slidably supported within knife slot 412b of cartridge body 412 and being interposed between drive beam 466 and actuation sled 468. As seen in FIG. 33, knife sled 450 defines a knife blade 450a extending from an upper surface thereof and oriented distally, wherein knife blade 450a extends through knife slot 412b of cartridge body 412. Knife sled 450 includes a lock-out spring 451 extending distally therefrom for engaging a lock-out notch 412d formed in a surface of cartridge body 412 (see FIG. 37), as will be discussed in greater detail below. Lock-out spring 451 is biased toward lock-out notch 412d. Prior to firing of cartridge assembly 410, with actuation sled 418 and knife sled 450 at a proximal-most position in cartridge body 412, as seen in FIG. 34-37, lock-out spring 451 is blocked by actuation sled 418 from entering lock-out notch 412d of cartridge body 412.

Staple cartridge assembly 410 includes a bottom cover or retainer 415 configured to maintain the plurality of staple pushers 416, actuation sled 418 and knife sled 450 within cartridge body 412. Retainer 415 supports and aligns the plurality of pushers 416 prior to engagement thereof by the actuation sled 418. During operation, as actuation sled 418 translates through staple cartridge assembly 410, the angled leading edges of cam wedges 418a of actuation sled 418 sequentially contact pushers 416, causing the pushers 416 to translate vertically within retaining slots 412a, urging the staples 433 therefrom. Also, as knife sled 450 translates through knife slot 412b of cartridge body 412, knife blade 450a severs tissue and retaining sutures that extend across knife slot 412b of cartridge body 412.

In operation, as drive screw 464 is rotated, in a first direction, to advance drive beam 466, as described above, drive beam 466 is advanced into contact with knife sled 450 and actuation sled 418 to distally advance or push knife sled 450 and actuation sled 418 through cartridge body 412 and lower jaw 432. As drive beam 466 is continually driven in the distal direction, drive beam 466 maintains contact with knife sled 450 and actuation sled 418, thereby pushing knife sled 450 and actuation sled 418 in the distal direction and to approximate lower jaw 430 and upper jaw 440, as laterally projecting member 466b of drive beam 466 pushes down on the exterior camming surface of upper jaw 440, to eject the staples 414 and fasten tissue, and to simultaneously dissect tissue with knife blade 450a. Knife sled 450, actuation sled 418 and drive beam 466 travel through cartridge body 412 thereby fastening and severing tissue.

Figure 38:
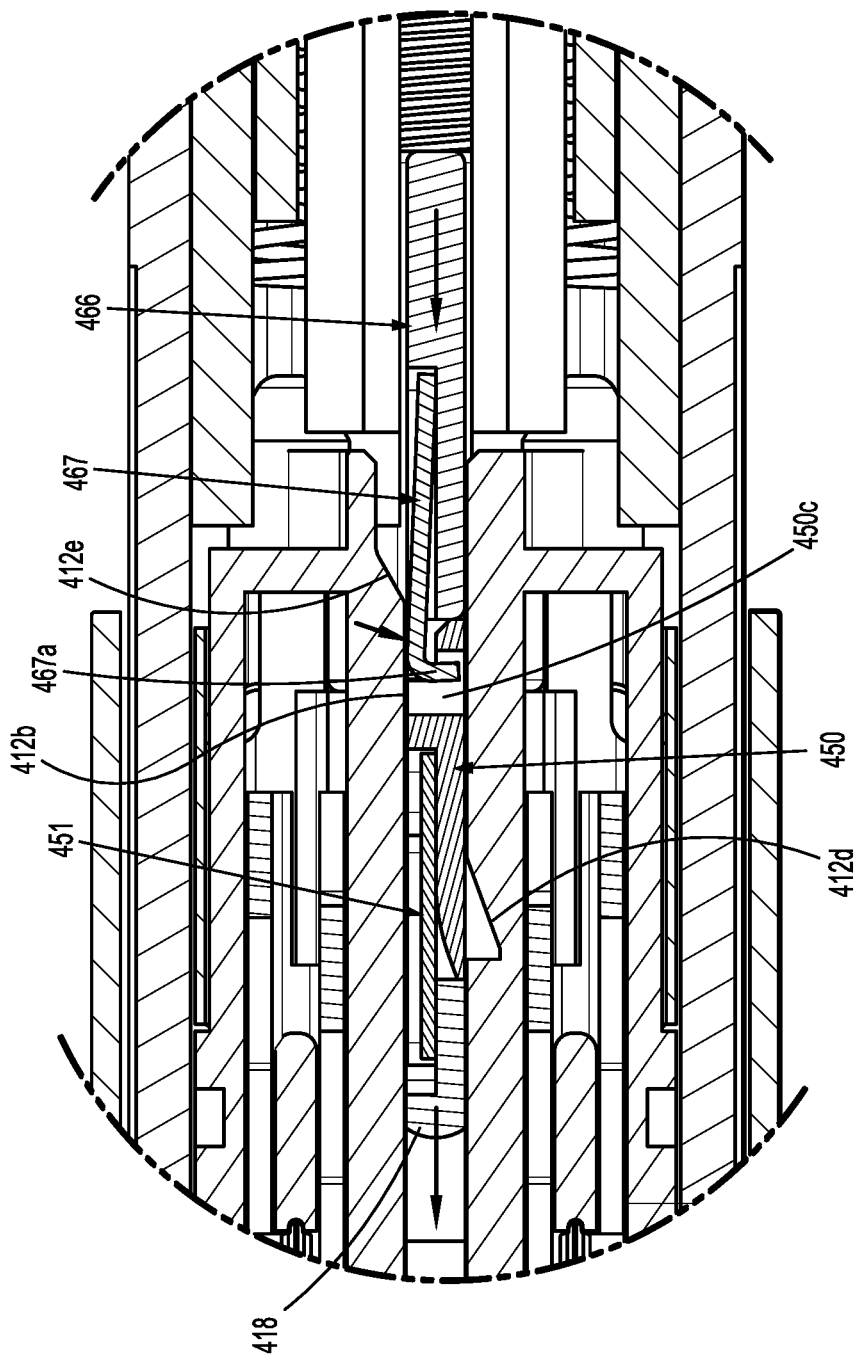
FIG. 38 is a further enlarged view illustrating the drive beam, the knife sled and the actuation sled in a distally advanced position.
Figure 39:
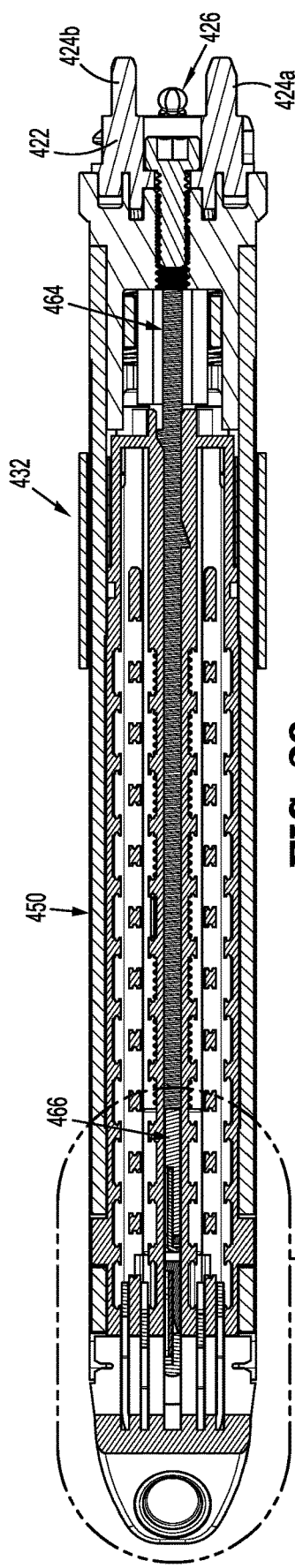
FIG. 39 is a cross-sectional view of the end effector of FIG. 27, as taken through 34-34 of FIG. 27, illustrating the drive beam, the knife sled and the actuation sled in a distal-most position.
Figure 40:
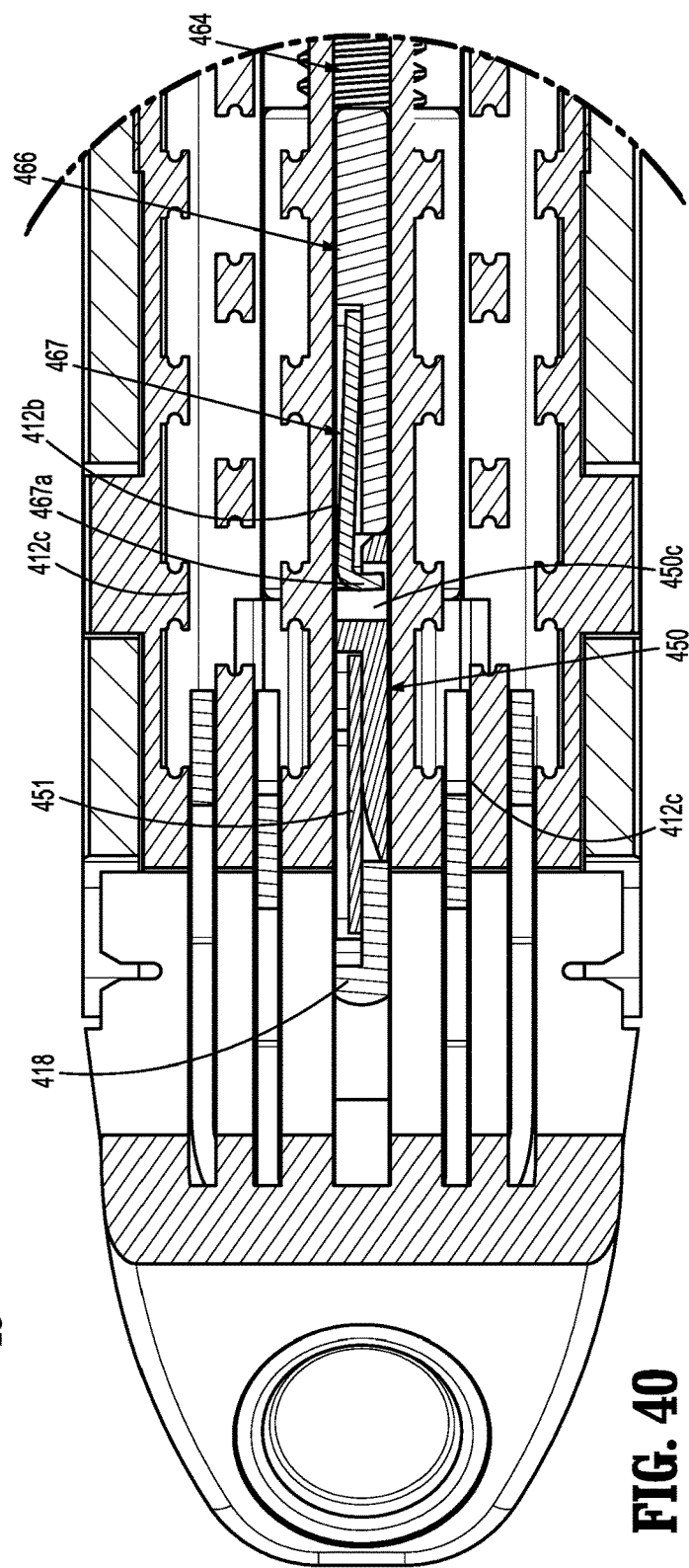
FIG. 40 is an enlarged view of the indicated area of detail of FIG. 39.
Figure 41:
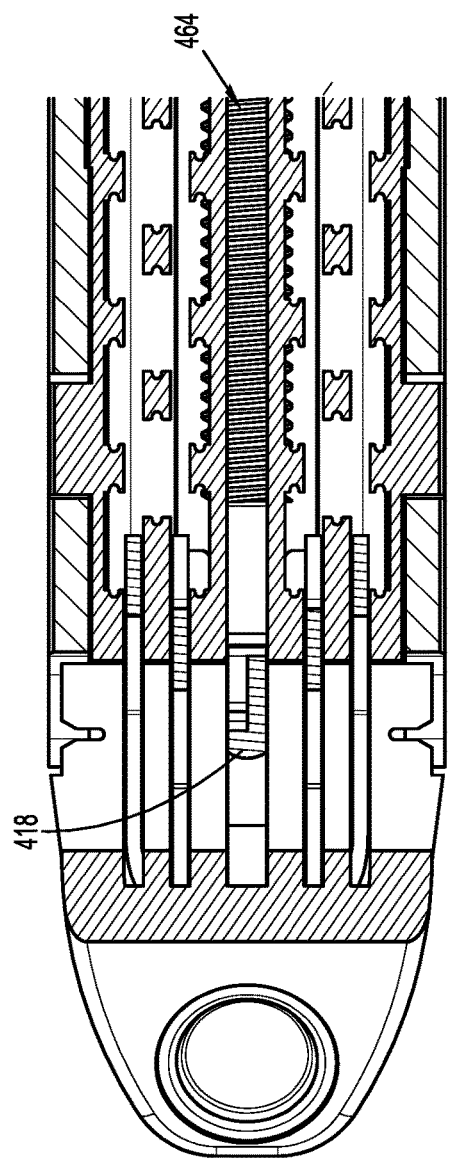
FIG. 41 is a cross-sectional view of a distal end of the end effector of FIG. 27, as taken through 34-34 of FIG. 27, illustrating the actuation sled in a distal-most position.
Figure 42:
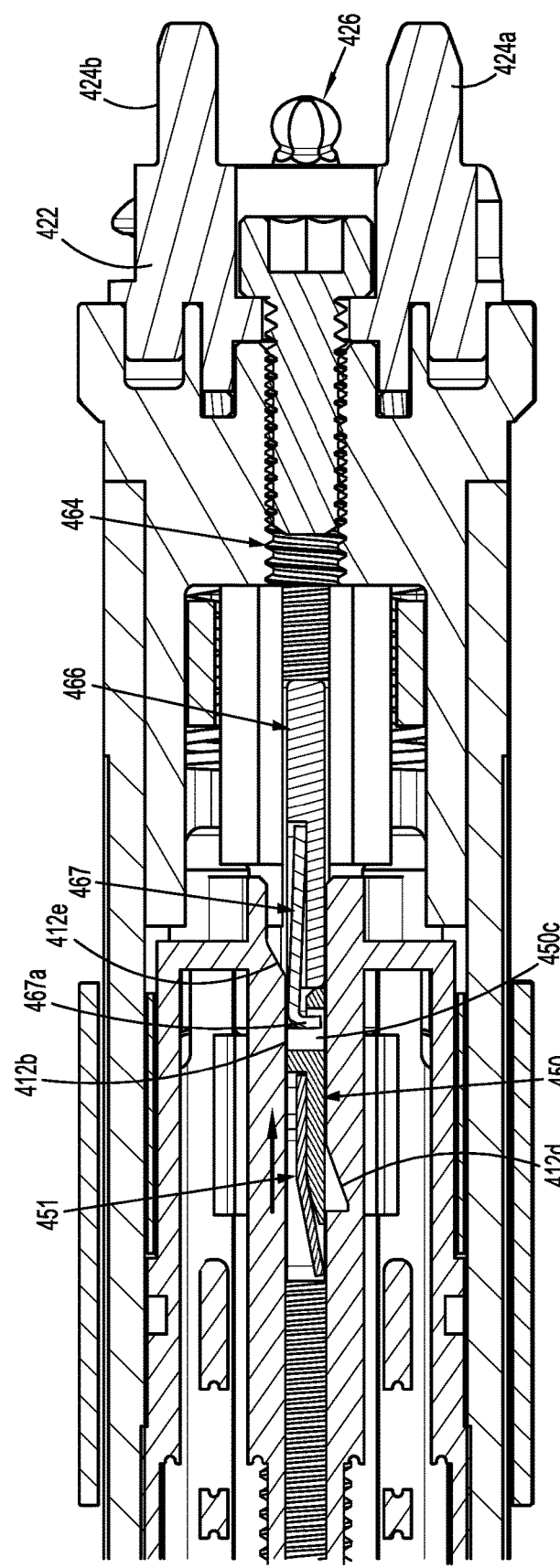
FIG. 42 is a cross-sectional view of a proximal end of the end effector of FIG. 27, as taken through 34-34 of FIG. 27, illustrating the drive beam and the knife sled in a proximal position.

As seen in FIGS. 37 and 38, as drive beam 466 is advanced distally, hook 467a of lock clip 467 exits relief 412e and is cammed into window 450c of knife sled 450 as hook 467a enters knife slot 412b of cartridge body 412. Drive screw 464 is rotated until actuation sled 418, knife sled 450 and drive beam 466 reach a distal-most end of cartridge body 412 and/or lower jaw 432, for a complete firing.

Following a complete or partial firing, drive screw 464 is rotated in an opposite direction to retract drive beam 466. Since and knife sled 450 is connected to drive beam 466 by lock clip 467, as described above, as drive beam 466 is retracted, knife sled 450 is also retracted. Actuation sled 418 will tend to remain at a distal or distal-most position due to its frictional engagement in channels 412c of cartridge body 412 (see FIG. 40). Drive screw 464 is rotated until drive beam 466 and knife sled 450 are returned to the proximal-most position. Once drive beam 466 and knife sled 450 are returned to the proximal-most position, hook 467a of lock clip 467 is permitted to re-enter relief 412e, due to its own resiliency, and disengage from window 450c of knife sled 450. As such, drive beam 466 is disengaged from knife sled 450, and staple cartridge assembly 410 is free to be removed from lower jaw 432.

Figure 43:
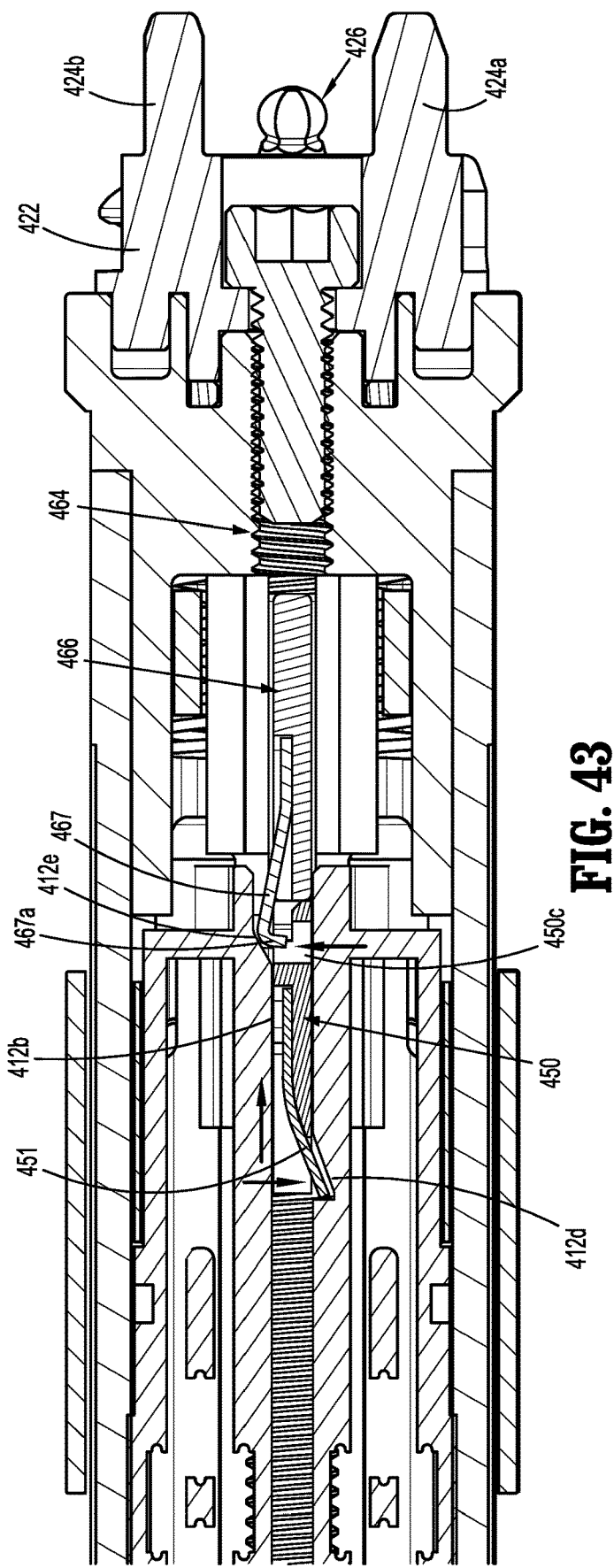
FIG. 43 is a cross-sectional view of a proximal end of the end effector of FIG. 27, as taken through 34-34 of FIG. 27, illustrating the drive beam and the knife sled in a proximal-most position.
Figures 44, 45:
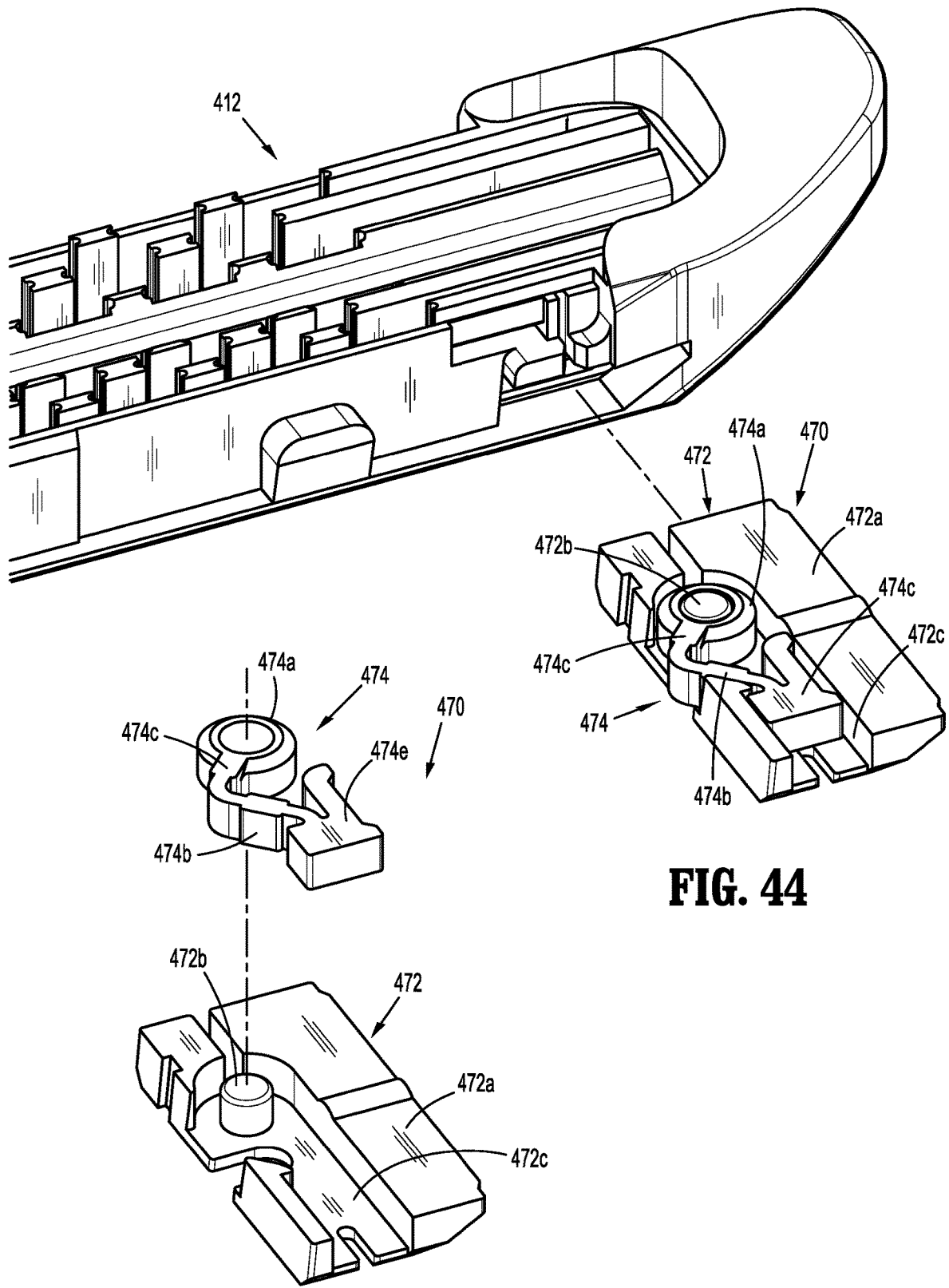
FIG. 44 is a perspective view, with parts partially separated, of a release assembly supported in a distal end of a cartridge assembly of the end effector.
FIG. 45 is a perspective view, with parts separated, of the release assembly of FIG. 44.

Also, when drive beam 466 and knife sled 450 are returned to the proximal-most position, with actuation sled 418 now separated from knife sled 450, since lock-out spring 451 is biased toward lock-out notch 412d, as seen in FIG. 43, lock-out spring 451, which is attached to knife sled 450, is now free to enter lock-out notch 412d and prevent knife sled 450 and/or drive beam 466 being re-advanced, thereby locking-out staple cartridge assembly 410.

In order for drive beam 466 to be re-advanced, a new, un-fired staple cartridge assembly 410 needs to be loaded into lower jaw 432.

Upper jaw 442 of jaw assembly 430 functions as an anvil against which the staples 433 form when actuation sled 418 is advanced during a firing of surgical instrument 100. In particular, upper jaw 442 includes an anvil plate 443, secured to a cover housing 444, in juxtaposed relation to staple cartridge assembly 410. Anvil plate 443 defines a plurality of staple forming pockets (not shown), arranged in longitudinally extending rows that cooperate with the rows of staple retaining slots 412a of staple cartridge assembly 410, when staple cartridge assembly 410 is disposed in lower jaw 432.

Lower jaw 432 is pivotably connected to mounting portion 420 by way of appropriate pivot pins 445 or the like extending through a pair of spaced apart shoulders 432a, 432b disposed near a proximal end thereof. Shoulders 432a, 432b of lower jaw 432 extend into reliefs or the like formed in mounting portion 420.

As seen in FIG. 28, jaw assembly 430 includes at least one biasing member 447, in the form of a compression spring or the like, disposed between each shoulder 432a, 432b of lover jaw 432 and a bearing surface of mounting portion 420 such that lower jaw 432 is spaced from upper jaw 442, until closed, to maintain jaw assembly 430 in an open position. In use, as jaw assembly 430 is closed, by approximating upper jaw 442 and lower jaw 432, biasing members 447 are biased (i.e., compressed) between shoulders 432a, 432b of lower jaw 432 and the bearing surface of mounting portion 420.

Following firing of staple cartridge assembly 410, drive screw 464 is rotated, in a second direction that is opposite the first direction, to withdraw drive beam 466 and knife sled 450, as described above. As drive beam 466 is withdrawn in a proximal direction, biasing members 447 begin to expand to press apart shoulders 432a, 432b of lower jaw 432 from the bearing surface of mounting portion 420 to separate the upper jaw 442 from the lower jaw 432 to open jaw assembly 430.

In accordance with the present disclosure, cartridge body 412 of staple cartridge assembly 410 may be configured and adapted to selectively support a surgical buttress on a tissue contact surface thereof. With reference to FIG. 28, cartridge body 412 of staple cartridge assembly 410 defines a proximal pair of recesses formed near a proximal end thereof and disposed, one each, on opposed sides of longitudinally extending knife slot 412b. Cartridge body 412 further defines a distal pair of recesses 412e formed near a distal end thereof and disposed, one each, on opposed sides of longitudinally extending knife slot 412b. In one embodiment, the distal pair of recesses 412e is preferably non-circular and constricting or otherwise arranged so as to frictionally engage and/or pinch an anchor "S".

As seen in FIG. 28, cartridge body 412 further includes a surgical cartridge buttress "B1", pledget or the like operatively secured to an upper surface or tissue contacting surface thereof, by suture anchors "S1" and "S2", to overlie at least some of the plurality of staple retaining slots 412a and/or at least a portion of a length of longitudinally extending knife slot 412b. In particular, an anchor "S1" is cinched around a proximal portion of surgical cartridge buttress "B1" and each of the proximal pair of recesses and an anchor "S2" is cinched around a distal portion of the surgical cartridge buttress "B1" and each of the distal pair of recesses 412e. The anchors may comprise a surgical suture.

In one particular embodiment, a first end of suture anchor "S1" includes a knot, stop or the like (not shown) sized so as to not pass through one recess of the proximal pair of recesses and a second end of suture anchor "S1" passes over, and transversely across, surgical cartridge buttress "B1", at least once, and back through the other recess of the proximal pair of recesses. For example, the second end of suture anchor "S1" may be pinched or cinched in the other recess of the proximal pair of recesses so as to anchor the second end of the suture anchor "S1" and secure the surgical cartridge buttress "B1" against the tissue contacting surface of cartridge body 412. Similarly, a suture anchor "S2" is used to extend transversely across surgical cartridge buttress "B1" and into engagement with the distal pair of recesses 412e.

Surgical cartridge buttress "B1" includes a proximal pair of notches formed in side edges aligned with the proximal pair of recesses of cartridge body 412, a distal pair of notches formed in side edges thereof aligned with the distal pair of recesses 412e of cartridge body 412, and a proximal notch formed in a proximal edge thereof aligned with longitudinally extending knife slot 412b when cartridge buttress "B1" is secured to cartridge body 412. Cartridge buttress "B1" further includes a tongue or tab extending from a distal edge thereof to facilitate with the attachment of cartridge buttress "B1" to cartridge body 412 during the assembly process. It is contemplated that a width of cartridge buttress "B1" may be reduced in a proximal portion thereof. It is further contemplated that the tongue is removed from cartridge buttress "B1" following securement of cartridge buttress "B1" to cartridge body 412 and prior to packaging or shipment.

As seen in FIGS. 28 and 44-47, cartridge body 412 of staple cartridge assembly 410 includes a cartridge buttress release assembly 470 supported in and near a distal end of cartridge body 412. Release assembly 470 includes a retainer 472 supported in a distal end of cartridge body 412 at a location near a distal end of longitudinally extending knife slot 412b and at least partially extending thereacross. Retainer 472 includes a body portion 472a, a boss 472b extending from a surface thereof, and defines a channel or recess 427c formed in a surface thereof and extending through a side thereof. When supported in cartridge body 412, recess 472c of retainer 472 is in registration with one of the pair of distal recesses 412e of cartridge body 412.

Release assembly 470 further includes a pusher member 474 having a head portion 474a pivotally connected to boss 472b of retainer 472. Pusher member 474 further includes a first leg member 474b extending from head portion 474a and a second leg member 474c connected to a free end of first leg member 474b via a living hinge connection. Pusher member 474 further includes piston 474e connected to a free end of second leg member 474c via a living hinge connection. Piston 474e is slidably disposed and translatable within recess 472c of retainer 472. In certain other embodiments, the pusher is a linkage assembly having a first link pivotably connected to the cartridge body at one end. The other end of the first link is pivotably connected to a first end of a second link. The opposite, second, end of the second link is confined in the recess of the retainer.

As seen in FIG. 46, release assembly 470 includes an unactuated configuration wherein piston 474e does not extend into or overlie the respective one of the pair of distal recesses 412e of cartridge body 412, and first leg member 474b and second leg member 474c are angled with respect to one another and project proximally along longitudinally extending knife slot 412b of cartridge body 412. It is contemplated that release assembly 470 may include a friction fit or snap fit feature for maintaining and/or retaining release assembly 470 in the locking or anchoring configuration at all times following the manufacturing/assembly process and prior to a complete firing of surgical instrument 100.

As seen in FIG. 47, release assembly 470 includes an actuated configuration wherein piston 474e extends into or overlies the respective one of the pair of distal recesses 412d of cartridge body 412 in operative registration therewith, and first leg member 474b and second leg member 474c are extended substantially along a common axis.

In operation, with surgical cartridge buttress "B1" secured against the tissue contacting surface of cartridge body 412, during firing of surgical instrument 100, as drive beam 466 is advanced (i.e., moved from a proximal-most position to a distal-most position), knife blade 450a of knife sled 450 slices through a central section of proximal suture anchor "S1", thereby freeing the proximal end of the surgical cartridge buttress "B1" from cartridge body 412. During use, as the firing stroke of surgical instrument 100 is nearing completion and as actuation sled 418 approaches a distal end of longitudinally extending knife slot 412bc of cartridge body 412, actuation sled 418 contacts the living hinge connection between first leg member 474b and second leg member 474c. As actuation sled 418 is further advanced distally, actuation sled 418 presses against the living hinge connection, causing first leg member 474b and second leg member 474c to extend. As first leg member 474b and second leg member 474c extend, piston 474e is translated through recess 472c of retainer 472. As piston 474e is translated through recess 472c of retainer 472, piston 474e engages the second end of suture anchor "S2" and urges the second end of suture anchor "S2" out of the distal recess 412d of cartridge body 412 that is in registration therewith to release the second end of suture anchor "S2" therefrom. With the second end of suture anchor "S2" released or free from distal recess 412d of cartridge body 412, the distal end of the surgical cartridge buttress "B1" is free to separate from the tissue contacting surface of cartridge body 412.

As seen in FIG. 28, upper jaw 442 further includes a surgical anvil buttress "B2", pledget or the like operatively secured to an upper surface or tissue contacting surface thereof, by anchors "S3" and "S4", to overlie at least some of the plurality of staple forming pockets and/or at least a portion of a length of a longitudinally extending knife slot of anvil plate 443. The anchors may comprise surgical sutures. In particular, a suture anchor "S3" is cinched around a proximal portion of surgical anvil buttress "B2" and each of the proximal pair of recesses and a suture anchor "S4" is cinched around a distal portion of the surgical anvil buttress "B2" and each of a distal pair of recesses 443a formed in opposed side edges of anvil plate 443.

In one particular embodiment, a first end of suture anchor "S3" includes a knot, stop or the like (not shown) sized so as to not pass through one recess of the proximal pair of recesses and a second end of suture anchor "S3" passes over, and transversely across, surgical anvil buttress "B2", at least once, and back through the other recess of the proximal pair of recesses. For example, the second end of suture anchor "S3" may be pinched or cinched in the other recess of the proximal pair of recesses so as to anchor the second end of the suture anchor "S3" and secure the surgical anvil buttress "B2" against the tissue contacting surface of anvil plate 443. Similarly, a suture anchor "S4" is used to extend transversely across surgical anvil buttress "B2" and into engagement with the distal pair of recesses 443a.

Surgical anvil buttress "B2" includes a proximal pair of notches formed in side edges aligned with the proximal pair of recesses of anvil plate 443, a distal pair of notches formed in side edges thereof aligned with the distal pair of recesses 443a of anvil plate 443, and a proximal notch formed in a proximal edge thereof aligned with longitudinally extending knife slot when anvil buttress "B2" is secured to anvil plate 443. Anvil buttress "B2" further includes a tongue or tab extending from a distal edge thereof to facilitate with the attachment of anvil buttress "B2" to anvil plate 443 during the assembly process. It is contemplated that the tongue is removed from anvil buttress "B2" following securement of anvil buttress "B2" to anvil plate 443 and prior to packaging or shipment.

Figure 48:
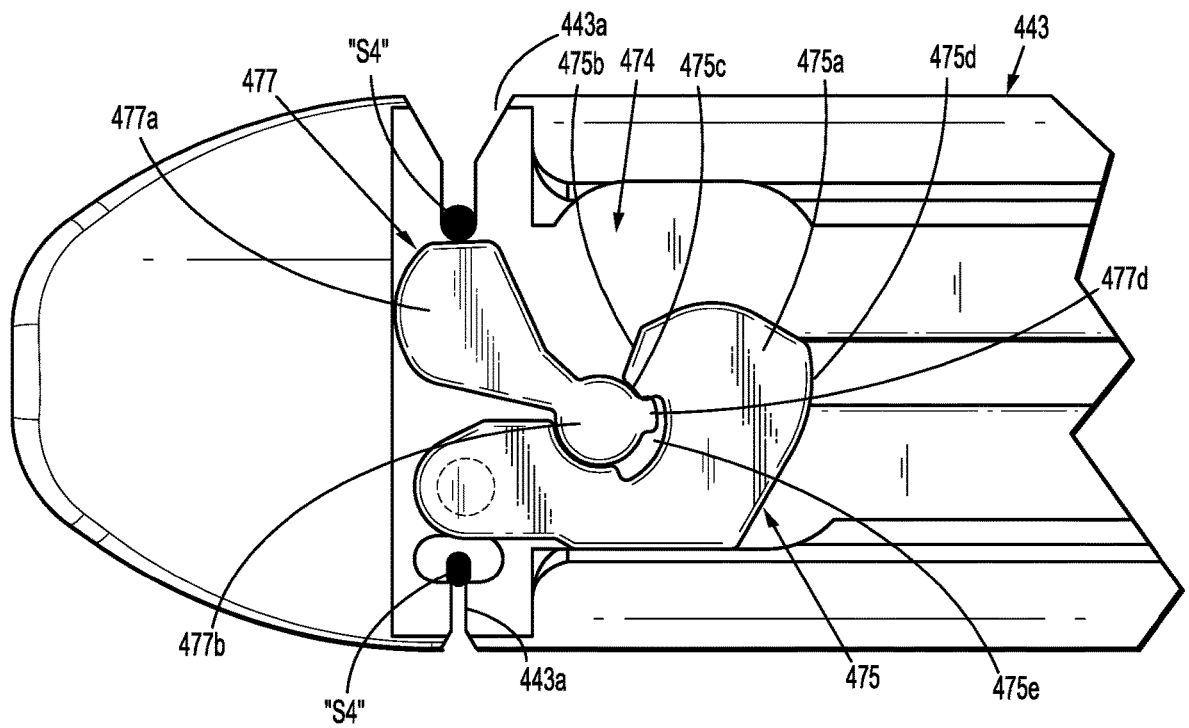
FIG. 48 is a plan view of a release assembly supported in a distal end of an upper jaw of the end effector, illustrated in an unactuated condition.
Figure 49:
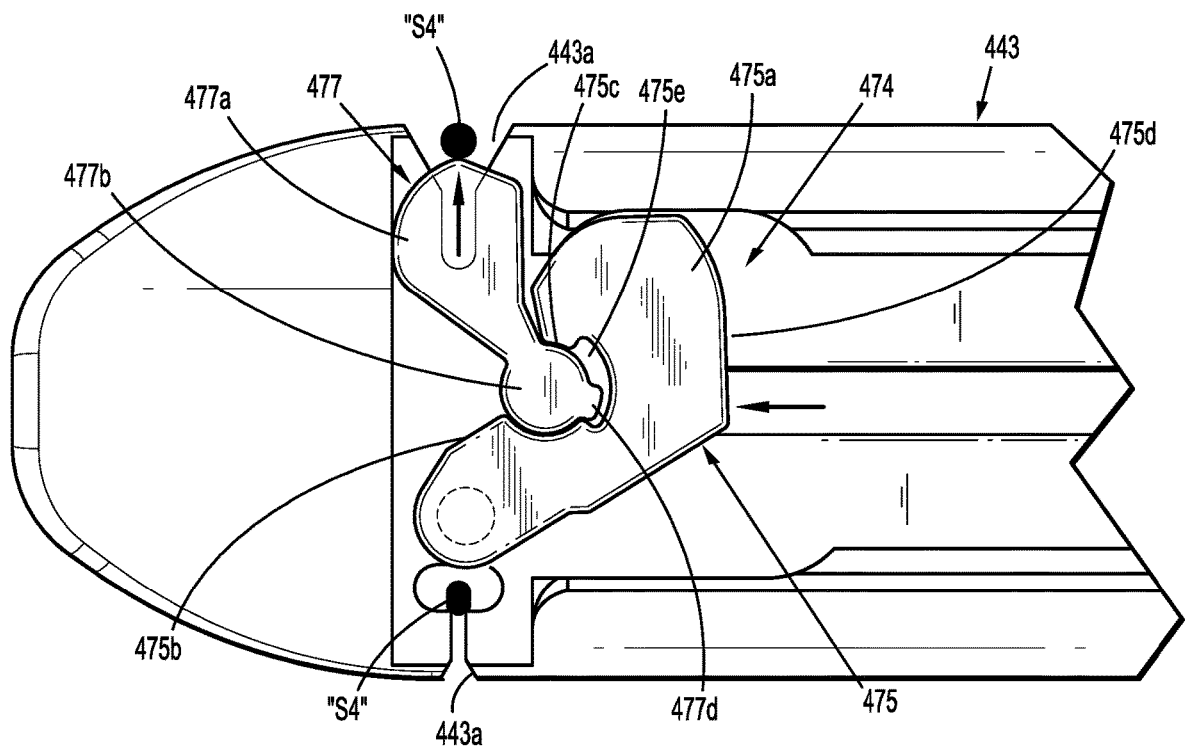
FIG. 49 is a plan view of the release assembly of FIG. 48, illustrated in an actuated condition.

As seen in FIGS. 28 and 48-49, upper jaw 442 of jaw assembly 430 includes a suture release assembly 474 disposed between anvil plate 443 and cover housing 444 at a location in operative registration with a distal pair of side recesses 443a. Suture release assembly 474 includes a link arm 475 pivotally connected to anvil plate 443 and/or optionally cover housing 444. Link arm 475 includes a body portion 475a defining a pocket or recess 475c formed in a first side edge 475b thereof and a camming surface 475d defined substantially along an adjacent side or proximal edge thereof. Pocket 475c has a substantially arcuate, circular or rounded profile and defines an arcuate relief 475e in a side wall thereof. Link arm 475 includes a pivot pin extending from body portion 475a for pivotally connecting link arm 475 to upper jaw 442.

Release assembly 474 further includes a pusher bar 477 pivotally connected to link arm 475 and slidably disposed between anvil plate 443 and cover housing 444. Pusher bar 477 includes a body portion 477a having a substantially rectangular configuration and a head 477b, extending from a corner of body portion 477a, and having a substantially circular or rounded configuration. Head 477b of pusher bar 477 is configured and dimensioned for pivotable and/or rotatable connection in pocket 475c of link arm 475. Head 477b of pusher bar 477 includes a stop member 477d projecting from a side edge thereof and into arcuate relief 475e of pocket 475c of link arm 475. A relative distance of rotation of pusher bar 477 relative to link arm 475 is determined by a relative length of arcuate relief 475e and a relative width of stop member 477d.

As seen in FIG. 48, suture release assembly 474 includes an unactuated configuration wherein pusher bar 477 does not extend into or overlie the respective one of the pair of distal recesses 443a in operative registration therewith, and a longitudinal axis of link arm 475 is oriented substantially parallel with a longitudinal axis of upper jaw 442. It is contemplated that suture release assembly 474 may include a friction fit or snap fit feature for maintaining and/or retaining suture release assembly 474 in the locking or anchoring configuration at all times following the manufacturing/assembly process and prior to a complete firing of the surgical stapling apparatus.

As seen in FIG. 49, suture release assembly 474 includes an actuated configuration wherein pusher bar 477 extends into or overlies the respective one of the pair of distal recesses 443a in operative registration therewith, and a longitudinal axis of link arm 475 is oriented substantially transverse to the longitudinal axis of upper jaw 442.

With reference to FIGS. 28 and 34-43, in operation, with a surgical anvil buttress (not shown) secured against the lower surface of anvil plate 443, during firing of the surgical stapling apparatus, as drive beam 466 is advanced (i.e., moved from a proximal-most position to a distal-most position), knife blade 450a slices through a central section of the proximal suture (not shown), thereby freeing the proximal end of the surgical anvil buttress (not shown) from upper jaw 442. During use, as the firing stroke of the surgical instrument is nearing completion and as drive beam 466 approaches a distal-most end of the knife slot of anvil plate 443, as seen in FIG. 49, actuation sled 418 contacts camming surface 475d of link arm 475, thus urging link arm 475 to rotate or pivot around the pivot pin and, in turn, urging pusher bar 477 to translate in the direction of the slot. As pusher bar 477 is translated, pusher bar 477 comes into contact with and urges the second end of suture "S4" out of the distal recess 443a that is registration therewith to release the second end of suture "S4" therefrom. With the second end of surgical suture "S4" released or free from distal recess 443a, the distal end of the surgical anvil buttress "B2" is free to separate from the tissue contacting surface of anvil plate 443.

Exemplary surgical buttresses "B" for use with the staple cartridge assembly 410 and/or anvil plate 443 disclosed herein are shown and described in commonly assigned U.S. Pat. Nos. 5,542,594, 5,908,427, 5,964,774, 6,045,560, and 7,823,592; commonly assigned U.S. application Ser. No. 12/579,605, filed on Oct. 15, 2009 (now U.S. Patent Publication No. 20110089220); commonly assigned U.S. application Ser. No. 11/241,267, filed on Sep. 30, 2005 (now U.S. Patent Publication No. 2006/0085034); and U.S. application Ser. No. 13/097,194, filed on Apr. 29, 2011, entitled "Surgical Stapling Apparatus;" the entire contents of each of which being incorporated herein by reference.

Surgical buttresses "B" may be fabricated from a suitable biocompatible and bioabsorbable material. Surgical buttresses "B" may be fabricated from a non-absorbent material which does not retain fluid. Surgical buttresses "B" may be fabricated from "BIOSYN" made from GLYCOMER 631 (a block copolymer), a synthetic polyester composed of glycolide, dioxanone and trimethylene carbonate.

One block of the resulting copolymer contains randomly combined units derived from p-dioxanone (1,4-dioxan-2-one) and trimethylene carbonate (1,3-dioxan-2-one). The second block of the copolymer contains randomly combined units derived from glycolide and p-dioxanone. The resulting polyester is an ABA triblock terpolymer possessing about 60% glycolide, about 14% dioxanone, and about 26% trimethylene carbonate.

The surgical buttress may comprise polymers or copolymers of glycolide, lactide, poly caprolactone, trimethylene carbonate, dioxanone, caprolactone, and may be molded, extruded, etc. into a desired shape, or formed into a knitted, woven, braided, non-woven or felted material.

Figure 50:
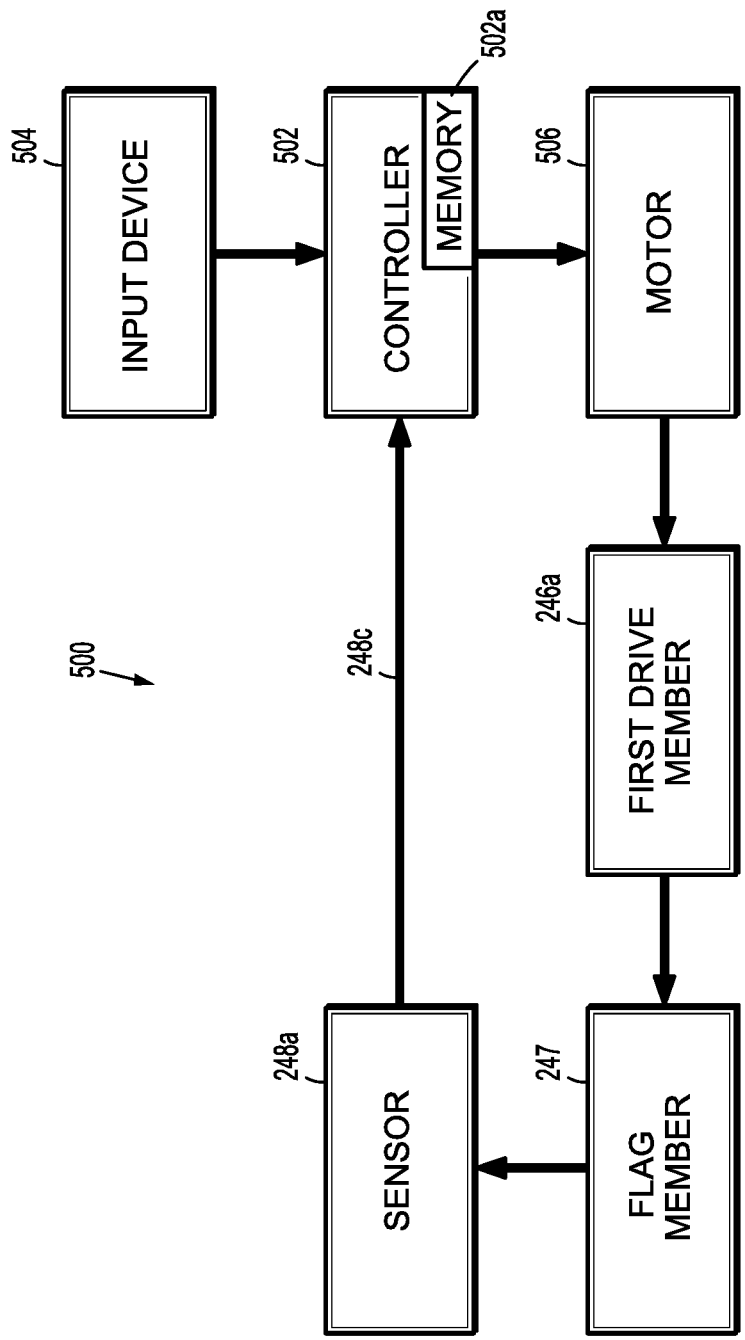
FIG. 50 is a system block diagram of an end stop detection system in accordance with an embodiment of the present disclosure.

Turning to FIG. 50, an end stop detection system is shown generally as 500. End stop detection system includes a controller 502. Controller 502 receives an input from input device 504 (e.g., actuation of a trigger, lever, or button) and controls motor 506 based on the input. Motor 506 causes first drive member 246a to rotate in a first direction causing the flag member 247 to translate axially along first drive member 246a. When flag member 247 contacts sensor 248a, sensor 248a provides a high electrical signal to controller 502 causing controller 502 to stop motor 506.

Figure 51:
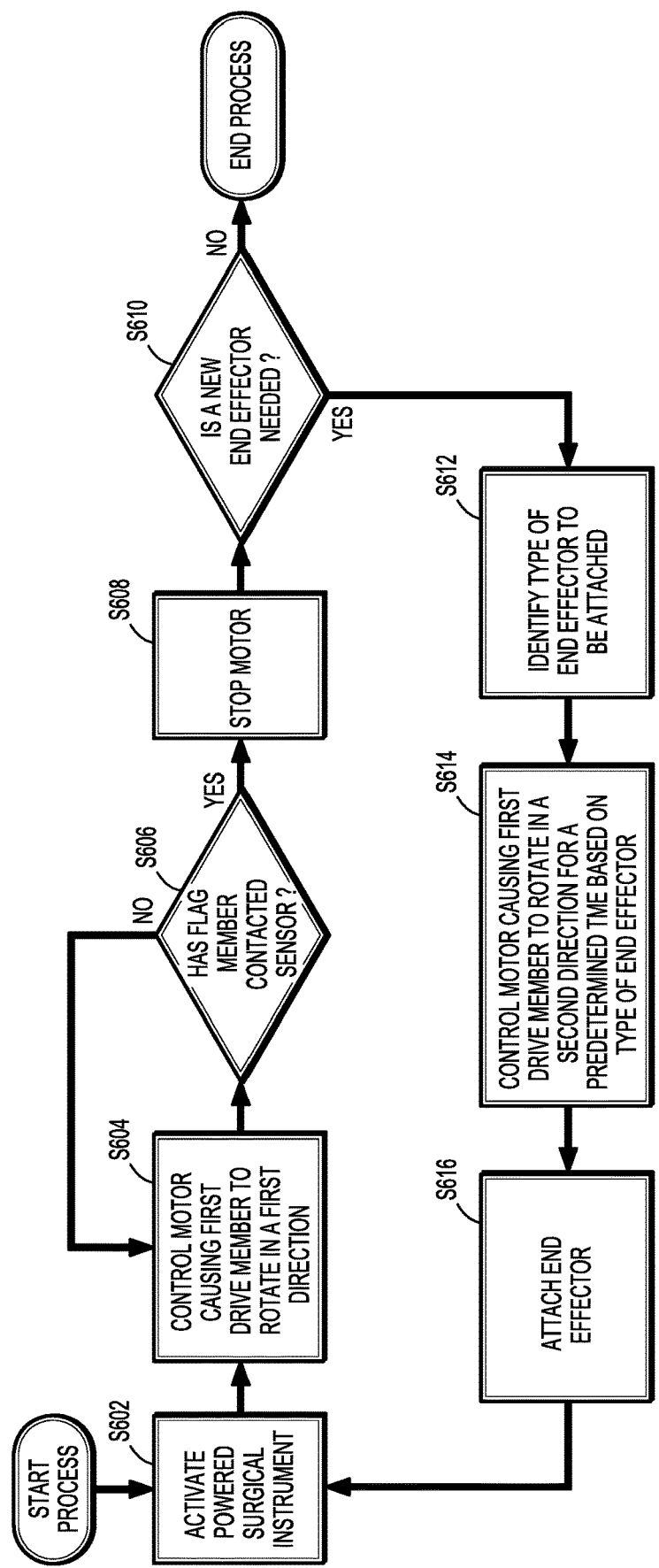
FIG. 51 is a flow chart depicting an end stop detection method in accordance with an embodiment of the present disclosure.

FIG. 51, which will be discussed in conjunction with FIG. 50, depicts an end stop detection method based on an algorithm stored in controller 502. The process begins with step s602, where the powered surgical instrument 100 is activated. In step s604, the motor 506 is controlled so that the first drive member 246a is rotated in a first direction causing flag member 247 to translate distally along first drive member 246a. In step s606, controller 502 determines whether flag member 247 has contacted sensor 248a based on whether the controller received a high electrical signal from sensor 248a. If controller 502 did not receive a high electrical signal from sensor 248a, the process returns to step s604. If controller 502 receives a high electrical signal from sensor 248a, the process proceeds to step s608 where motor 506 is stopped.

Then a determination is made whether a new end effector 400 is needed in step s610. Such determination may be automatically based on a surgical plan stored in controller 502 or may be inputted by a clinician. If a new end effector is not needed, the process ends. If a new end effector 400 is needed, the process proceeds to step s612 where the controller 502 identifies the type of end effector 400 to be attached. Such identification may be inputted by a clinician, based on the surgical plan stored in controller 502, or based on an identification device on end effector 400 such as a bar code or a radio-frequency identification (RFID) tag. Based on the type of end effector 400 identified, controller 502 controls motor 506 to rotate the first drive member 246a in a second direction, opposite the first direction, for a predetermined amount of time. The predetermined time corresponds to the type of end effector and may be obtained from a table stored in a memory 502a of controller 502. Such rotation of the first drive member 246a in the second direction causes flag member 247 to translate proximally. By specifying the amount of time to rotate the first drive member 246a, the flag member 247 can be positioned so that the distance the between the flag member 247 and the sensor 248a corresponds to the end stop distance of the identified end effector 400. In steps s616, the identified end effector 400 is attached to the powered surgical instrument 100 and the process proceeds to step s602.

It will be understood that various modifications may be made to the embodiments disclosed herein. For example, surgical instrument 100 and/or cartridge assembly 410 need not apply staples but rather may apply two part fasteners as is known in the art. Further, the length of the linear row of staples or fasteners may be modified to meet the requirements of a particular surgical procedure. Thus, the length of the linear row of staples and/or fasteners within a staple cartridge assembly may be varied accordingly. Therefore, the above description should not be construed as limiting, but merely as exemplifications of preferred embodiments. Those skilled in the art will envision other modifications within the scope and spirit of the claims appended thereto.

What is claimed is:

1. An end stop detection method for a powered surgical instrument having a hand-held surgical instrument, an end effector and a shaft assembly configured to selectively interconnect the hand-held surgical instrument and the end effector, the shaft assembly including a drive member, a flag member, and a sensor, the method comprising:
   controlling a motor within the hand-held surgical instrument to cause the drive member within the shaft assembly to rotate in a first direction thereby causing the flag member within the shaft assembly to translate axially along the drive member toward the sensor within the shaft assembly;
   determining when the flag member contacts the sensor; and
   stopping the motor when the flag member contacts the sensor to stop an actuation of the end effector.

2. The end stop detection method of claim 1, further comprising removing the end effector after stopping the motor.

3. The end stop detection method of claim 2, further comprising determining when a new end effector is needed based on a user input or a predetermined surgical plan.

4. The end stop detection method of claim 3, further comprising:
   identifying a type of end effector to be attached to the shaft assembly as the new end effector; and
   controlling the motor within the hand-held surgical instrument to cause the drive member to rotate in a second direction opposite the first direction thereby causing the flag member to translate axially along the drive member away from the sensor, wherein the drive member is rotated for a predetermined amount of time based on the type of end effector to be attached to the shaft assembly.

5. The end stop detection method of claim 3, further comprising attaching the new end effector to the shaft assembly.

6. An end stop detection method for a powered surgical instrument, the method comprising:

connecting a shaft assembly including a drive member, a flag member, and a sensor to a handheld surgical instrument including a motor such that the motor is operably coupled to the drive member, wherein the shaft assembly is configured to selectively interconnect the handheld surgical instrument and an end effector;

actuating the motor to drive rotation of the drive member, within the shaft assembly, in a first direction, thereby translating the flag member, within the shaft assembly, axially along the drive member;

determining when the flag member contacts the sensor within the shaft assembly; and stopping the motor when the flag member contacts the sensor to stop an actuation of the end effector.

7. The end stop detection method of claim 6, further comprising connecting an end effector to the shaft assembly prior to actuating the motor.

8. The end stop detection method of claim 7, further comprising removing the end effector after stopping the motor.

9. The end stop detection method of claim 8, further comprising:

identifying a type of a new end effector to be attached to the shaft assembly; and actuating the motor to drive rotation of the drive member to rotate in a second direction opposite the first direction, thereby translating the flag member axially along the drive member away from the sensor, wherein the drive member is rotated a predetermined amount based on the identified type of the new end effector.

10. The end stop detection method according to claim 9, wherein the predetermined amount is a predetermined amount of time.

11. The end stop detection method of claim 9, further comprising attaching the new end effector to the shaft assembly.

12. The end stop detection method of claim 6, further comprising:

identifying a type of an end effector to be attached to the shaft assembly; and actuating the motor to drive rotation of the drive member to rotate in a second direction opposite the first direction, thereby translating the flag member axially along the drive member away from the sensor, wherein the drive member is rotated a predetermined amount based on the identified type of the end effector.

13. The end stop detection method according to claim 12, wherein the predetermined amount is a predetermined amount of time.

14. The end stop detection method of claim 12, further comprising attaching the end effector to the shaft assembly.

* * * * *